(12) United States Patent
Leventhal et al.

(10) Patent No.: US 11,810,671 B2
(45) Date of Patent: Nov. 7, 2023

(54) SYSTEM AND METHOD FOR PROVIDING HEALTH INFORMATION

(71) Applicant: K Health Inc., New York, NY (US)

(72) Inventors: Ariel Leventhal, Tel Aviv (IL); Daniel Souroujon, Tel Aviv (IL); Adam Singolda, New York, NY (US); Ran Shaul, Demarest, NJ (US); Allon Bloch, Princeton, NJ (US); Roy Malka, Binyamina (IL); Tom Haramaty, Tel Aviv (IL); Israel Roth, Raanana (IL)

(73) Assignee: K HEALTH INC.

( * ) Notice: Subject to any disclaimer, the term of this patent is extended or adjusted under 35 U.S.C. 154(b) by 855 days.

(21) Appl. No.: 16/711,385

(22) Filed: Dec. 11, 2019

(65) Prior Publication Data

US 2020/0185102 A1 Jun. 11, 2020

Related U.S. Application Data

(60) Provisional application No. 62/778,226, filed on Dec. 11, 2018.

(51) Int. Cl.
*G16H 50/20* (2018.01)
*G16H 10/60* (2018.01)
(Continued)

(52) U.S. Cl.
CPC .......... *G16H 50/20* (2018.01); *A61B 5/7267* (2013.01); *A61B 5/7275* (2013.01);
(Continued)

(58) Field of Classification Search
CPC ........ G16H 50/20; G16H 70/60; G16H 10/60; G16H 50/70; G06N 20/00; G06N 5/04;
(Continued)

(56) References Cited

U.S. PATENT DOCUMENTS

2008/0201280 A1 8/2008 Martin et al.
2008/0228769 A1 9/2008 Lita et al.
(Continued)

FOREIGN PATENT DOCUMENTS

WO WO 2012/122122 A1 9/2012

OTHER PUBLICATIONS

Extended European Search Report, Application No. 19894546.1, dated Aug. 16, 2022.
(Continued)

*Primary Examiner* — Michael Tomaszewski
(74) *Attorney, Agent, or Firm* — Pearl Cohen Zedek Latzer Baratz LLP

(57) ABSTRACT

Systems and methods for providing health information. A method for building a health predictive model is provided based on a plurality of electronic medical records representing a plurality of electronic medical cases each associated with a diagnosis of a medical condition. Symptom-attribute-value (SAV) ontology objects are extracted from the plurality of electronic medical records. A plurality of feature vectors respectively associated with the medical cases and at least partially based on the SAV ontology objects are generated. The health predictive model can be trained based on the feature vectors by using the diagnoses as category labels of the training. The method for providing health information can include presenting a probability vector by inputting a current feature vector into the health predictive model. The current feature vector can be based on responses received via a health conversation. Advantageously, personalized and highly relevant medical advice can be provided to a user.

8 Claims, 48 Drawing Sheets

(51) Int. Cl.
*G16H 70/60* (2018.01)
*G16H 50/70* (2018.01)
*G06N 5/04* (2023.01)
*G06N 20/00* (2019.01)
*A61B 5/00* (2006.01)
*G06F 40/117* (2020.01)
*G06F 40/30* (2020.01)
*G06F 40/295* (2020.01)

(52) U.S. Cl.
CPC .......... *A61B 5/7278* (2013.01); *A61B 5/7282* (2013.01); *G06F 40/117* (2020.01); *G06F 40/295* (2020.01); *G06F 40/30* (2020.01); *G06N 5/04* (2013.01); *G06N 20/00* (2019.01); *G16H 10/60* (2018.01); *G16H 50/70* (2018.01); *G16H 70/60* (2018.01)

(58) Field of Classification Search
CPC ...... G06F 40/295; G06F 40/117; G06F 40/30; A61B 5/7267; A61B 5/7275; A61B 5/7278; A61B 5/7282
USPC .......................................................... 705/2–3
See application file for complete search history.

(56) References Cited

U.S. PATENT DOCUMENTS

| | | |
|---|---|---|
| 2014/0046683 A1 | 2/2014 | Michelson et al. |
| 2014/0167917 A2 | 6/2014 | Wallace et al. |
| 2014/0181128 A1 | 6/2014 | Riskin et al. |
| 2017/0039186 A1 | 2/2017 | Pestian et al. |
| 2017/0083547 A1 | 3/2017 | Tonkin et al. |
| 2017/0124158 A1 | 5/2017 | Mirhaji |
| 2018/0046773 A1* | 2/2018 | Tang ...................... G16H 40/20 |
| 2018/0089568 A1* | 3/2018 | Allen ....................... G06N 5/02 |
| 2018/0366222 A1* | 12/2018 | Tang ...................... G06N 3/006 |
| 2019/0034591 A1 | 1/2019 | Mossin et al. |
| 2020/0098476 A1* | 3/2020 | Loscutoff ............... G16H 50/70 |

OTHER PUBLICATIONS

Amatriain, Xavier, "NLP & Healthcare: Understanding the Language of Medicine," (Nov. 5, 2018); https://medium.com/cural-tech/nlp-healthcare-understanding-the-language-of-medicine-e9917bbf49e7.

* cited by examiner

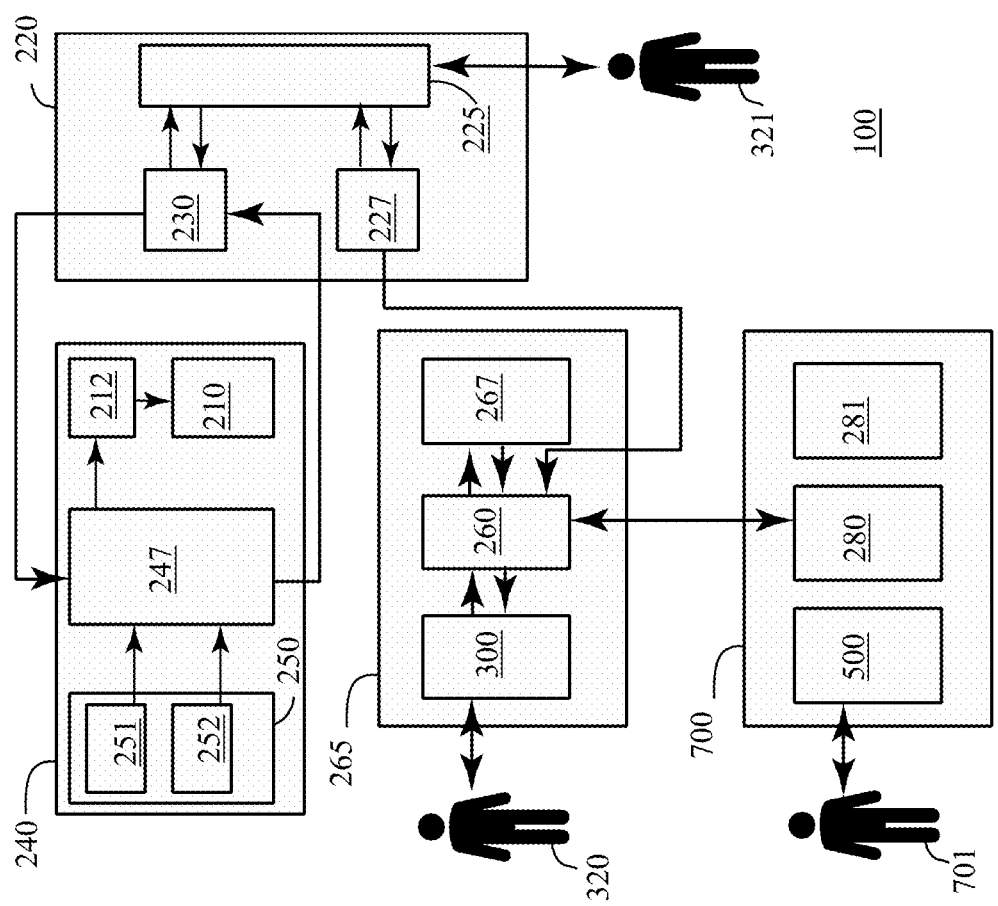

Condition: Upper Respiratory Infection

| | Male | Female |
|---|---|---|
| 15-20 | 0.3 | 0.3 |
| 20-25 | 0.14 | 0.12 |
| 25-30 | 0.21 | 0.25 |
| 30-35 | 0.27 | 0.34 |
| 35-40 | 0.31 | 0.37 |
| ... | | |
| above 90 | 0.43 | 0.42 |

$P(y_j \mid (age, gender))$

*Fig. 19*

SYSTEM AND METHOD FOR PROVIDING HEALTH INFORMATION

CROSS-REFERENCE TO RELATED APPLICATIONS

This application claims priority to U.S. provisional patent application, Ser. No. 62/778,226, filed on Dec. 11, 2018, the disclosure of which is incorporated by reference herein in its entirety and for all purposes.

FIELD

The disclosed embodiments relate generally to digital healthcare systems and more particularly, but not exclusively, to systems and methods for providing health information.

BACKGROUND

Digital healthcare solutions provide an inexpensive and quick way for people to receive health information pertaining to certain symptoms and diseases (or medical conditions) prior to, or in additional to, deciding to visit a doctor's office in person. For example, conventional websites allow patients to search for information related to a symptom or illness. Similar information systems also serve professional care givers, such as doctors and nurses. However, the level of granularity in such systems is very low, or in other words, the information is generic, and not always accurate for a particular situation. In an interaction with a non-professional, there is no personalized interaction with the patient to establish any sense of trust in the patient. Instead, these websites often provide an overwhelming amount of information that is difficult to navigate and is not always relevant to the patient's symptoms. Further, conventional solutions tend to lead people from mild symptoms to scary and unlikely conditions, which can cause unnecessary anxiety, stress, and doubt.

A typical digital healthcare solution predicts diagnosis of possible medical conditions based on information provided by the patient via a predetermined form, such as asking the user questions and receiving answers. The number of rules that are required to capture the questions for most diseases is vast, and the level of difficulty grows exponentially— essentially, making conventional systems either: extremely simplistic (to handle the complexity), conservative (to reduce risk as the complexity is high), and/or frankly wrong (with weird questions popping up).

Conventional systems are simplistic. A typical method builds conditional (e.g., IF→THEN) issue trees that cannot expand beyond a few layers. For example, a typical decision tree may have only ten binary (e.g., yes/no) questions. The number of possible ways to construct a decision tree from n questions is $(2n)!/(n!(n+1)!)$ which gives about 16,500 possibilities for 10 questions, and increases to almost 10 M possibilities for 15 question and to over 6.5 billion for 20 questions.

When the number of possible questions rise and the questions become more complex (e.g., involving multiple choice questions), the number of options grows dramatically. Therefore, conventional systems minimize the number of necessary layers.

As a further disadvantage, conventional systems often err on the side of being too conservative. If there is any doubt, the system defaults to sending the patient to the emergency room.

In conventional systems, two methods are used: A. Rule book (or protocol) based on medical literature; or B. Very basic artificial intelligence (AI) based on user answers. Disadvantages of those solutions are: A. unable to handle complexity; B. Limited structured and accurate data, leading to inaccurate AI outcomes (bad data in, and thus bad conclusions out).

Further, in conventional systems, the user has no idea how the system progress in the process of questions and answers, or how the system makes its decisions.

Conventional systems typically deal with the possible diagnosis given a set of symptoms and provide static information. Such systems provide multiple possible medical conditions or diseases related to those symptoms, often not considering specifics of the person or the situation. Furthermore, once a condition is mentioned as a possible diagnosis, static (i.e., not personalized to the current patient) and textbook information linked to that condition is provided including possible treatments, lab tests, or medications. Nevertheless, the static and textbook information does not consider the specific personal information of the current user.

Conventional systems typically are tuned to cater to either a non-professional end-user (website or mobile application) where the information provided is presented in laymen terms, with little insight into the particular person and case, or to a professional (for example, a decision support system) where more detailed information is presented. In conventional situations where professional information on a particular condition is presented with detailed information, it is presented in a generic matter and not tailored to the particular case.

In view of the foregoing, a need exists for improved methods and systems for digital healthcare in an effort to overcome the aforementioned obstacles and deficiencies of conventional health analysis systems.

BRIEF DESCRIPTION OF THE DRAWINGS

FIG. 3A is a diagram illustrating another exemplary embodiment of the environment of FIG. 1.

FIG. 19 is a diagram illustrating one embodiment of statistics for estimating a reference population index using the server system of FIG. 3.

Figure 1:
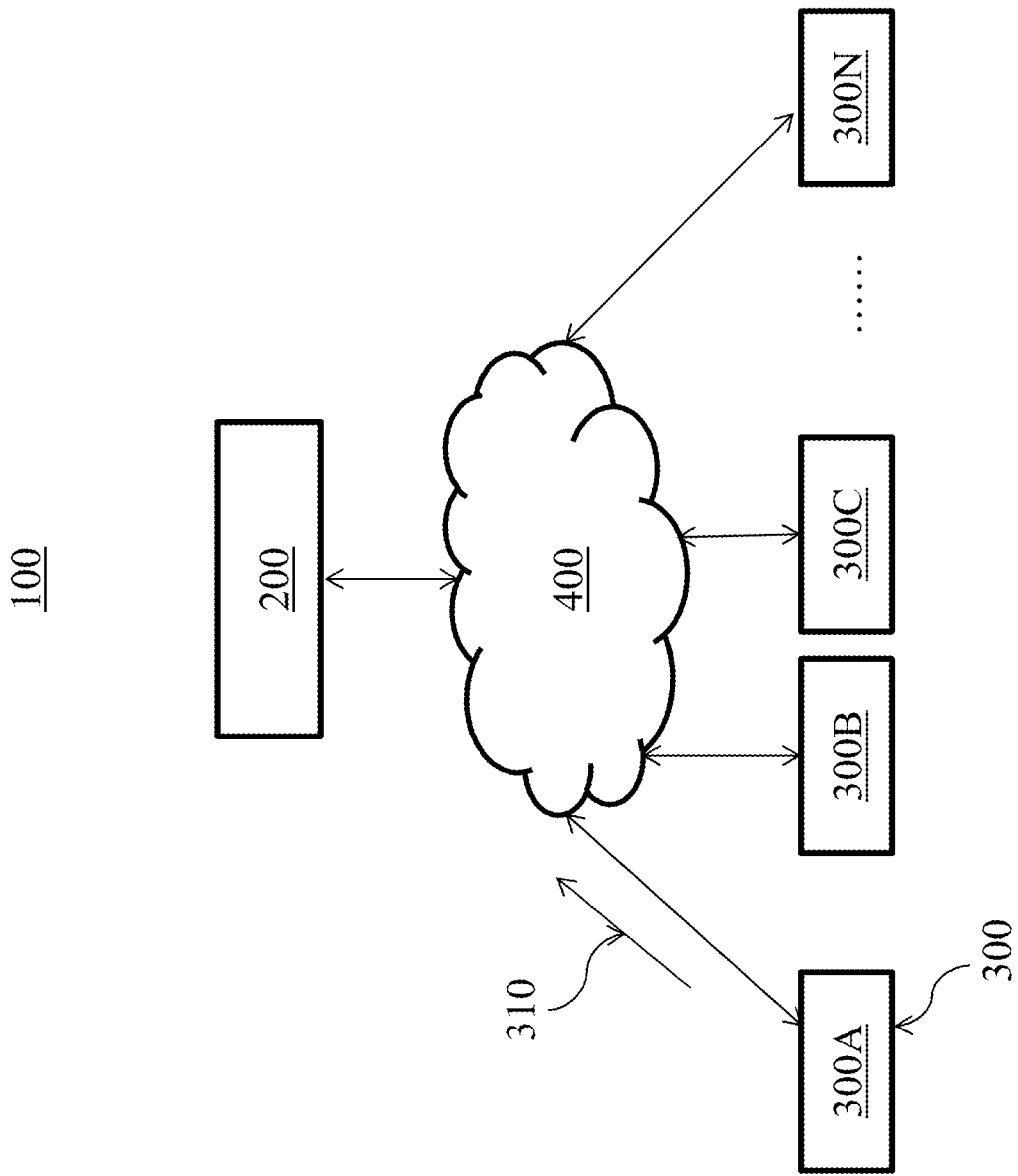
FIG. 1 is a diagram illustrating an exemplary embodiment of an environment for providing health information, wherein the environment includes a server system and one or more client devices.

It should be noted that the figures and the Appendix are not drawn to scale and that elements of similar structures or functions are generally represented by like reference numerals for illustrative purposes throughout the figures. It also should be noted that the figures are only intended to facilitate the description of the preferred embodiments. The figures do not illustrate every aspect of the described embodiments and do not limit the scope of the present disclosure.

DETAILED DESCRIPTION OF THE PREFERRED EMBODIMENTS

The age of information brings a vast amount of raw data to both patients and physicians. Transforming the raw data to insightful actionable information poses a unique challenge in healthcare that requires the right context for the right information to be truly actionable. Currently-available methods are incapable or ineffective in providing contextual health information and lack the ability to provide many of the desired properties for an effective healthcare system in the information era. Such properties include accessible 24/7 personalized medical advice at an affordable cost; empowering people for self-care; enabling immediate medical care actions with dramatically increased convenience and accuracy; providing healthcare services for remote areas that do not have easy access to a medical facility; providing with a physician the right context in the right time to support his decisions for the benefit of his patient, and many more. Many of the above challenges are addressed, according to one embodiment disclosed herein, by an environment 100 as illustrated in FIG. 1.

Turning to FIG. 1, the environment 100 is shown as including a server system 200 communicating with one or more client devices 300 via at least one communication network 400. The server system 200 can include one or more computer systems that are individually and/or collectively configured to transfer information and/or data among the client devices 300. An exemplary server system 200 can receive data from a selected client device 300 and send the data to one or more other client devices 300 chosen based on predetermine criteria. Coded instructions of a program can be installed on the server system 200 to implement the disclosed functions.

The plurality of client devices 300 can include any number of uniform and/or different client devices 300, illustratively shown as client devices 300A, 300B, 300C, . . . through 300N. Each client device 300 can be located at a device location. Each client device 300 can include a computer system and/or electronic device. An exemplary client device 300 can include a personal computer (PC) and/or mobile computer device, such as a tablet computer and/or a smart phone. Coded instructions, for example, of an application (or app) can be installed on each of the client devices 300 to implement the disclosed functions.

The communication network 400 can support wired and/or wireless communication between the server system 200 and the client device 300. Exemplary communication networks 400 can include, but are not limited to, a local area network (LAN), a wide area network (WAN), a business intranet, the Internet, a wireless network, a cellular network, and/or other networks that use radio, Wireless Fidelity (Wi-Fi), satellite, and/or broadcast communications.

The communication network 400 can support communications via one or more selected communications standards, protocols and/or technologies including, but not limited to, Global System for Mobile Communications (GSM), Enhanced Data GSM Environment (EDGE), wideband code division multiple access (W-CDMA), code division multiple access (CDMA), time division multiple access (TDMA), Bluetooth, Wireless Fidelity (Wi-Fi) (for example, IEEE 802.11a, IEEE 802.11b, IEEE 802.11g and/or IEEE 802.11n), voice over Internet Protocol (VoIP), Wi-MAX, a protocol for email (for example, Internet message access protocol (IMAP) and/or post office protocol (POP)), instant messaging (for example, extensible messaging and presence protocol (XMPP), Session Initiation Protocol for Instant Messaging and Presence Leveraging Extensions (SIMPLE), and/or Instant Messaging and Presence Service (IMPS)), and/or Short Message Service (SMS)).

Although FIG. 1 shows the environment 100 as including one communication network 400 for purposes of illustration only, the environment 100 can include any suitable number of uniform and/or different communication networks 400. The client devices 300 can communicate with the server system 200 via uniform and/or different communication networks 400.

FIG. 1 shows the server system 200 as receiving one or more responses 310 from the client device 300A. The responses 310 can be associated with a user account that is logged in via the client device 300A. The responses 310 can include complaints of symptoms and/or answer(s) to questions provided by the server system 200. In some embodiments, a selected response 310 can include information about multiple symptoms or other specific case information.

Figure 2:
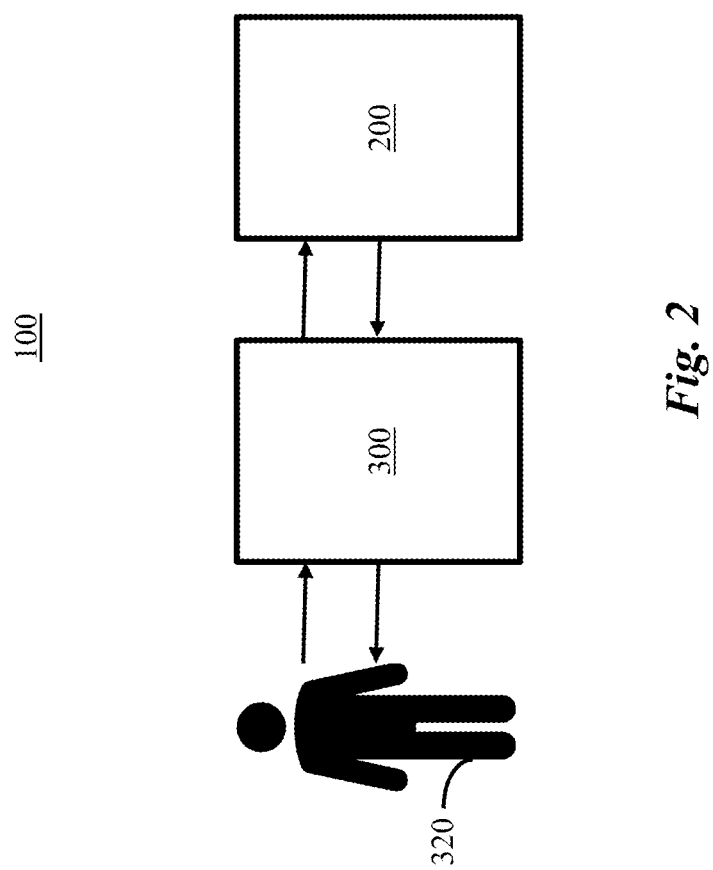
FIG. 2 is a diagram illustrating another exemplary embodiment of the environment of FIG. 1.

Turning to FIG. 2, the client device 300 is shown as being operated by an operator 320. The client device 300 can be configured to present one or more user interfaces 340 (shown in FIGS. 14-18 and 21-32) to interact with the operator 320. The operator 320 can open the app on the client device 300, log in to a user account that is registered in a user database (not shown) in the server system 200, and communicate with the server system 200. In some embodiments, the server system 200 can represent a backend functionality for the app. Each user account can be associated with an entity, such as a patient. The user database can include profile information and/or medical history for each user account. The profile information can include name (optional), age, gender, sex, weight, height, smoking habit, and/or the like.

In one embodiment, a computer-implemented program is running on a backend server in the cloud. However, those of ordinary skill in the art will appreciate that the program can run within the mobile app, on a mobile device, etc.

In one embodiment, a user account can represent either an end user such a patient, or a professional care giver such as a doctor or nurse. Furthermore, in some embodiments, the information provided by operator 320, can be of a different person, and the information provided by the system can be used to communicate health information between different entities as part of a health system (such as between different doctors discussing a certain case).

Figure 3B:
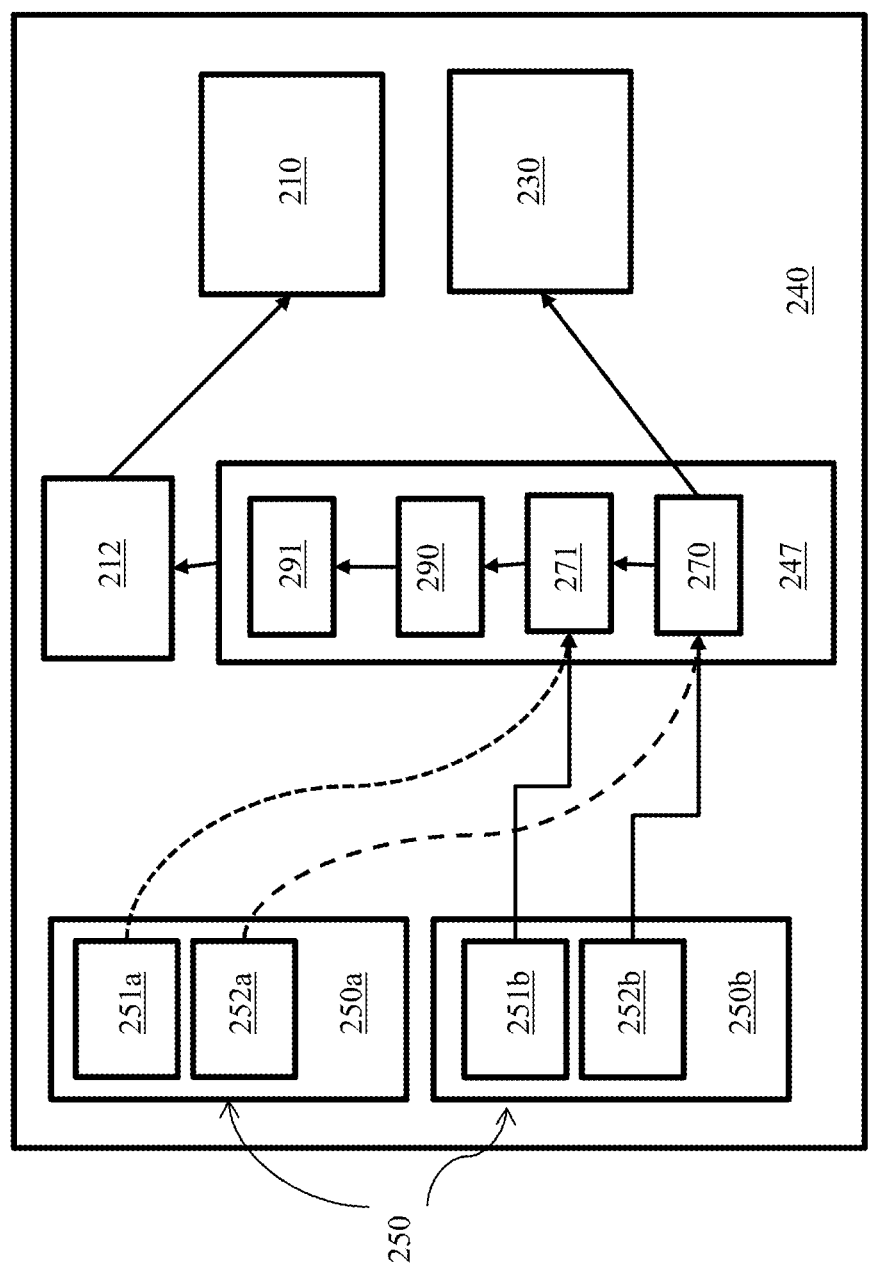
FIG. 3B is a diagram illustrating an exemplary embodiment of the server system of FIG. 1.

FIGS. 3A-3E show exemplary diagrams illustrating various embodiment of the environment 100 to depict various level of details. In each of FIGS. 3A-3E, any modules or units (except the client device 300 and operators 320, 321, 701) can optionally be a part of the server system 200. Turning to FIG. 3A, for example, an exemplary diagram illustrating an alternative embodiment of the environment 100 is shown. The server system 200 can include a management system 220 for ontologies 230, models 210, and business/Medical/Legal Rules 227. The server system 200 can include a management web app 225. The environment 100 can include a data scientist (or medical domain expert or content editor) 321. The server system 200 can include a training system 240 that can be online and/or offline during operation. The training system 240 can include a model building pipeline 247 (detailed in FIG. 3B). The environment 100 can include an online app system (or a digital health information system) 265 that includes a database 267 containing user information and an app server 260. The ontologies (or ontology) 230 can be stored in one or more databases that organize ontology objects in selected structures.

The environment 100 can include one or more health care provider systems 700 each operated by a medical provider 701, such as physician, clinic admin, nurse or the like. The health care provider system 700 can include a doctor portal app server 280 and/or a doctor portal database 281.

Turning to FIG. 3B, a more detailed view of the training system 240 is shown. The training system 240 can include one or more integrated health records 250A. The integrated health records 250A can include structured data 251A (including, for example, age, gender, lab results, diagnosis, etc.), and unstructured data 252A (including, for example, text data such as doctor notes). Optionally, the training system 240 can include one or more integrated health records 250B that is from a source that is different from the source of the integrated health records 250A, and can include structured data 251B (similar to structured data 251A) and/or unstructured data 252B (similar to unstructured data 252A).

The model building pipeline 247 can include a model building module (or model training module) 212, a natural language processing (NLP) feature extraction module 270, a data cleaning module 290, clean medical records 291 and a trained model 210. The model building pipeline 247 can include structured data 271. The structured data 271 can include results generated by the NLP feature extraction module 270 that are combined with the structured data 251. The structured data 271 can generate case vectors for training the model 210 and/or be provided to a medical professional for analysis.

Figure 3C:
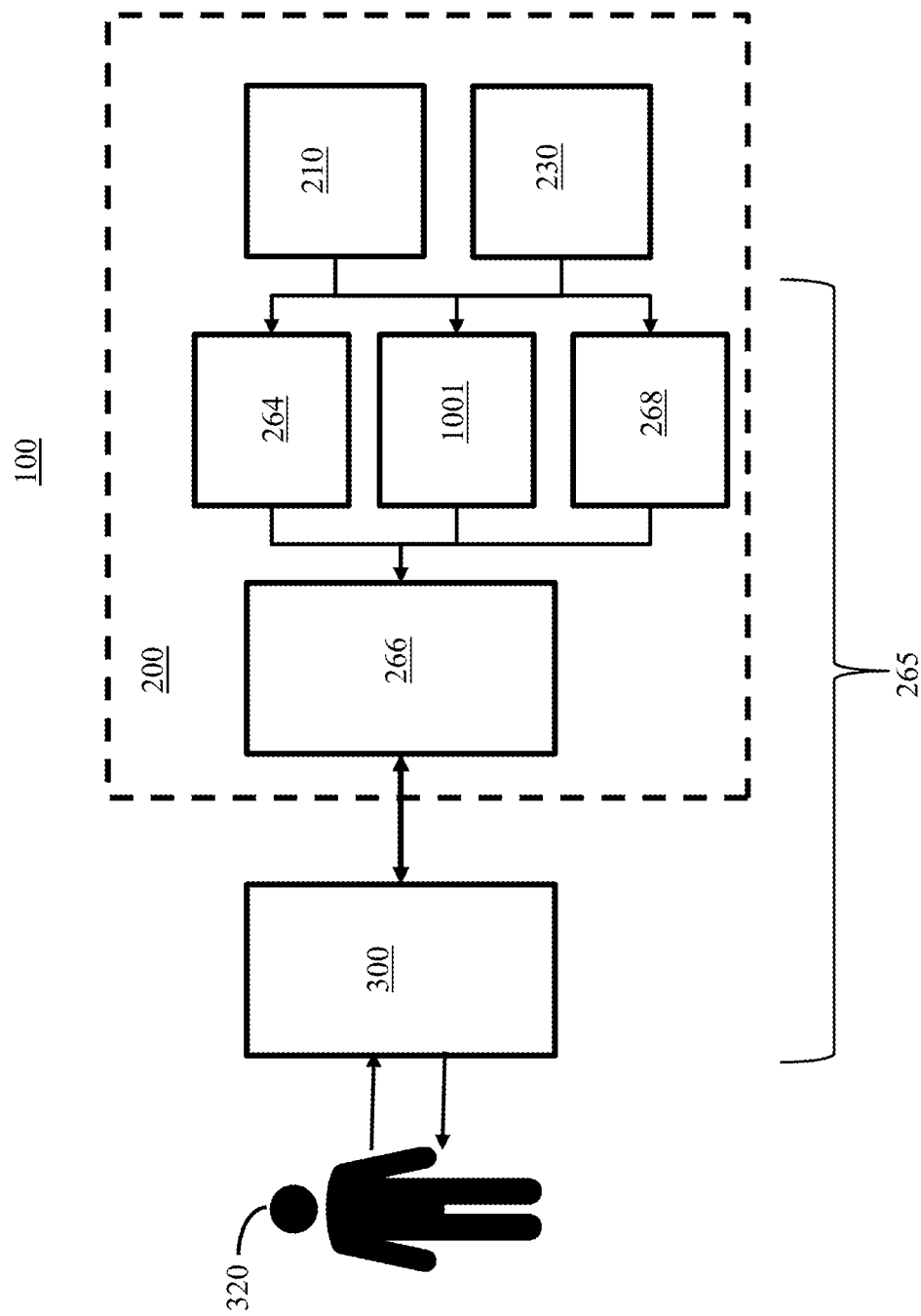
FIG. 3C is a diagram illustrating another exemplary embodiment of the server system of FIG. 1.

Turning to FIG. 3C, an exemplary diagram illustrating an alternative embodiment of the environment 100 is shown. The online digital health information system 265 can include the app server 266, the conversation engine 264, the reference population calculator 1001, and the classifier server 268. The reference population (also referred to as RP, PopuLation Matched (PLM)) can include a subset of medical cases in the population medical database. Reference population information can include any information about the reference population and/or a reference population index which can be, and/or be based on, a number of the feature vectors having one or more relevant symptoms and one or more relevant profile features that are in the current feature vector.

Figure 3D:
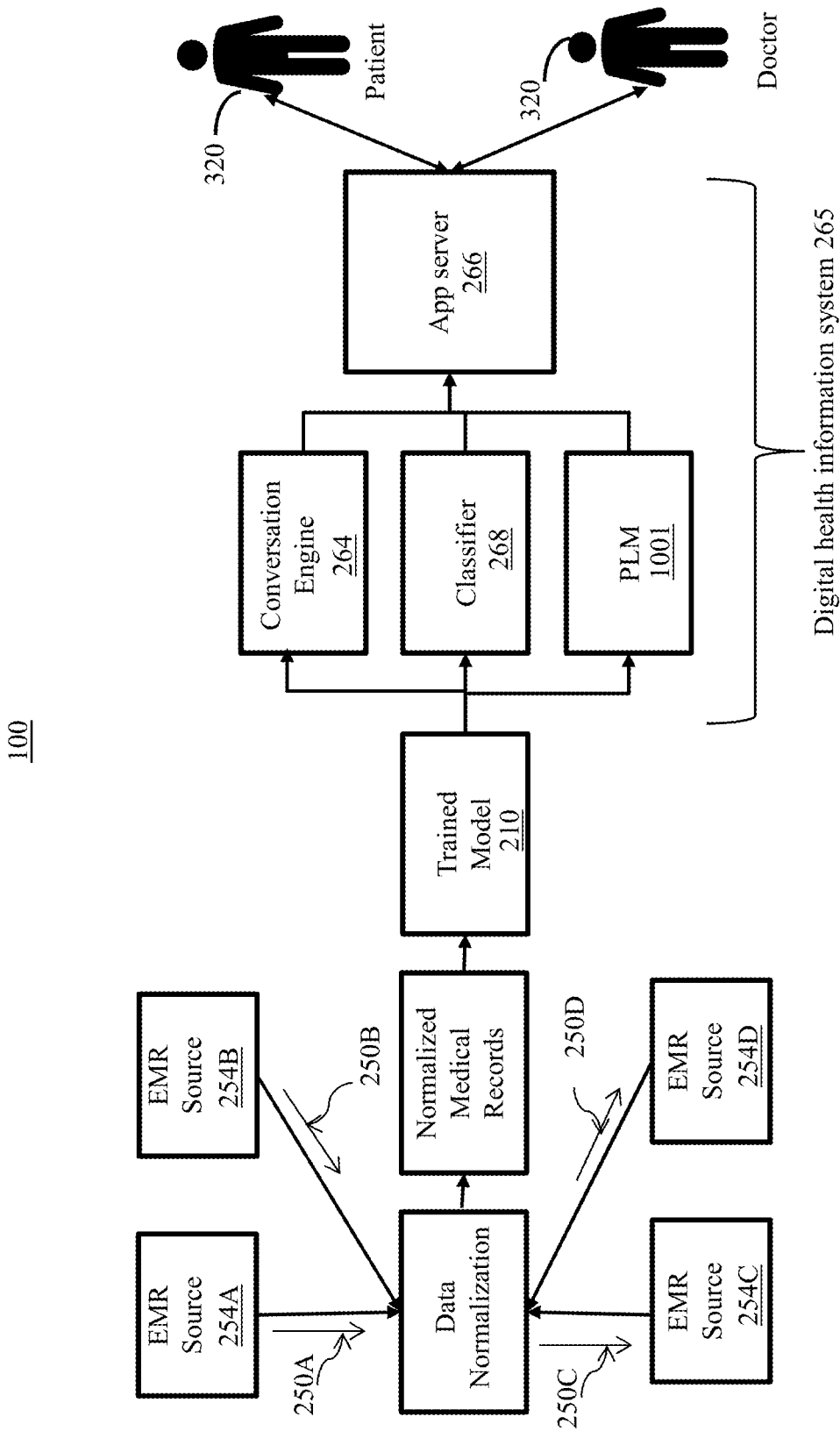
FIG. 3D is a diagram illustrating another exemplary embodiment of the server system of FIG. 1.

Turning to FIG. 3D, an exemplary diagram illustrating an alternative embodiment of the environment 100 is shown. Electronic medical record (EMR) 250A-250D, respectively from different sources 254A-254D, can be normalized to form normalized medical records for training the model 210. The model 210 can be used by the conversation engine 264, the reference population calculator 1001, and/or the classifier server 268. Output of the conversation engine 264, the reference population calculator 1001, and/or the classifier server 268 can be provided to the digital health information system 265 that interacts with the patient and/or doctor.

Figure 3E:
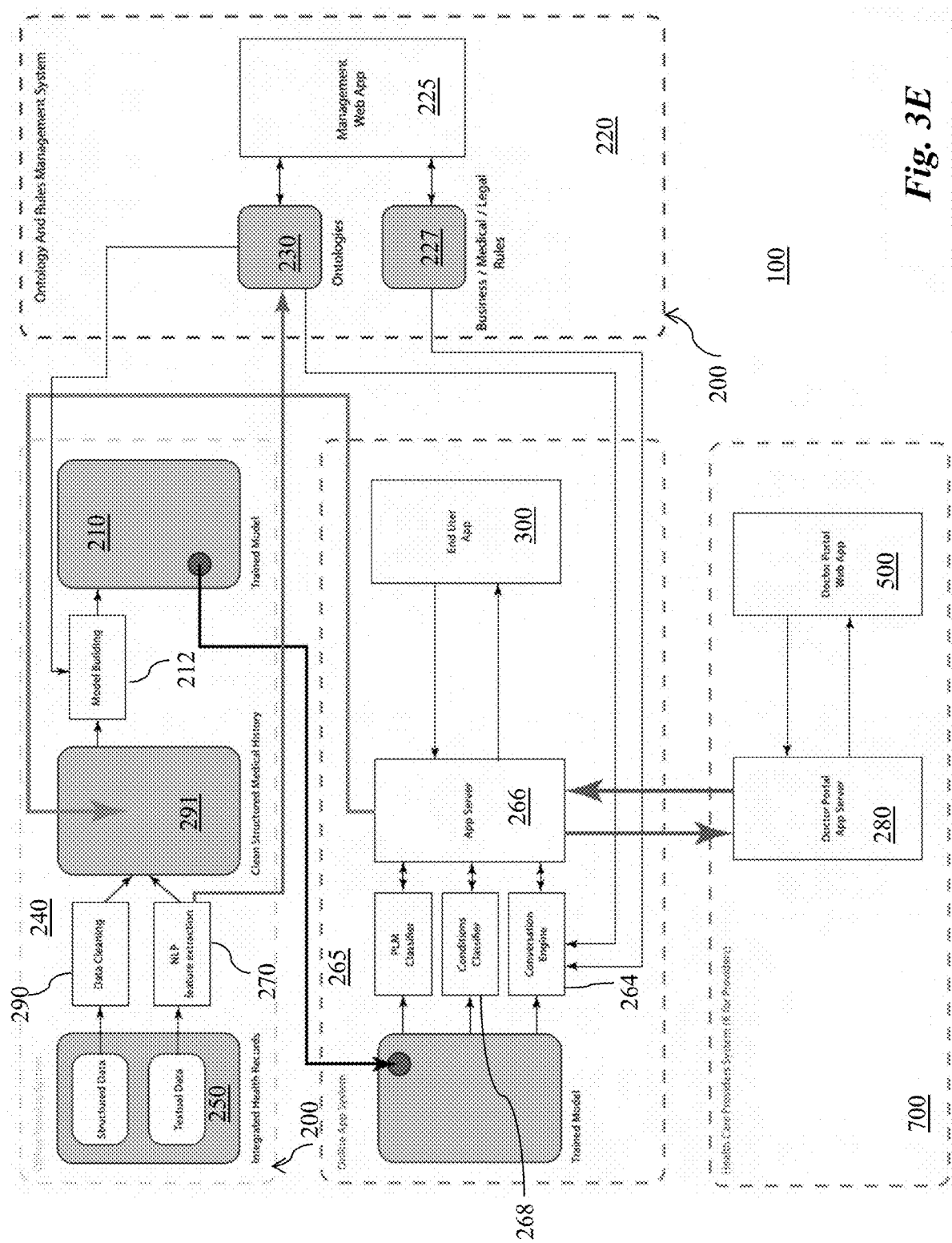
FIG. 3E is a diagram illustrating another exemplary embodiment of the server system of FIG. 1.

Turning to FIG. 3E, an exemplary diagram illustrating another alternative embodiment of the environment 100 depicts a more detailed view of the environment 100. The technical solution can include the following: ontology construction; medical records normalization; machine learning model training; health dialog creation using the model and ontology; display of various predicted results using the model; and digital health information system creation from the above and optionally other components.

A. Translation/Semantic Analysis/Data Mining of Doctor-Patient Medical Records.

The server system 200 selects medical visit records along with doctor's notes associated with the medical visit records to relate the medical visit records to a diagnosed condition. For example, the server system 200 can construct, per person in the server system 200, a timeline (or time line) of a "medical journey" based on a list of doctor visits, lab test results, medications taken, etc. ordered by date they took place.

The server system 200 can receive a large sample of doctor-patient notes covering thousands of different conditions. The server system 200 can tag the notes to establish a plurality of objects (or entities, items, or the like). These objects are used to establish an ontology (or Symptom-Attribute-Value (SAV) ontology) 230 that is of a large size and includes the plurality of objects established by tagging. For example, when applied to text notes relating about 200 common conditions, the server system 200 can construct an ontology with 15,000+ medical features. The SAV ontology 230 describes symptoms, their attribute, and all the possible values of all attributes. A particular case vector notes the symptom that is present in the case vector and the value of the attributes of those symptoms. Exemplary objects can include a symptom object, a condition object, a severity object, a time period object, an attribute object, a value object, and so on. The severity object and the time period object can each be an attribute object. Exemplary value objects for the severity object can include 'mild,' 'severe,' or 'awaking at night.' Exemplary value objects for the time period object can include 'one day,' 'one week,' etc. Additionally and/or alternatively, exemplary objects can include a negation object (e.g., representing a headache without dizziness), a link object (e.g., diarrhea after eating suspicious food), and/or other attributes of symptoms such as location and type (pulsating headache above the left ear), etc. Other examples of objects that can be part of the ontology 230 can include medication object, treatment object, and/or profile features (that is, the features that are not symptom, attribute or value, but that summarize the medical history or personal information). Each profile feature can be associated with a canonical name designated for each ontology object. Exemplary profile feature can refer to some characteristics of a person (such as gender, year of birth, etc), not related to a particular case.

In one embodiment, the condition object can be part of the ontology 230, not being a symptom object, an attribute object, or a value object. The negation object is not necessarily a unique object in the ontology 230, but can be used as an indicator for marking that an object (a symptom object, for example) is negative in a particular visit record. Such marking can be used for training the model 210.

These objects are used to establish an ontology (or Symptom-Attribute-Value (SAV) ontology) 230 of a large size. For example, when applied to text notes relating about 600 common conditions, the server system 200 can construct an ontology with 15,000+ medical features. The SAV ontology 230 describes symptoms, their attribute, and all the possible values of all attributes. A particular case vector can note the symptom that is present in the case vector and the value of the attributes of those symptoms.

In addition to storing the list of objects in the ontology 230, the server system 200 can maintain a graph structure that captures the relationships between the different objects. In addition, the server system 200 collects statistical metrics on the correlations between symptoms, attributes, and values to medical insights. The medical insight can include any medical conclusion and/or action that is an output of a medical case. Exemplary medical insights can include medical conditions and/or other medical aspects such as medications, treatments, lab tests ordered, lab test results, with and/or without gender, age, and other parameters.

As there are many potential Symptom-Attribute-Value (SAV) combinations that can result in a certain condition, artificial intelligence (AI) can be used to weigh the different likelihoods. The server system 200 can be taught the main language and use natural language processing (NLP) to run through millions of doctor-patient notes to start finding these entities in the text. For example, name entity recognition (NER) can be used. Given the complexity of healthcare (HC), a set of heuristic rules based on physician behavior can be used to increase the accuracy of the NER capture.

The process continues with model training. The server system 200 can create a mathematical and learning model that, given an input of SAV's, can provide an output of the most probable conditions (or prescribed medication, or lab test referral). The output of such model can be in the form of a probability vector 214 (shown in FIG. 12A) including a plurality of probabilities, each associated with a medical condition. At least part of the probability vector can be presented via the user interface 340 (shown in FIGS. 15 and 16). The model training is done using a large set of feature vectors and is done using any methods suitable for machine learning. Building such a machine learned model, requires a large number of data records for it to be accurate enough. Furthermore, the number of data records can be large enough to cover each condition the model is expected to predict. One of the challenges of building such models is making available enough medical records, especially for rare conditions. One advantage of the method as set forth herein, through the use of normalization and the SAV ontology, is its ability to combine medical records from different sources, including sources from different languages, thus overcoming this obstacle.

A feature vector can include a vector of features. The features can include symptoms, attributes, and/or values based on the responses received. The features can include profile features associated with the user account (for example, age, gender, medical history, etc.) that characterize a medical case (or a patient) and exist independently of the current symptoms, attributes and values.

B. Machine-Based Conversation Method

A medical conversation requires asking questions for different aims. The aims include quick evaluation of urgency, hypothesis validation, ruling out of rare but severe situations and more. In the realm of digital health, user experience needs to be considered, and how quickly the interaction should yield results and accessibility of the information also need to be considered. A significant advantage of the current invention is the ability to create a health information system that mimic, and even surpass, a typical patient-doctor conversation.

C. Storing User Data for Later Use

The server system 200 can capture the response 310 (shown in FIG. 1) and use the profile information of the user account, thereby eliminating the need to re-ask a question that the server system 200 already knows. That is, if the profile information or a response 310 of a prior health conversion indicates that the patient smokes, the server system 200 does not need to seek input on whether the patient smoke in later health conversations.

D. The User Interface 340 can Visually Present Questions and/or Results

The user interface 340 (for example, shown in FIGS. 14-18 and 21-32) can emulate a typical physician-patient dialogue. Additional and/or alternative user interfaces can be provided where a feature vector is constructed from free text input in both offline or during an active conversation (on line), or from forms filled by physicians, etc. In one example, the free text input can include responses to questions in the health conversation 262 (shown in FIG. 5A). In another example, the free text input can include text input not based on a question based on a specified symptom, profile feature or attribute, but instead generated in a free form by the operator 320 (such as a patient or doctor). Exemplary free form can include one or more sentences or paragraphs, as in human narration, describing one or more symptoms, one or more attributes, medical history, profile features, or a combination thereof.

E. User Interface.

The client device 300 can provide a user interface that looks and feels differently from interfaces provided by conventional systems. The user interface 340 (for example, shown in FIGS. 14-18 and 21-32) can emulate a typical physician-patient dialogue. In contrast with conventional systems, the user interface 340 can include pictures, icons, graphs (e.g., pie chart with medication), and/or other features.

Additionally and/or alternatively, the server system 200 can include professional care-giver facing modules. Such modules can include automatic case summary generation, communicating case details between different care givers, communication between care giver and patient, digital prescription of medications, lab test referrals, communication between patient and doctor that interacting into two different languages, etc. Furthermore, as the system is based on large amount of medical records, it can present to the doctor, multiple statistics, such as how past doctors handle similar situations, graphs showing development of conditions in large population, and similar other information to help them in deciding on the correct course of action with the current case.

The server system 200 can advantageously create a normalized 'clean' dataset from doctor notes, possibly coming from different sources, using a canonical ontology. Different sources can include multiple records related to a particular person that are stored in different systems (clinic computer, hospital computer, radiology lab system, etc.). The different sources can include different sources related to different populations. For example, some records can be originated from one hospital or clinic for population A, and another set of records related to population B can come for a different hospital or clinic using a different database or software system for keeping those records. Furthermore, the different sources can contain notes in different languages. In some embodiments, creating a clean normalized dataset includes: (1) having a common ontology used for normalizing the medical data in the various medical records; (2) extracting the medical information from textual notes included in medical records; (3) being able to perform such operations on a very large number of medical records from one or more sources; and (4) generating normalized data capturing medical records in the form of case feature vectors that can be used for training machine learning models. The creation of such structured data can generate a general framework for many decision support tools to clinicians. An exemplary application can include producing a doctor visit summary.

Training the model 210 requires many records for the model 210 to be accurate, and acquiring a large number of records, especially for rare conditions is a challenge. Using the SAV ontology, and normalizing data from multiple sources using the ontology, allows the use of sources in different languages, hence overcoming this challenge.

Additionally, having the common ontology 230 allows the easy translation programs of the server system 200 (shown in FIG. 1) to different languages and the communication of health issues between a patient speaking one language and a doctor speaking a different language.

In one embodiment, the server system 200 performs a plurality of following steps 1-31. Some of the steps can be optional. Additionally, these steps do not need to be performed in this particular order as desired.

1. Using different sources of electronic medical records (or population medical database, or integrated health records) 250.
2. Performing, by using a data cleaning module 290 (shown in FIG. 3B), various data cleaning operations on the structured parts of the data, such as:
   a. Removing records with no conclusive or relevant information
   b. Removing noisy records
3. Performing automated NLP based feature extraction from the textual parts of the data, such as:
   a. Doctor visit notes and summary
   b. Hospital discharge summary
4. Building and using an initial tagging graphical user interface (GUI) for initial tagging of medical texts with hierarchical SAV ontology objects, and expressing negations, and relations between parts of sentences. The initial tagging can be performed manually (optionally) or automatically.
5. Building, as part of the NLP feature extraction mechanism, an ontology 230 of SAV objects used to describe a medical case.
6. Constructing the extracted features from textual information in a hierarchical SAV structure.
7. Building, as part of NLP and/or manually, ontologies 230 for describing demographic, medical history, lab tests, medications to standardize all features of a person/medical case.
8. Combining such ontologies 230 with industry standard ontologies (such as medications).
9. Performing model building using a model building module (or model training module) 212 (shown in FIG. 3B) on the "clean structured medical history" data. Model building can use various "Machine Learning" or "Deep Learning" methods, for example. Model building may use:
   a. the SAV feature structure
   b. time attributes of the records
   c. demographic data (e.g., gender, age, district, etc.)
   d. medical history (e.g., past surgeries, chronic conditions, family history of diseases)
   e. lifestyle information (e.g., smoking, drinking, diet, etc.)
   f. measurements (e.g., blood pressure, weight, height, heart rate, etc.)
   g. medication use
   h. lab test results
   i. genetic markers
10. Using a health predictive model 210 in an online system serving end-users using a mobile app or website interface. The health predictive model 210 can include a model that determines possible medical conditions.

Stated somewhat differently, the health predictive model 210 can predict possible medical conditions that a patient may be having.

Figure 37:
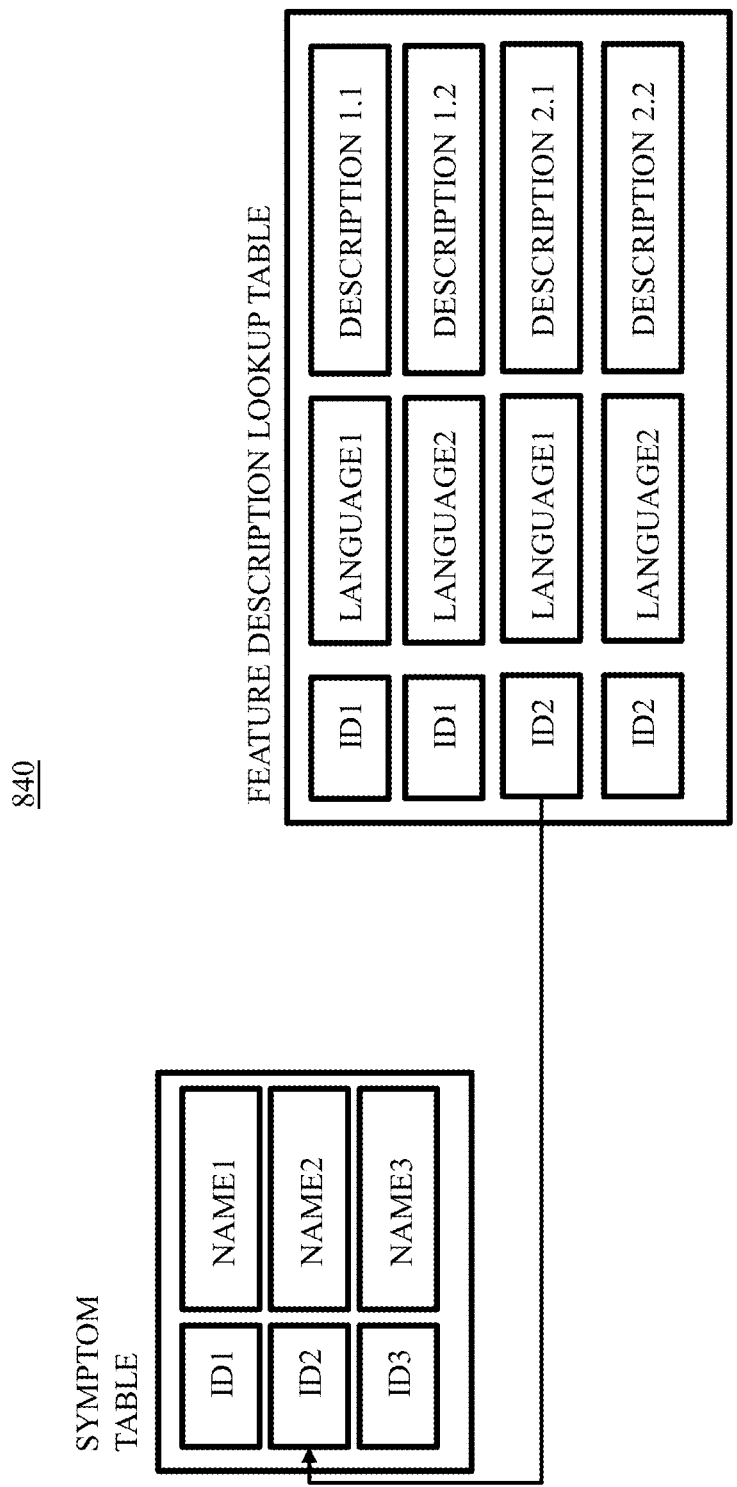
FIG. 37 is a diagram illustrating an exemplary embodiment of a summary text database constructed by the server system of FIG. 1.

11. Using the constructed SAV ontology to build the conversation with the end user around their symptoms (e.g., Do you have a headache?), attributes of symptoms (e.g., how long do you have this headache?) and values (e.g., for 3 days).
12. Applying calculation (e.g., using Equation(1)) on the trained model to use it to extract a relevant sub model based on a reference population. The concept of reference population can be dynamic and based on both demographic information as well as particular combination of current symptoms, past medical history, medications taken, lab results, etc.
13. Predicting possible conditions based on user demographic, medical history, current symptoms and their attributes.
14. Predicting possible other medical insights or actions, such as the most probable lab test, or most probable medication used in similar cases.
15. Applying, via a conversation engine (or conversation manager) 264 (shown in FIG. 3C) to manage a health conversation 262 (shown in FIG. 5A) with the end user. The conversation engine 264 can include a computer implemented program that is configured to choose the most appropriate next question to ask the user based on both the trained model, as well as set of business rules, domain rules and legal constraints.
16. Employing a management system (or management application, or management web application) 225 to correct automatically created ontologies 230 (for example, removing certain symptoms, ignoring certain attributes, or defining two values as similar). In one embodiment, the management system 225 can be operated by a human operator and be configured to control some aspects of the ontologies 230, and some aspects of the health conversation 262 (shown in FIG. 5A).
17. Employing a management system 227 to apply additional medical rules to affect the interaction with the user. Example for such rules can include defining certain symptoms as non-applicable for certain gender or age group (e.g., females do not have scrotal pain, and females over 65 are not expected to be pregnant).
18. Employing the management system 227 to apply additional business/legal rules to affect the interaction with the user. Example for such rules: flag certain symptoms as triggering "red flag" alerts, or requiring additional lab tests, ECG tests, etc.
19. Using data gathered by app server 266 from the app users to feed back the "Clean Structured Medical History" dataset to be used in training future model versions.
20. Performing outcome analysis both on historical data in a Clean Structured Medical History repository 248, and/or via an in-life "closed loop" between the app recommendation and verified doctor diagnosis and treatment information obtained from end-users.
21. Allowing the users to connect to care providers to receive further help
22. Allowing users to send a "health conversation" to a health provider
23. Creating a summary of a "health conversation" a user took in the app for a health care provider to quickly assess the case. A possible implementation presented as an example is producing a summary text by going over a feature vector to obtain a features subset that is selected and ordered by a table of feature identifiers (such as a symptom table in a summary text database 840 shown in FIG. 37, wherein attribute table and value table can be similarly included). For each feature, textual representation of a summary text for the doctor can be generated by using a feature description lookup-table, as detailed in Table 1.

TABLE 1

| Line | Instruction |
| --- | --- |
| 1 | Read list of feature names from database into FNL |
| 2 | Read summary look up table from database into LUT |
| 3 | {SV} ← user case vector |
| 4 | Summary ← empty string |
| 5 | For each fn in FNL do: |
| 6 |   If {SV} contain fn: |
| 7 |     Str ← LUT[fn] |
| 8 |     Summary ← Summary + REPLACE (STR, {"placehoder", SV}[fn]) |

24. Allowing creation of a case summary in a different language, by (for example) using a different lookup table in the method described in Table 1 that uses strings in a different language.
25. Allowing care provider to respond back to user with simple options (for example: stay home, sending you a prescription, ordered a lab test, go to the emergency room (ER)).
26. Present to the health care provider the application prediction model results, and optionally other information on the current case and similar cases considered in the model building, to help them make better medical decisions.
27. Presenting the health care provider with the application prediction model results, and giving them a simple way to mark the accuracy of the health predictive model 210 and to input their own diagnosis and treatment (hence creating "closed loop" data for improving the health predictive model 210)
28. Perform outcome analysis on health providers "closed loop" data
29. Providing a way to collect certain metrics, especially related to chronic disease management (for example blood pressure readings for people suffering Hypertension)
30. Using those metrics as part of the health predictive model 210.
31. Using metrics collected by chronic patients to perform anomaly detection and early alert of the need to see a doctor when a trend is detected.

In another embodiment, the method can include a plurality of steps. Some of the steps can be optional. Similarly, the steps do not need to be performed in any specific order.

Figure 35:
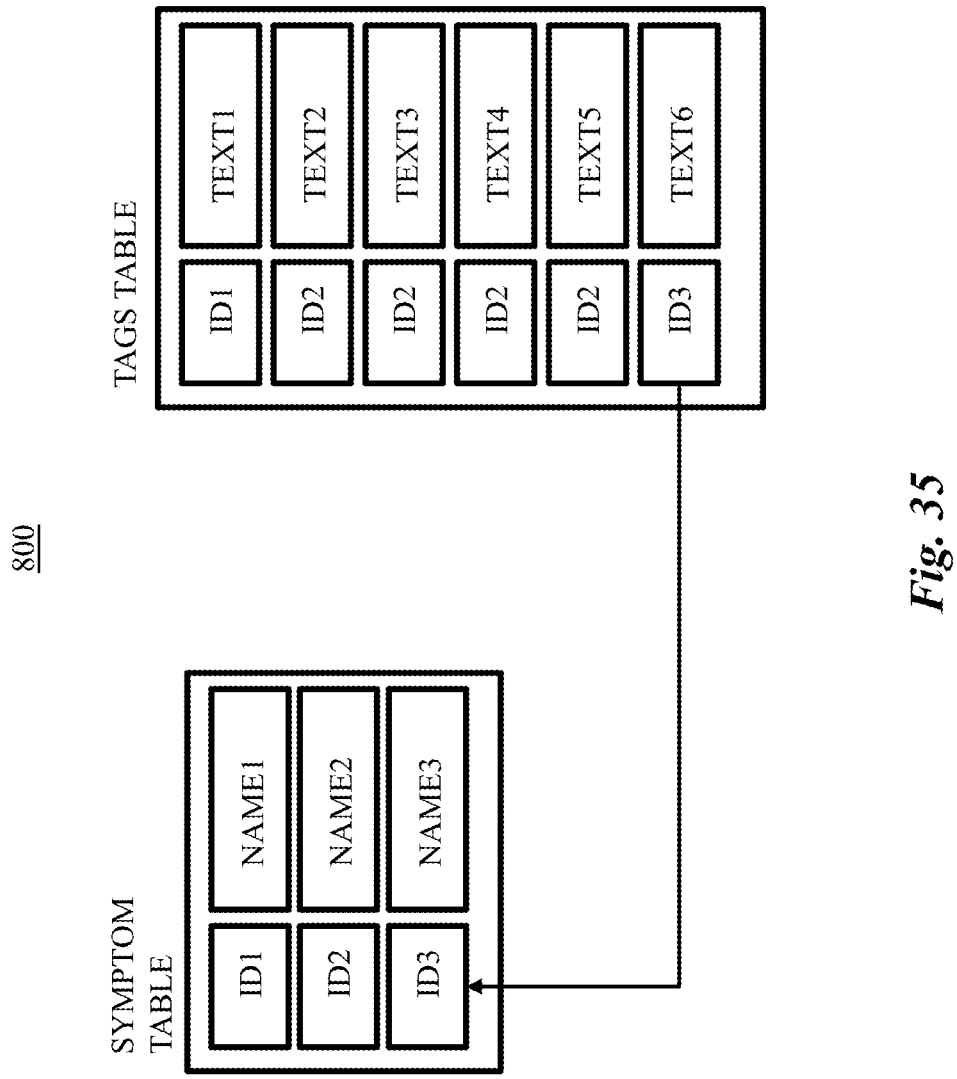
FIG. 35 is a diagram illustrating an exemplary embodiment of a tag database constructed by the server system of FIG. 1.

1. Using different sources of electronic medical records. These sources can include both unstructured, free text information as well as structured, or coded information, such as (but not limited to):
   a. Doctor appointment notes in free text capturing patient complaints, doctor examination and observations
   b. Doctor visit summary diagnosis (e.g., represented as coded International Classification of Diseases 10 (ICD10), or other coding)
   c. Demographic data
   d. Past medical history (e.g., known conditions—High blood pressure, diabetes, etc.)
   e. Hospital discharge notes f. Lab test results—such as blood count, urine
g. Medications prescribed and purchases
h. Imaging test notes (free text)
2. Performing various data cleaning operations, such as:
   a. Removing records with no conclusive or relevant information. For example, dropping visit summaries where the visit has no single conclusive acute diagnosis.
   b. Removing noisy records—for example, removing repeat visits (such as a second visit of the same case) or dropping records where the amount of doctor text is below a threshold (or above a threshold).
   c. Removing records written by doctors with lower rating.
      i. Doctor rating is calculated based on good clinical practice evaluation
      ii. How descriptive their summary text is—this is estimated by several selected processes. For example, an average note length of a doctor can be compared to the average note length of the general population of doctors. In another example, an average number of ontology objects extracted from notes by a doctor can be compared to that of the other doctors. Additionally, and/or alternatively, domain knowledge can be used to analyze the notes based on the diagnosis tied to the notes to determine whether the notes are sufficiently descriptive. For example, a diagnosis of a complex condition is expected to have more descriptive text and/or refer to more symptoms or other objects.
3. Performing automated NLP based feature extraction (for example, named entity extraction) using medical ontology to provide the entity space from the textual parts of the data, such as:
   a. Doctor visit notes and summary
   b. Hospital discharge summary
4. Above named entity extraction is comprised of:
   a. Using pre-tagged medical texts with hierarchical SAV ontology objects, and expressing negations, and relations between parts of sentences. Such tagging is performed on a representative subset of the text records. Such tagging will result in a tag database 800 (shown in FIG. 35 and being optionally part of the server system 200) for storing a list of possible tags, or strings linked to the different SAV entities. Two possible ways to tag text are:
      i. Tagging could be human labeling of specific words in the text itself, from which a hierarchical SAV ontology can be constructed along sample case or visit vectors.
      ii. Tagging can be achieved by using the structured (non-textual) fields in the electronic medical records accompanying the text, as contextual labels for the texts. For example, with this approach, the SAV of a diabetic patient can be learned by associating with patients that had high levels of Hemoglobin HbA1c or patients that were prescribed with Insulin. Stated somewhat differently, even when a medical condition is not explicitly recorded in the medical notes, the server system 200 can identify that the current patient has a specific medical condition via the structured fields (e.g., lab test). The server system 200 can use the SAV objects from data of other patients with the same medical condition to find the SAV objects to extract for the current patient.
   b. Building, from the tagged examples, an ontology of symptoms (e.g., headache, abdominal pain), their attribute (e.g., severity, when did it start, where does it hurt, etc.) and the attribute values (severity=severe, started 3 days ago, etc.)
   c. Automatically applying named entity extraction on non-tagged text notes, applying several NLP algorithms such as semantic and phrase analysis, edit distance matching to the ontology objects to extract the ontology objects from the non-tagged texts generating feature vectors per user visit.
5. Building, as part of NLP and/or manually, ontologies for describing demographic, medical history, lab tests, medications to standardize all features of a person/medical case.
6. Combining such ontologies with industry standard ontologies (for example, medications based on Anatomical Therapeutic Chemical (ATC), National Drug Code (NDC), and RxNORM).
7. Translating such ontologies, and their corresponding tag vectors to be easily used in extraction of SAV values into case vectors from doctor notes in different languages.
8. Combining feature vector coming from above NLP process with other structured data to create a set of "normalized, clean medical records"
9. Performing model building on the "clean medical records" data. Model building can use various "Machine Learning" or "Deep Learning" algorithms used in the field of algorithm development or machine learning. Model building may use some parts of the clean medical records data as the feature vector for model training, such as:
   a. the SAV feature structure
   b. time attributes of the records
   c. demographic data (e.g., gender, age, district, etc.)
   d. medical history (e.g., past surgeries, chronic conditions, family history of diseases)
   e. lifestyle information (e.g., smoking, drinking, diet, etc.)
   f. social network data
   g. measurements (e.g., blood pressure, weight, height, heart rate, etc.)
   h. wearable sensors data
   i. medication use
   j. lab test results
   k. genetic markers
10. Model building is done by taking feature vectors (a vector per one patient case) where the vectors are known to have a certain diagnosis (encoded, for example, by the Doctor as ICD10 in the visit record), using the diagnosis (or any medical insight) as a category label, and applying one or more of common machine learning algorithms to train a model. Such algorithms can be of statistical, connected neural networks, and/or any other suitable methods. Non-limiting examples of such machine learning algorithms are: Naïve Bayes, Random Forest, Fully-connected neural network, convolutional neural network, Bayesian model, Bayesian Network, logistic regression, and others as well as combinations of them.
11. Selecting the best model either by running an evaluation before deploying the model or by actually using multiple models in parallel on the live system and applying some voting algorithm to pick the result 12. Using the produced "Trained Model" in an online system serving end-users using a mobile app or website interface
13. Using the constructed SAV ontology to build the conversation with the end user around their symptoms (example: Do you have a headache?), attributes of symptoms (example: how long do you have this headache?) and values (example: for 3 days).
14. Applying further algorithms on the trained model to use it to extract a relevant sub model based on reference population—where the concept of the reference population is dynamic and based on both demographic information as well as particular combination of current symptoms, past medical history, medications taken, lab results, etc.
15. Applying calculation (e.g., using Equation(1)) using the current state of the conversation and cumulated feature vector to display a number or estimated number of the feature vectors in the reference population whose data is used to provide the results.
16. Applying an algorithm to predict possible conditions based on user demographic, medical history, current symptoms and their attributes
17. Applying a dynamic algorithm to manage the conversation with the end user, choosing the most appropriate next question to ask the user based on both the trained model, as well as set of business rules, domain rules and legal constraints.
    a. Such algorithm for selecting the next question may use a measure of entropy to select the question that will contribute the most to entropy reduction
18. Employing a management system 225 to correct automatically created ontologies (for example, removing certain symptoms, ignoring certain attributes, or defining two values as similar).
19. Employing a management system 227 to apply additional medical rules to affect the interaction with the user. Example for such rules: define certain symptoms as non applicable for certain gender or age group (e.g., females do not have scrotal pain, and females over 65 are not expected to be pregnant).
20. Employing a management system 227 to apply additional business/legal rules to affect the interaction with the user. Example for such rules can include flagging certain symptoms as triggering "red flag" alerts, or requiring additional lab tests, ECG tests, etc.
21. Using data gathered by app server from the app users to feed back the "Clean Structured Medical History" dataset to be used in training future model versions.
22. Performing outcome analysis both on historical data in the "Clean Structured Medical History" repository as well as in-life "closed loop" between the app recommendation and verified doctor diagnosis and treatment information obtained from end-users.
23. Allowing the users to connect to care providers to receive further help
24. Allowing users to send a "health conversation" to a health provider
25. Creating a summary of a "health conversation" a user took in the app for a health care provider to quickly assess the case
26. Allowing care provider to respond back to user with simple options (for example: stay home, sending you a prescription, ordered a lab test, go to ER)
27. Present to the health care provider the application prediction model results, and giving them a simple way to mark the accuracy of the health predictive model 210 and to input their own diagnosis and treatment (hence creating "closed loop" data for improving the health predictive model 210)
28. Perform outcome analysis on health providers "closed loop" data
29. Providing a way to collect certain metrics, especially related to chronic disease management (e.g., blood pressure readings for people suffering Hypertension)
30. Using those metrics as part of the health predictive model 210.
31. Using metrics collected by chronic patients to perform anomaly detection and early alert of the need to see a doctor when a trend is detected.
32. Performing clustering algorithms to find patients similar to the particular user of the system to provide information relevant to that user. For example: information on treatment and balancing chronic conditions.

Figure 4:
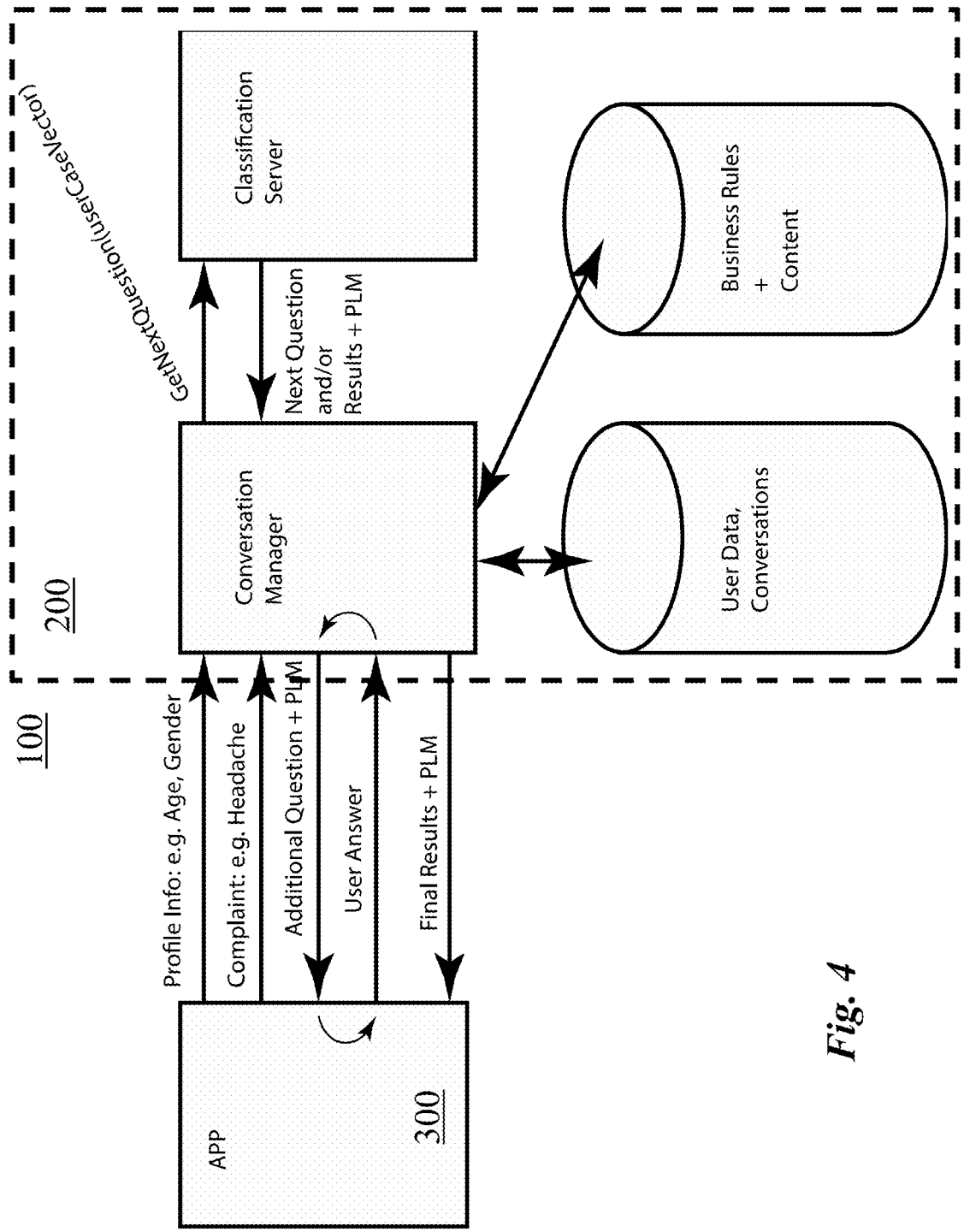
FIG. 4 is a diagram illustrating another exemplary embodiment of the server system.

Turning to FIG. 4, a more detailed view of the environment 100 is shown, wherein information exchange between the client device 300 and the server system 200 is shown. The information exchange can be at least partially implemented via a health conversation (or health dialog) 262 (shown in FIG. 5A)

The environment 100 as described automatically generates a health dialogue with a human user through a mobile device, desktop device, web, or an app operating on an electronic device with voice-based hardware configured for voice input. The health dialogue can be driven by an algorithm, where that algorithm itself is derived from extracting a medical ontology from free text doctor notes, and where the algorithm presents the most appropriate question at each stage, and finally provides the user with personalized health information that can assist them to get the best decision on their medical condition (or disease).

Figure 5A:
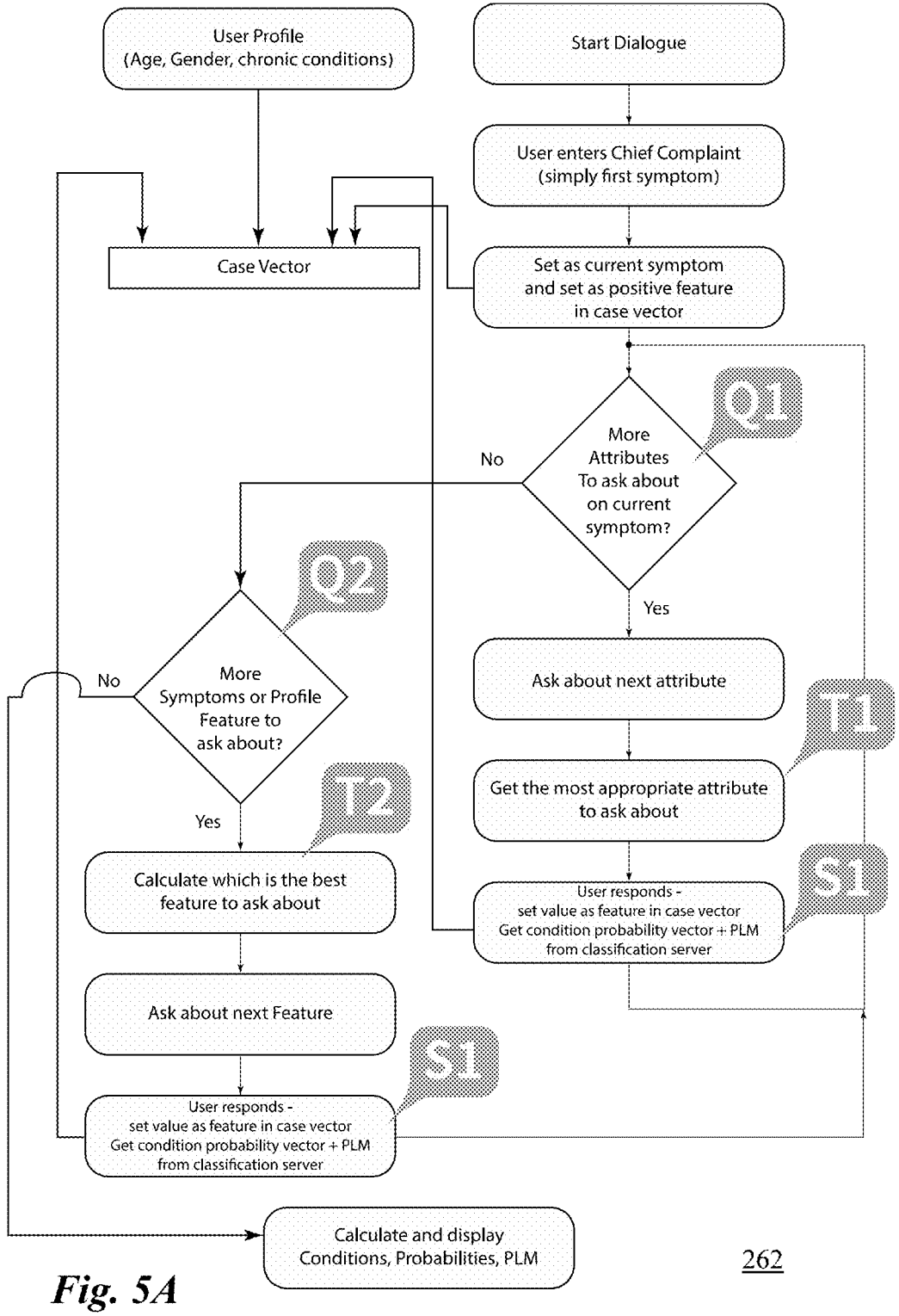
FIG. 5A is a flow diagram illustrating an exemplary method for management of a health conversation using the server system of FIG. 1.
Figure 5B:
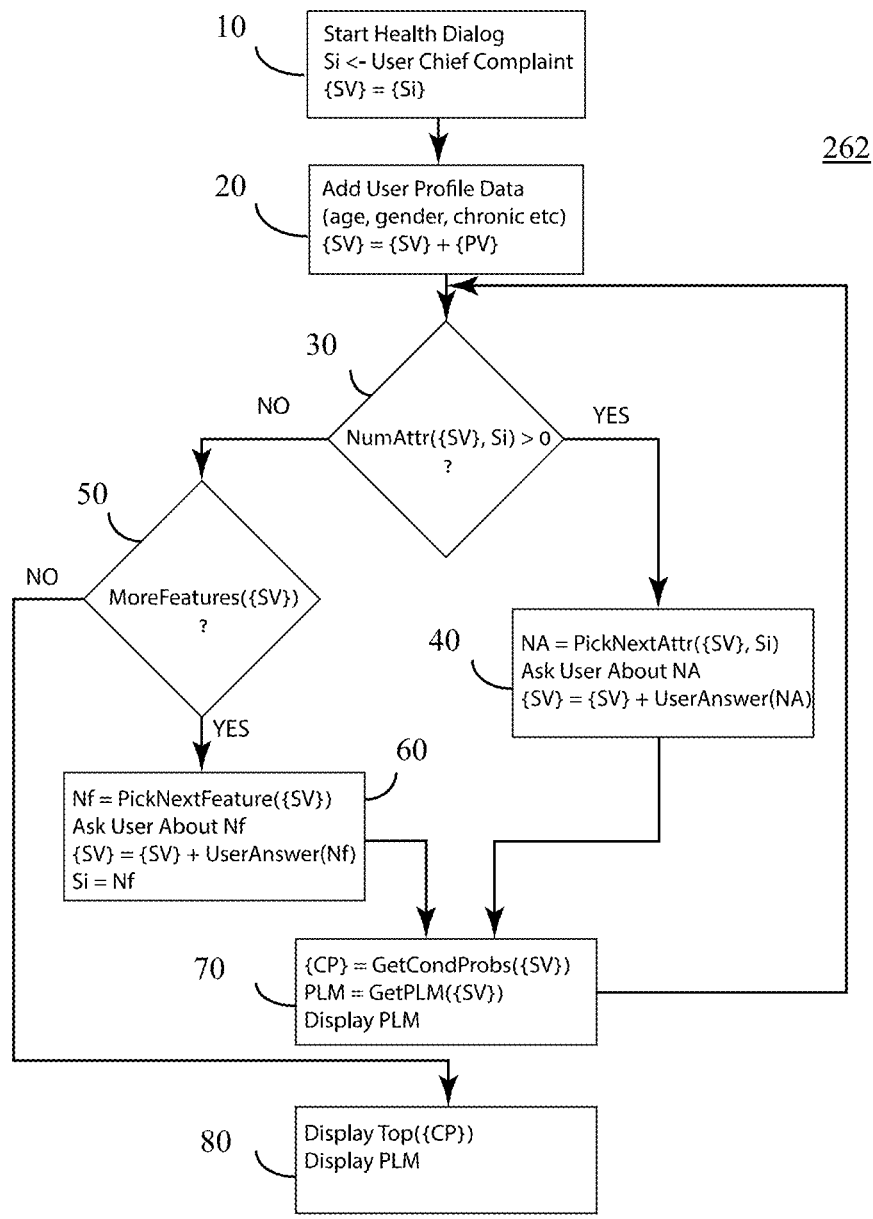
FIG. 5B is a flow diagram illustrating another exemplary method for management of a health conversation by the server system of FIG. 1.

Turning to FIGS. 5A and 5B, high-level flow diagrams of embodiments of a health conversation 262 is shown. Unlike traditional dialogue systems that go down a "decision tree"-like structure or try to fill in some "frames", the dialogue generated by the environment 100 (shown in FIG. 1) is more dynamic and adopts itself to the particular user (e.g., in terms of age, gender, past medical history, and answers to previous questions in the dialogue itself). The dialogue is optimized locally to ask the best question at each stage—best question being the question that will drive the conversation towards a more certain prediction of the possible condition the user suffers from. At the same time, the dialogue is globally optimized to be of the shortest length in terms of number of questions.

The Conversation Manager 264 (shown in FIG. 3C) is the part of the server system 200 (shown in FIG. 1) that manages the conversation with the user, taking into consideration user information, classification results based on the current user vector (or feature vector, or state vector) 224 (defined and explained later, in FIG. 10, for example), and applies a set of business rules and content to create a user friendly, logical dialogue.

Table 1 shows exemplary pseudo-code for managing the health conversation 262.

TABLE 1

| Line | Instruction | | | |
|---|---|---|---|---|
| 1 | User starts the dialog by selecting a symptom (as their chief complaint) | | | |
| 2 | Initiate the user state vector {SV}, with the chief complaint (SymptomS$_0$) as its only element | | | |
| 3 | Initiate a list of good medical practice rules (GMPlist) from database | | | |
| 4 | NumQuestions ← 0 | | | |
| 5 | MAIN_ITERATION: | | | |
| | a. | Call CalculateRP ({SV}) and display reference population Index | | |
| | b. | IF (size (GMP$_{list}$) > 0) | | |
| | | i. | Go over items in GMP$_{list}$ | |
| | | ii. | If GMP$_{list}$[i] is relevant to current {SV}: | |
| | | | 1. | NextQuestion ← question for GMP$_{list}$ [i] |
| | | | 2. | Remove GMP$_{list}$ [i] from GMP$_{list}$ |
| | | | 3. | Goto NQ |
| | c. | IF NurrQuestions > MaxSymQuestions | | |
| | | i. | Go To END | |
| 6 | d. | NextQuestion ← GetNextQuestion({SV}) | | |
| | NQ: | | | |
| 7 | | Present the user with NextQuestion a. | | |
| 8 | {SV} = {SV} + user answer (can be a symptom - S$_i$, or symptom attribute value s$_i$(a$_j$)) | | | |
| 9 | Goto MAIN_ITERATION | | | |
| | END: | | | |
| | a. | Calculate ConditionsProbabilities({SV}) | | |
| | b. | Display Conditions whose probability > CondProbThresh | | |

Figure 36:
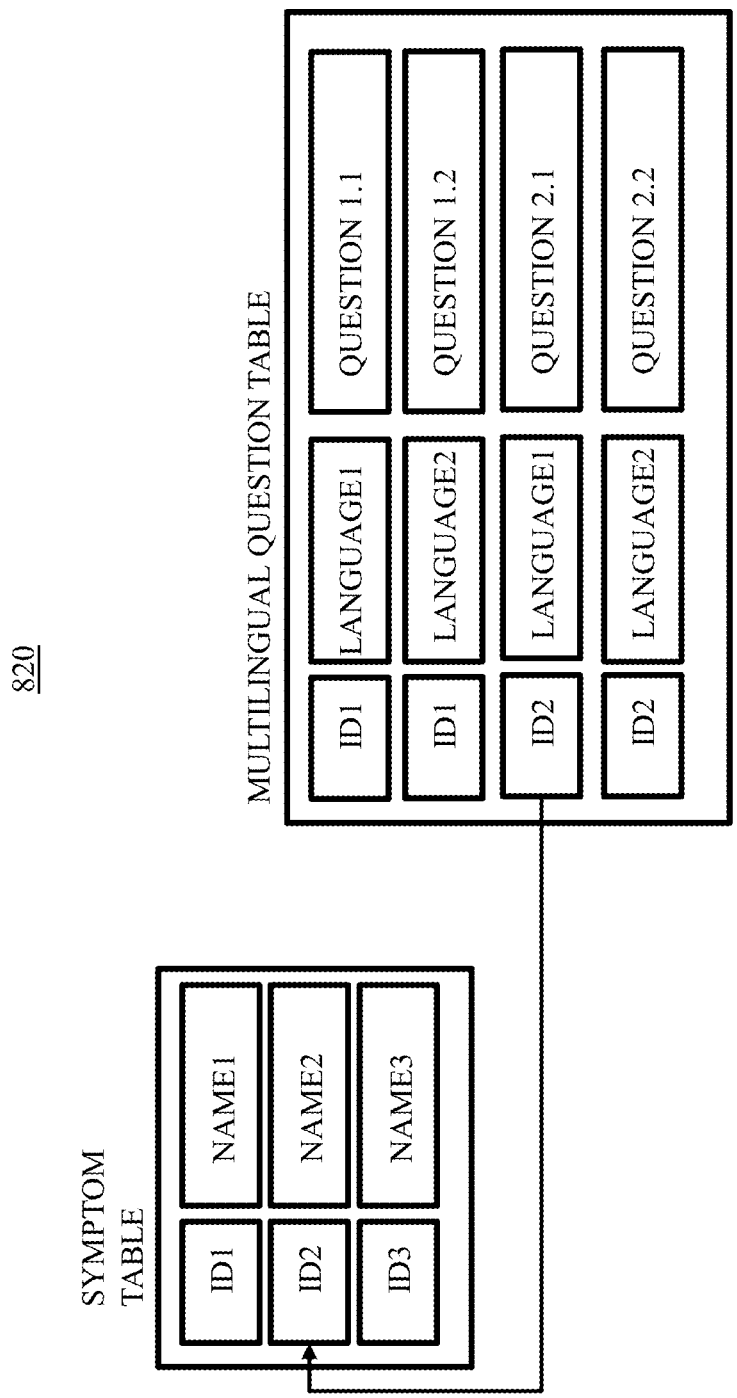
FIG. 36 is a diagram illustrating an exemplary embodiment of a translation database constructed by the server system of FIG. 1.
Figure 38:
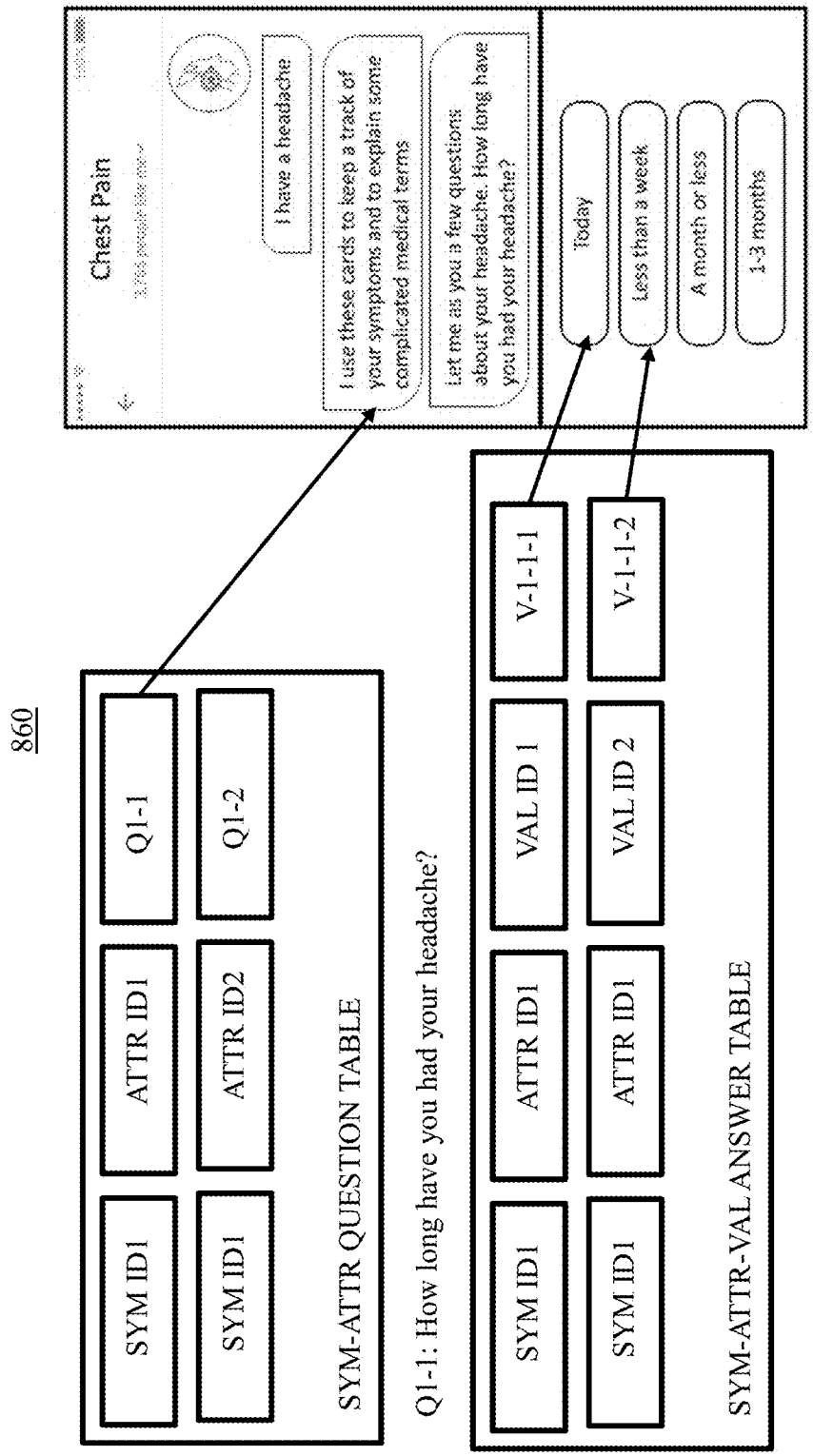
FIG. 38 is a diagram illustrating an exemplary embodiment of a question-answer database constructed by the server system of FIG. 1.

In Table 2, the function CalculateRP is for calculating a reference population index. The function GetNextQuestion are for determining the next question to ask, similar to PickNextAttr inside block 40 (or T1 shown in FIG. 5A) and/or PickNextFeature in block 60 (or T2 shown in FIG. 5A). Although Table 2 shows GetNextQuestion as being based on good medical practice rules, GetNextQuestion can be based on any other methods of calculating the next question, without limitation. GetNextQuestion can return a symptom ID to ask about, or an attribute ID to ask about, or other questions such as asking the user for a profile feature ("Are you smoking?"). The function ConditionsProbabilities is the calculation based on the health predictive model 210 (shown in FIG. 12A). NumQuestions is a function for counting the questions that have been asked. MaxSymQuestions is a function for providing a maximum number of questions. CondProbThresh is a function for providing a threshold probability value that can be predetermined. Line 6 of Table 2 above, which present the user with NextQuestion (NQ), can be further detailed by using a lookup table to translate the symptom ID to ask about, for example, via a translation database 820 as depicted in FIG. 36 and optionally being part of the server system 200, thus enabling the use of different question for different languages. Optionally, a question-answer database 860 (shown in FIG. 38) can be used for storing pre-formulated questions for asking about the attribute. The question-answer database 860 can store possible answers that match selections on a user interface such that input from the user interface can be structured data that can be more easily processed and added to the feature vector.

In FIG. 5B, certain steps can be detailed as described below.

The flow branch question NumAttr({SV}, Si) can be described as asking "are there more available attributes to ask about on current symptom, given the current case vector SV" (block 30 or Q1 shown in FIG. 5A), can include one or more of the following steps.

1. The block 30 can include a question "are there more attributes to this symptom in the ontology (have all possible attributes been asked)?" If not—it can be concluded that questioning can be finished.

2. The block 30 can include a question "are the remaining attributes allowed based on the current case vector and the business rules?" The business rules can include business rules based on the case vector (a), or on the conversation state (b) or a combination thereof.

(a) Business rule referring to case vector, for example: do not ask about severity of headache if user age is greater than 65.

(b) Business rule based on conversation state, for example: do not ask for more attributes on the current symptom if a certain number of attributes of the symptom have already been asked about.

The action "get the most appropriate attribute" (marked as PicknextAttr in block 40) can be implemented, for example, by one or a combination of the following.

1. PicknextAttr in the block 40 can include going over all remaining attributes, and finding maximal information gain, by (a)-(f) as following.

(a) Calculate the probabilities (or condition probabilities) given the current case vector, or current feature vector, that is established based on all information associated with the health conversation 262. The information can include symptoms, attributes, values based on the responses received, and profile features associated with the user account.

(b) For each possible attribute question, calculate the entropy of the set of conditions probabilities for each possible answer (in the case of yes/no it is one for a positive answer, one for a negative answer, for multi-choice attributes, it is a set for all possible values) where entropy (H) is defined as:

(c) $H = -\Sigma_{i=1}^{N} p(y_i) * \log_2(p(y_i))$ (d) Calculate effective entropy after question (in this example, a yes/no question) by multiplying the entropy given the probabilities after a positive answer, and the entropy given the probabilities after a negative answer, multiplying each by the probability in the general population of having the particular answer. Effective $H = H_{yes} * P(yes) + H_{no} * p(no)$.

To progress the dialogue with the user, the system wants to lower the entropy. The equation at (c) gives the entropy at a certain point in the conversation. When the change in entropy by asking a certain question is considered, the system wants to calculate what the entropy will be if the user answers the question with YES, and what it will be if they answer with NO. The probability of them answering it with YES is P(yes), and with NO is P(no). So the expected entropy is "Effective H". The effective entropy can be calculated for all possible questions, and the one that yields the lowest effective entropy can be selected.

(e) Find the question that will yield the lowest entropy (hence getting closer to certainty).

(f) Other methods may be used (such as Kullback Leibler (KL) divergence) to calculate "how far" the health conversion can progress by asking a certain question.

2. PicknextAttr in the block 40 can include finding the question who will yield the largest change in probability distribution or probability vector (not necessarily improve entropy). The change in the probability vector may be increasing or decreasing the actual information stored in that probability vector depending on conversational strategy.

For example, before asking a question X. the probabilities of having conditions A, B and C are 80%, 10% and 5%, respectively, and all other conditions are split for the remaining 5%. After asking the question X, if answered positively will make the probabilities of A, B and C be 35%, 30% and 25% respectively. Comparing the probability with question Y, the question Y can yield probabilities 82%, 8%, 5%. Thus, the question Y can yield a lower entropy, but the question X changes the distribution in a more radical way. Stated somewhat differently, the question X can be more significant in changing a diagnosis than question Y.

3. PicknextAttr in the block 40 can include picking the question for which the probability of a positive answer is the highest.

The question "More symptoms or profile features to ask" (denoted MoreFeatures in block 50 or Q2 shown in FIG. 5A) can be implemented as an example by:

1. Is a certain level of certainty reached in the prediction? The prediction is a set of probabilities for all possible conditions (Py for all Y), so certainty can be defined as the sum of the three most probable conditions being above X %. X % is a predetermined percentage value.

2. Have more than X questions been asked so far? This is a criterion for not making a too long conversation.

3. A combinations of (1) and (2), by calculating a Certainty×Length factor (that is, a factor equals to a product of certainty times number of questions) that gives a sense of "long enough conversation".

The action "Select the next feature to ask about" (PicknextFeature in block 60) can be implemented in a manner that is similar to selecting the next attribute to ask about. Stated somewhat differently, the next feature can be selected by calculating the change in entropy. For example, an answer to "Do you suffer from Symptom X" in itself can change the entropy even without answering any of its attribute questions.

Figure 5C:
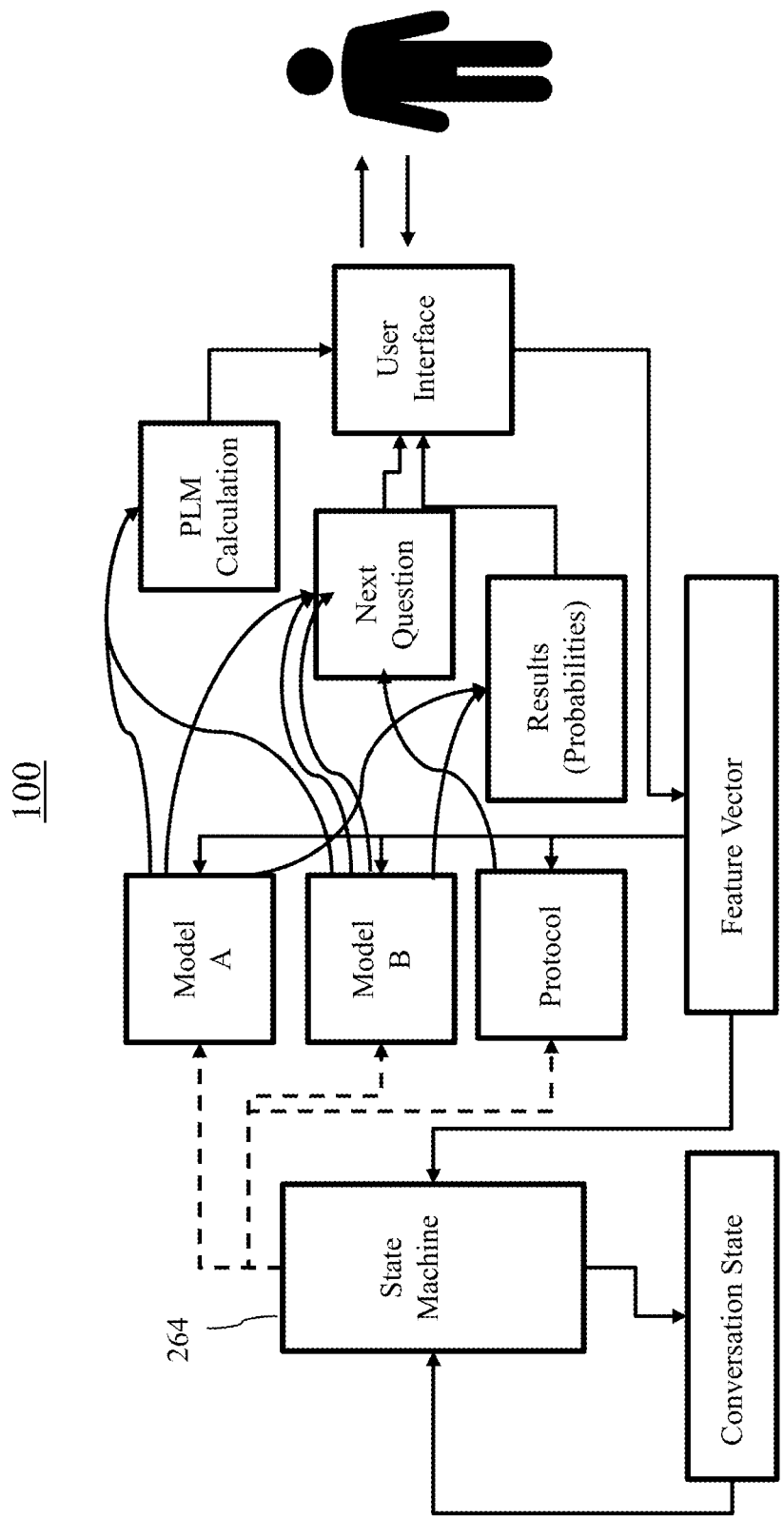
FIG. 5C is a diagram illustrating another exemplary embodiment of the environment of FIG. 1, wherein the server system implements a state machine.

Turning to FIG. 5C, a high-level diagram of another possible embodiment of a health conversation system is shown. In this embodiment, a state machine, driven from a conversation state, can select one of a plurality of models for calculating probabilities of possible outcomes (conditions for example), a reference population calculation, and a NextQuestion calculation. The Next Question can be calculated based on one of the models using a various of methods such as information gain maximization, or it can be selected using a protocol. The method used to calculate the next question can be selected by the state machine. Each answer from the end user is stored in the feature vector and is used along with the current conversation state to calculate the next state by the state machine.

In one embodiment, the conversation method allows the use of multiple conversation approaches and/or models. This is done by implementing the conversation engine 264 (shown in FIGS. 3C and 3D) as a state machine. At each stage of the conversation, a given approach is selected by the state machine. The conversation state maintained by the state machine includes the current feature vector that is populated from user information, and additional state relating to the progress of the dialog, the number of questions asked, and can be easily extended to include additional information (for example, considering past conversations with the same user). The state machine can select different approaches to picking the next question, as well as staying with the same approach, but switching the underlying machine learned model.

In a non-limiting example of different underlying machine learning (ML) models used, a model built using one machine learning technology that is more accurate for upper respiratory concerns can be used when the state machine detects that certain symptoms related to upper respiratory system are described by the user. In another non-limiting example, a model trained on data of a particular subset of the population may be used if the user falls into certain criteria that make them similar to that subset of the population. Non-limiting examples of possible different approaches include the following.

a) Selecting the next question that is most likely to be answered positively—using a predictive model learned from a large population of normalized data.

b) Selecting the next question that help cover the questions-probabilistic space, by maximizing an information gain measure (an entropy difference between two states as an example). To calculate the information gain, an underlying predictive model built from normalized data can be used.

c) A variant of the 'information gain' approach using different underlying predictive models or different measures of information gain. The information gain can be measured in more than one way. For example, the information gain can be measured based on an information difference and/or an information ratio. Information that is used for measuring that information gain can be calculated based on one or more probabilistic models (for example, regression, spline, and/or any other suitable models). Different probabilistic models and/or the underlying representation of probability vector space can change the final results of calculation of the information gain. The probabilistic models can be used for calculation related to the information gain (for example, calculating the probability in the expression for entropy H). Different probabilistic models can have multiple representations and estimations of the probabilistic vector space.

In one embodiment, probabilistic models can be selected based on certain criteria. For example, probabilistic models can be selected in order to adapt for different data types for the underlying feature vector. For example, the feature vectors can contain profile features, symptoms, attributes, and values that are binary, multinomial, continuous, or a combination thereof. Models such as neural networks can be selected for a great variety of data types. Hidden Markov models can be selected for some specific combination of multinomial and continuous data types. Dynamic Bayesian networks can be selected where the Hidden Markov models can be suitable. Bayesian networks can be suitable for binary and multinomial data types. Regression models can be suitable for modeling a great variety of data types.

In another example, probabilistic models can be selected in order to utilize different strategies. Strategies can include increasing entropy or decreasing entropy, each suitable at selected states or parts of the health conversation. Increasing entropy can be a model that can be used for validation of hypothesis (aiming to reduce uncertainty), various other probabilistic calculations including, for example, variations on conditional likelihoods. Decreasing entropy is an example of criterion for ruling out some relevant rare conditions. Other approaches for ruling out conditions can be using probabilistic distance function like KL distance, variation on mutual information measures, or conditional information measures. Such approaches can be directed towards increasing the uncertainty for ruling out certain medical conditions.

Increasing uncertainty, or increasing entropy, in the criterion can be a way to identify which conditions to rule out in a specific context. The strategy may depend on certain factors. For example, if the health conversion can only ask a limited number of questions, the system can determine, at a selected stage of the health conversation, to use a selected number of questions to rule out certain medical conditions.

d) Using a set of stored rules or protocols (implemented as a heuristic model) entered manually for certain state vectors. For example, encoding a protocol that is triggered if a person is over the age of 50 and complains of a chest pain. Exemplary protocol can include the good clinical practice rule, also referred to as good clinical practice rule. The protocol can include any criteria that is predetermined for overriding a result generated by artificial intelligence of the server system 200. Stated somewhat differently, when a health conversation 262 (shown in FIG. 5A) uses the model 210 to generate a next question, the good clinical practice rule can determine that such a next question cannot be used. The good clinical practice rule can be rules based on human decision including, for example, business rules, domain rules, and/or legal constraints. The good clinical practice rule can thus introduce human interference as needed to affect output of the server system 200, so the output of the server system 200 can be based on a combination of machined learned model and human influence. Certain heuristics and rules are applied to maintain good clinical practice rule. Examples of good clinical practice rules heuristics include the following. If symptom X is positive, ask about symptom Y. Or if attribute A of symptom S (or S.A) has value N, asked about attribute B of same symptom.

e) Employing a user-experience driven rules to limit, for example, the number of questions in the conversation.

The approaches (a)-(e) can be combined using any selected order and/or priority. In one embodiment, the conversation method can use the good clinical practice rule to narrow down the candidate questions (or exclude questions not to be asked). Among the candidate questions, the conversation method can select the next question by using approaches (a)-(c) and (e) via a random selection or predetermine selection criteria.

The server system 200 can mimic a heuristic model to distinguish from conventional models based on decision trees. Questions posed by conventional methods are static based on decision trees. In contrast, the server system 200 constantly updates for the next best question. Specifically, the server system 200 can leverage validated external medical knowledge and implement the same as a heuristic model that is activated in relevant context.

To create a large enough training data set that is based on actual rich medical data of a large enough population, requires going through the steps, and solving several issues described below. Some of the steps are optional and can be omitted in some embodiments.

The system can be based the type of data as described in the following. Some of the data are provided for illustrative purposes only, and the system can be extended to use and support additional data sources to provide wider and richer information. Additionally, a complete set of parallel records can be obtained for another population from a different source and be combined into the training data set using the method disclosed.

1. Visit records—those records describe patient visits to a physician. Each such record can include some of the following fields. Other fields, are possible and the list below is given as an example:

(a) Patient ID—some unique identifying number that allows tying all pieces of information related to the same person. There are privacy concerns related to the choice of this identifier, but those are beyond the scope of this disclosure.

(b) Date of Visit (c) Doctor Specialty—A visit can be to a general practitioner/primary care physician or a specialist.

(d) Free text notes—these are both description of the user symptom, physical test, doctor notes and conclusions (e) Potential or actual diagnosis—typically encoded in some standard such as ICD-9

2. Patient records—linking a Patient ID to data such as gender, age

3. Lab Test results, tied to a patient by Patient ID, contains the date of the lab test and the results (list of markers and their values, such as: level of hemoglobin, red blood cells count, etc.)

4. Medication Records—prescription and purchase date, medication name (usually encoded in some standard), dosage, total amount 5. Other possible sources include: imaging test results (image+doctor summary), hospitalization records, treatment and medical procedures records, measurements such as weight, height, blood pressure and others.

Figure 6:
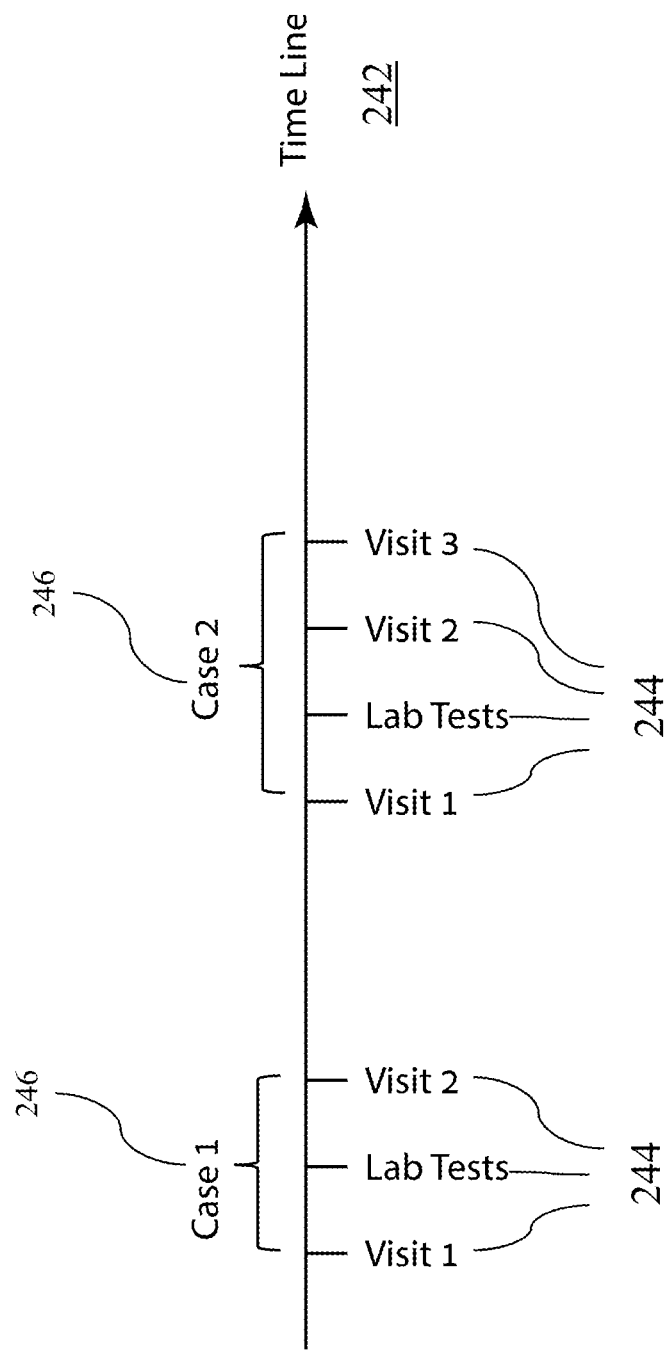
FIG. 6 is a diagram illustrating construction of a timeline by the server system of the environment of FIG. 1.

Turning to FIG. 6, an exemplary timeline 242 is shown. The server system 200 can construct, per person in the system, the timeline 242 of a "medical journey"—a list of medical events 244, such as doctor visits, lab test results, medications taken, etc. ordered by date they took place.

The server system 200 can optionally determine significant events along this timeline. The decision of what's important may vary depending on the model the system is trying to build. For example, when modeling the diagnosis of a set of conditions, the system tries to find visits where the doctor diagnosis was one of the conditions it is trying to model. For example, considering "Upper Respiratory Infection", the system may try to find visits where that condition was the doctor diagnosis (ICD9 code 465.9, for example).

The system can use a set of heuristic rules based on physician behavior and note taking is used to help increase the accuracy of the NER capture. For example, the system can use a set of heuristic rules to decide what is considered a "diagnostic visit." Sometimes, doctors write a "possible diagnosis" and not a conclusive one, sometimes they write a diagnosis only in the last visit of a series of related visits.

The system can use a set of heuristics to decide what constitutes one medical "case". A case may be a set of events recorded in the health care system that are related to one condition. An example for a typical case may start with a non-conclusive visit record (no diagnosis) followed by lab tests, and then followed by a conclusive visit. By way of example, the system can decide what visits are part of the same case by grouping all visits that are no more than a predetermined time interval (for example, 1 week) apart from each other. For example, the medical case 246 that is 'case 1' can include visit 1, lab tests and visit 2, if visit 1 and visit 2 are less than a week apart. The medical case 246 that is 'case 1' can include visit 1, lab tests, visit 2 and visit 3, if visit 1 and visit 3 are less than a week apart. The system can treat the last visit diagnosis, if recorded, as the diagnosis of the whole case. For example, the diagnosis of visit 2 of 'case 1' can be the diagnosis of 'case 1,' and the diagnosis of visit 3 of 'case 2' can be the diagnosis of 'case 2.'

The set of heuristics used can change based on other considerations as desired. For example, if the diagnosis of interest is a chronic disease (compared to an acute disease), the first visit in a set of visits where the diagnosis is given can be used. Alternatively, the visit after which a chronic medication was prescribed can be used as the visit from which the most information can be gathered regarding the chronic disease case.

Once a case is found for a given diagnosis, a case visit record is created by the system for the case with its structured data fields and free text fields.

While the diagnoses can be coded and easy to extract, the set of patient complaints and doctor notes is provided as free text, typed by the doctor during (or right after) the visit.

To extract significant enough information from the free text fields of a visit record, the system employs multiple steps as following.

Initially, a subset of the visit records is selected to cover broad enough variety of the population and the conditions modeled. The subset texts are then used to manually tag symptoms, attributes and values, as well as various relationships (such as negation). This tagging operation creates a few database tables that link the visit records to SAV tags. These tables can be noted as the "tagged visit vectors" as they link a visit record to a set of tagged symptoms, attribute and values. The relationship between symptoms, attribute and values is also kept in that database (e.g., the value "for 3 days" is a value of the attribute "how long" for the symptom "headache").

Figure 7:
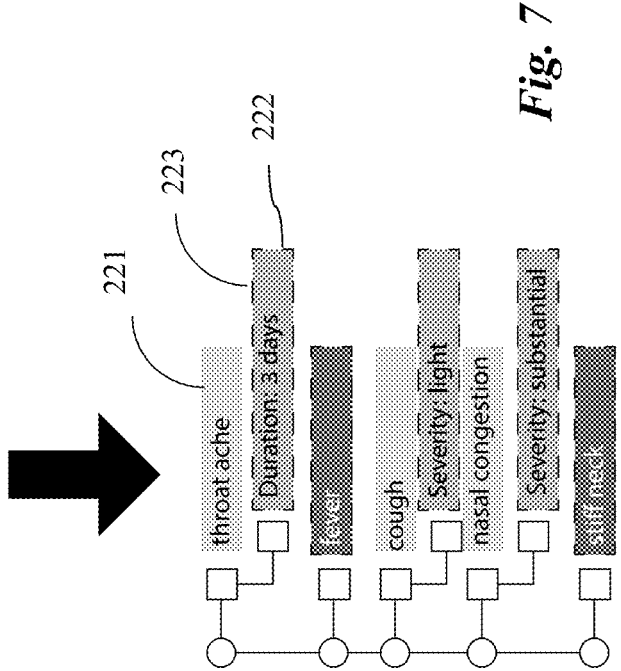
FIG. 7 is a diagram illustrating an exemplary embodiment of a user interface used by the server system of FIG. 1 for tagging.

Turning to FIG. 7, an exemplary manual tagging user interface is shown for selected free text from a doctor's visit. Doctors often don't codify a patient's problems in a consistent way. For example, doctors often use multiple abbreviations and codes. Their handwriting and spelling is relatively poor as done in haste. Doctor practices differ vastly by geography, seniority, payor relevance, etc.

As shown in FIG. 7, a person tagging the text (or a human tagger, usually a medical doctor, medical student, etc.) marks texts as being a symptom (throat ache), attribute (severity) and value (light), forming a symptom tag 221 and an attribute tag 222 integrated with a value tag 223. Note that negative symptoms (that is, symptoms that the patient does not suffer from) are market as negative (e.g., no fever).

Once the first subset of records is used for manual tagging (at least few thousand records), an automated process ("Auto Tagger") can take place and cover a much larger set of visit records. The Auto Tagger uses the tagged visit records database, having symptom tags 221, attribute tags 222 and value tags 223, and use those to search the text fields of a much larger set of (non-tagged) visit records.

An exemplary auto-tagger does not produce new tag objects—it merely reuses tags that were output from the manual tagging phase. However, an alternative exemplary but auto-tagger can create new tag relationship records.

In one embodiment, the tagging tool can allow the human tagger to be presented with sample notes. The human tagger can select a word, identify if it is a symptom, attribute or value, and can mark it as similar to a different one (for example select "stomachache" and mark it as a synonym to "abdominal pain").

The tagging tool can include a web-browser-based user interface (shown in FIG. 7). The server system 200 (shown in FIG. 1) can present the sample notes to the human tagger via the user interface and receives, via the user interface, tags as the tags are applied to words in the text. The notes and tag information can be stored in a database system. The database system can be based on any suitable database structure. An exemplary database structure can be relational or graph. For example, the database can be based on Microsoft Structured Query Language (SQL). In an unlimiting example, the user interface can be programmed in JavaScript and/or Hypertext Markup Language (HTML). The server system 200 can be programmed in various programming languages. In an unlimiting example, python and/or Ruby On Rails can be used to develop the server system 200.

The tagging allows marking a word as symptom, condition (disease), attribute (for example: severity, location, how long, etc.) and value (severe, mild, one side, both sides, etc.). Negative values can be marked. For example, "No abdominal pain" is marked as negation of the symptom "abdominal pain" where mucus with no blood is a negation of a mucus type value "bloody".

Once a sample of notes is tagged by humans, an automated process that uses heuristics and regular expressions is used to tag the remaining texts.

Figure 8:
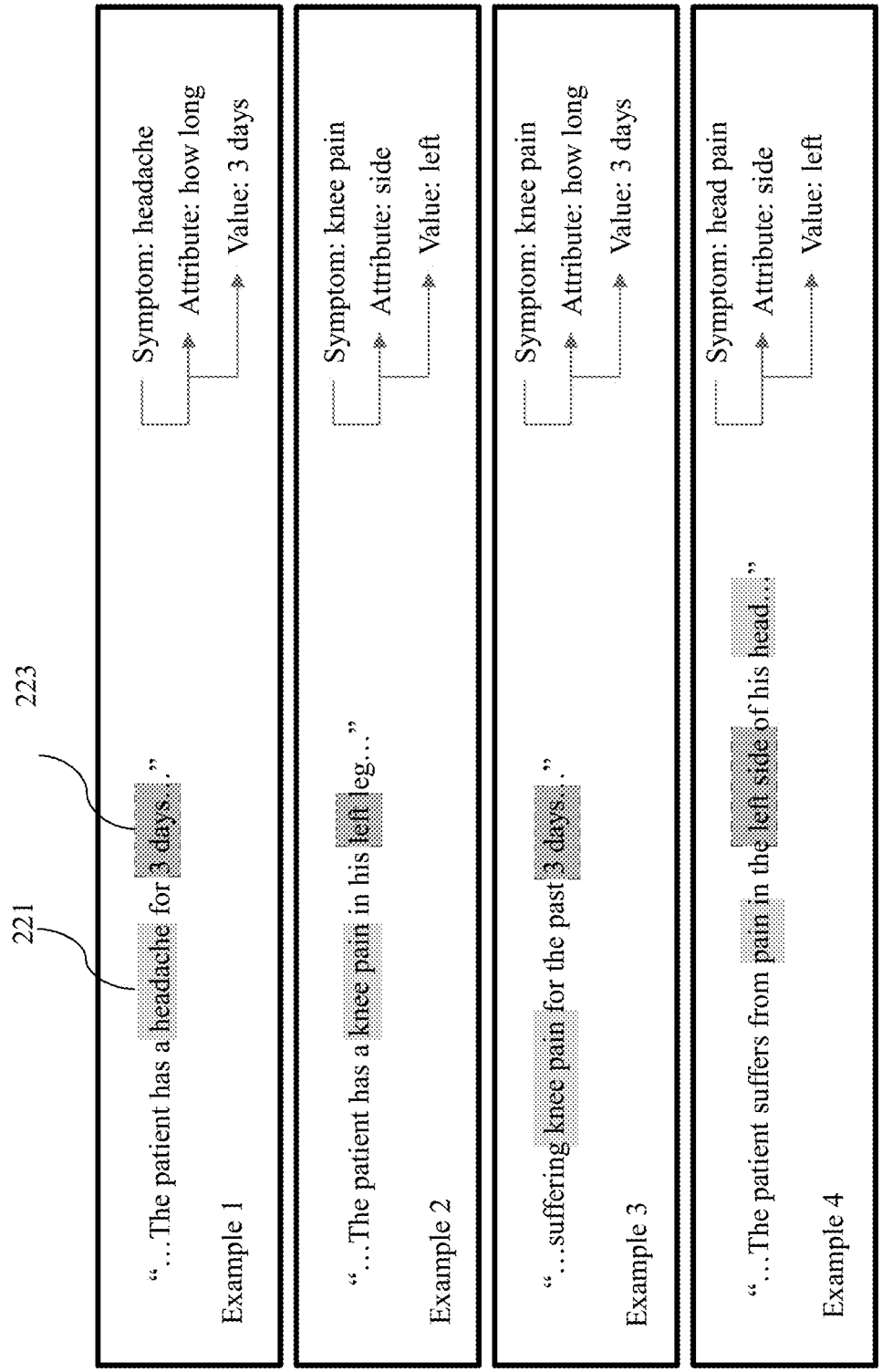
FIG. 8 is a diagram illustrating a plurality of examples of tagging by the server system of FIG. 1.

Turning to FIG. 8, examples of tagging are shown. In Example 1 and Example 2, manual tagging can be used to identify the symptom tag 221 of "headache" linked to an attribute "how long" with a value of "3 days" (example 1), and the symptom tag 221 of "knee pain" linked to attribute "side" with value "left".

FIG. 8 shows auto tagging as being performed on Example 3. The auto tagger uses the existing tags and identifies "knee pain" as a symptom and the same attribute as found for headache before "how long" with the value "3 days". The auto tagger adds a tagged visit record with the found tags and adds the relationship (that did not exist after manual tagging) of symptom "knee pain" having attribute "how long".

When searching for known tags in new visit records, a string-matching approach can be used, for example. In the environment 100 (shown in FIG. 1), an "edit distance" function, which matches two strings based on a modified "edit distance" function, can be used.

A standard edit distance function gives the number of additions, deletion or changes of characters needed to be applied to one string in order for it to be transformed to a second string. For example, the edit distance between the string "to" and the string "too" is 1—there is one addition needed to go from the first to the latter. A custom, language-specific edit distance is proposed to accommodate for various Hebrew language constructs. For example, adding the Hebrew letter Bet (ב) to a noun means "inside" or "in the" so adding it to the noun "head" (ראש) makes the sentence כאב ראש (head pain) to כאב בראש (pain in the head) a standard edit distance of 1. But in terms of meaning, this can be treated as a shorter distance than the standard edit distance of 1. Because "pain in the head" is semantically very close to "head pain" in meaning. A plurality of edit distance functions can be respectively determined for accommodating for a plurality of languages.

An alternative embodiment for the auto-tagger can be constructed to deduce new tags, for example by keeping a table of synonyms and deducing that expression such as "<organ>pain" is equivalent to "<organ>ache". These kind of patterns and rules are language-specific and may need to be adjusted to the language the text is written with.

After running the process of auto-tagging, additional iterations of manual tagging can enjoy from "pre-tagged" records that a manual tagger can simply review and make edits to.

At the end of manual and automated tagging iterations, the system has several thousand, or millions tagged visit records corresponding to patient visits with a known diagnosis, each one linked to symptom, attribute and value tags. In addition, a hierarchical structure of links between symptom tags to attributes and value tags is established.

Following those tagging iterations, a "post-tagging" process is run in a semi manual mode where the end result is a combined "symptom, attribute, value OBJECTS model"— in which a canonical term is used to group multiple tags. For example, the symptom tag in example 4 above ("pain head") is grouped with the symptom "headache" from example 1 to form one canonical symptom object named "Headache". Similarly, the value tag "left side" from example 4 is grouped with the value tag "left" from example 2 to form one canonical value object named "unilateral—left". Such canonization can allow training of the machine learning model 210 (shown in FIG. 3A).

Figure 9A:
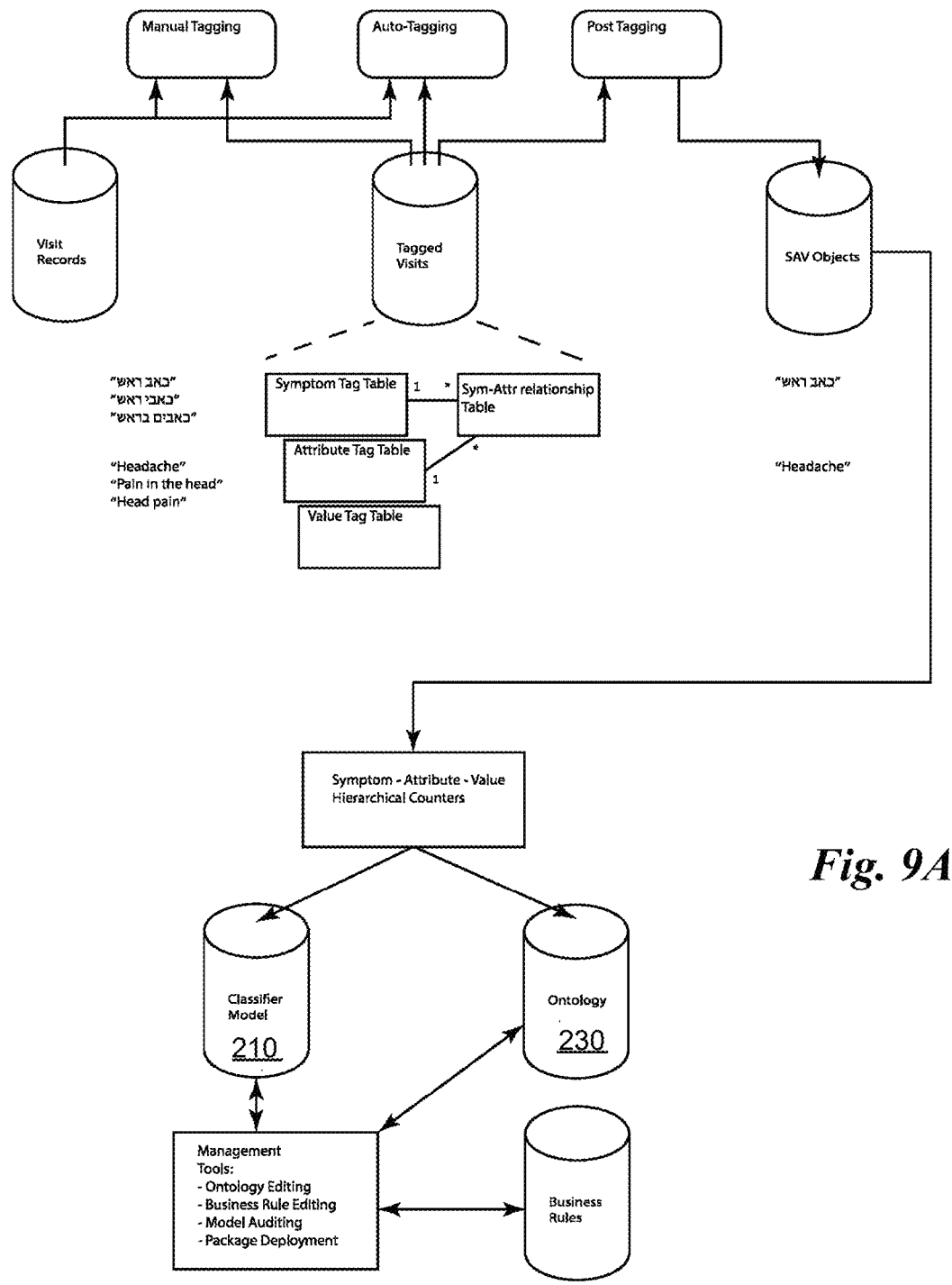
FIG. 9A is a flow diagram illustrating an exemplary embodiment for tagging using the server system of FIG. 1.

Turning to FIG. 9A, an exemplary diagram illustrating an embodiment of a tagging process is shown. The results of the auto-tagging and post-tagging of the larger population, produces a very large set of tagged visit vectors—a conversion of the free text fields from the visit records, along with the structure information (such as the visit date, the ICD9 diagnosis, and the patient ID).

Figure 9B:
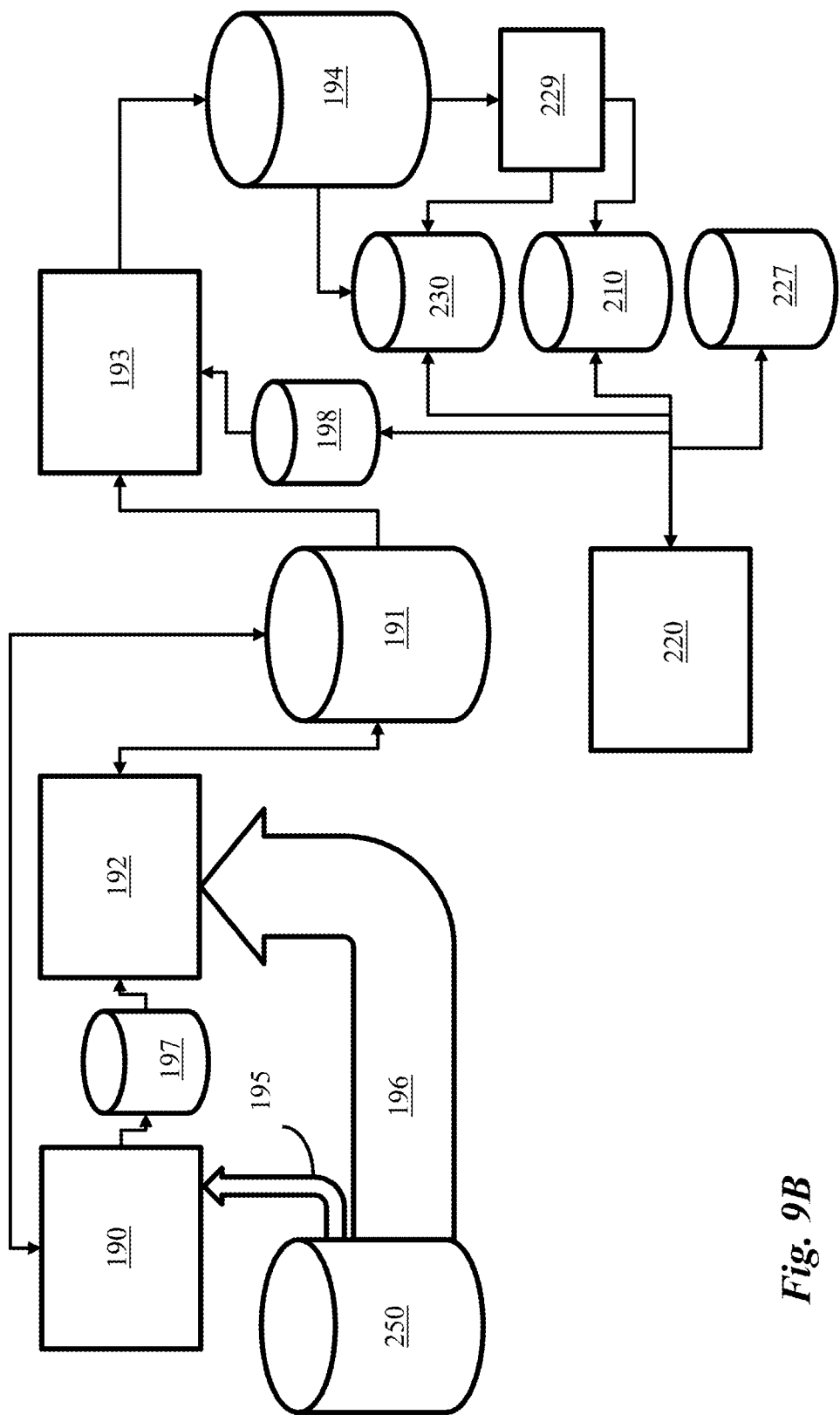
FIG. 9B is a flow diagram illustrating another exemplary embodiment for tagging using the server system of FIG. 1.
Figure 9C:
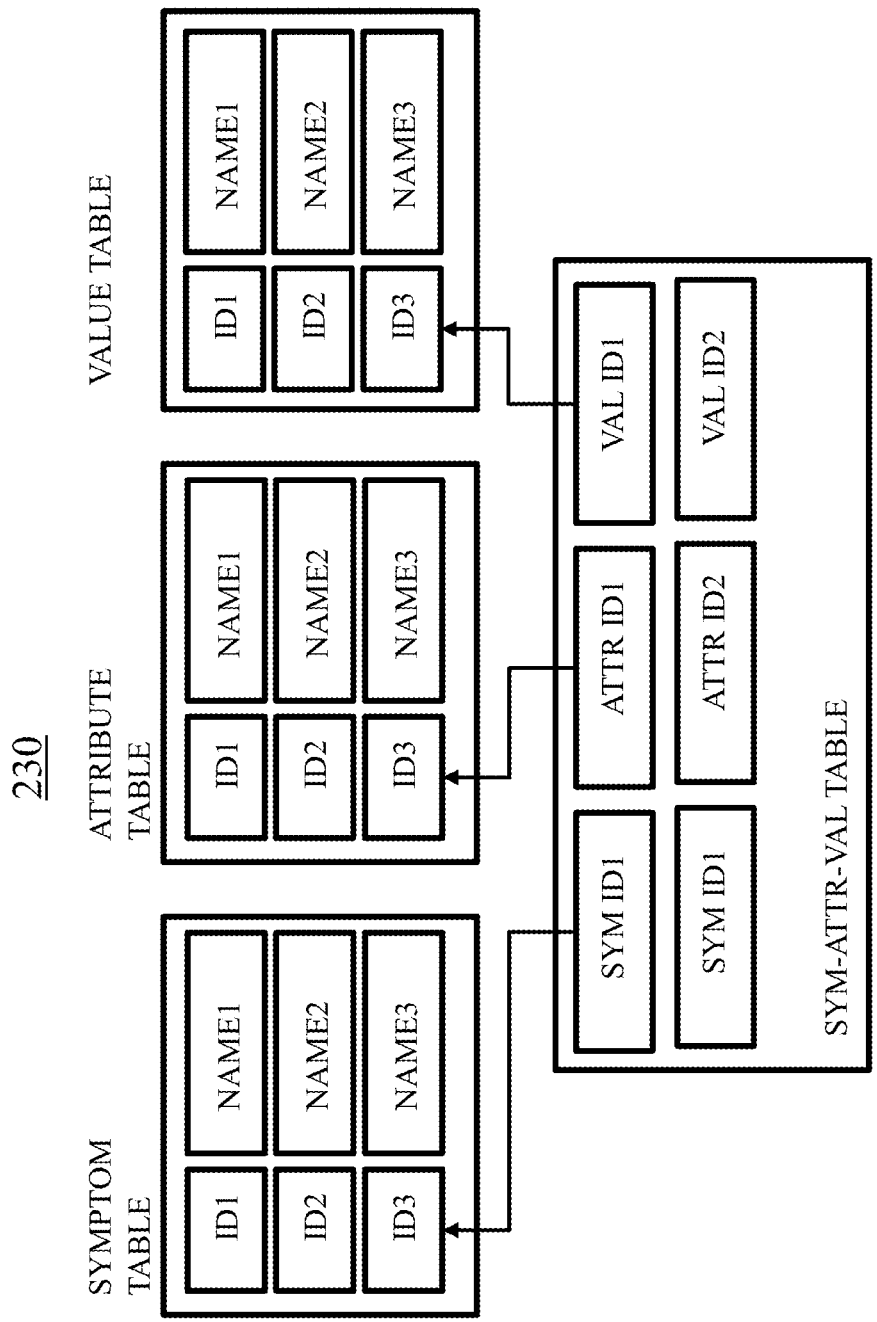
FIG. 9C is a diagram illustrating an exemplary embodiment of an ontology implemented by the server system of FIG. 1.

Turning to FIG. 9B, an exemplary diagram illustrating an alternative embodiment of the tagging process is shown. The SAV objects of the objects in the ontology 230 (shown in FIG. 3C) can be stored in a relational database or a graph database. In a Graph database, the relationship between a symptom, possible attributes thereof, and the possible values for the attributes can be represented naturally in a graph. In one embodiment, The SAV objects can be stored in a relational database. In the relational database, the SAV objects can be stored in tables, such as Symptom table, Attribute table and Value table, and then with relationship tables, such as SymptomAttribute table, and SymptomAttributeValue tables as shown in FIG. 9C.

FIG. 9B describes the process of tagging (manual and automatic) and the model building. From a large set of integrated health records 250, each record can correspond to a doctor visit. Each record can be made of structured data (for example: age, gender, medical history, visit date, doctor diagnosis, lab results) and textual data: patient complaint description, doctor notes. A subset 195 of those records can be used for manual tagging in a manual tagging system 190.

The text from each record of the subset 195 can be presented to a human operator who can mark the words in the text that are either symptoms, or attribute values. Attribute values can include values of selected attributes. The result of that manual tagging process is a dictionary database 197 containing both a list of words or phrases describing symptoms, attributes and values as well as a list of all possible symptom-attribute-value combinations.

In some embodiments, attributes can be seldomly found as words in the text and can be pre-defined by domain experts. When a certain note is identified to have a new attribute, the note can be manually added to the dictionary database 197. During the manual tagging, the expert (or "tagger") can mark a word or phrase that is a value and can select the relevant attribute from a pre-defined list. For example, in the sentence "the patient is presenting a headache for 3 days", the human tagger can mark "3 days" as the value for the attribute "how long?" or "duration."

In another example, for texts containing negation, such as "Patient presenting headache for 3 days with no fever", the human operator can mark "fever" as a symptom word and can mark it as having a negative value in this record. The symptom "fever" can be recorded in the dictionary database 197 but can be marked has having a negative value when written to a tagged visit record 191.

The resulting dictionary database 197 can be used by an automatic-tagger process 192 to go over the vast majority of the integrated health records 250 and tag them.

Auto-tagging uses the dictionary database 197 of words and phrases from the manual tagging phase to scan the large number of text notes 196 from the integrated health records 250. The auto tagger can be implemented as a set of regular expressions, and/or other heuristics searching for the dictionary phrases in the text. Exemplary pseudo code for auto-tagging is presented in Table 3.

TABLE 3

| Line | Instruction |
|---|---|
| 1 | Read next integrated health record text part → $T_i$ |
| 2 | SAVi ← { } |
| 3 | $sp_j$ → get next dictionary symptom phrase |
| 4 | If $sp_j$ IN $T_i$: |
| |    a.  Handled ← false |
| |    b.  Wn ← get next negation pattern |
| |    c.  If Wn in Ti within N characters before or after occuence of $sp_j$ |
| |        i.  $SAV_i$ ← SAVi + {NFG(ID of$sp_j$)} |
| |        ii.  Handled ← True |
| |        iii.  Go To 4.e |
| |    d.  If more negation patterns: |
| |        i.  Go to 4.b |
| |    e.  If NOT handled: |
| |        i.  $SAV_i$ $SAV_i$← {ID of $sp_j$} |
| |    f.  $av_k$ get next dictionary attribute-valuephrase |
| |    g.  If $av_k$ in $T_i$within A characters from occurrence of $sp_j$. |

TABLE 3-continued

| Line | Instruction |
| --- | --- |
| 5 | i. SAVi ← SAVi + {ID of sp$_j$, ID of ATTR(av$_k$) , ID of VAL(av$_k$) } |
| 6 | If there aremore dictionary symptom phrases go backto 3 |
| 7 | Write SAV$_i$ to Tagged Visits |
|  | Are there more integrated health records to process? |
| 8 | a. Yes: got to step 1 |
|  | FINISH |

An additional and/or alternative method can separate the detection of entities in the text from matching of an attribute value to a symptom.

An additional and/or alternative implementation of auto-tagging can make use of neural network methods (such as word embedding, for example) to extract entities, using manual tagged texts as a training set for such methods. Such methods may more easily deal, for example, with minor spelling mistakes.

Both the manual tagging process and the auto-tagger process can produce a set of tagged visit records 191 that contain the extracted text phrases and a reference to the original medical record with the structured data they originated from.

At this phase, the extracted text phrases may contain duplicate terms referring to the same object. For example, the two phrases "headache" and "pain in the head" can appear as two separate symptom expression both in the dictionary database 197 and in the tagged visit database 191.

A post-tagging process 193 can have a function of consolidating (and/or grouping) those expressions into ontology objects and produce final tagged visit records 194 that can be used for model training. The final tagged visit records 194 can be used for training the model 210, storing in the ontology 230 and/or optionally managed by one or more SAV Counters 229.

Grouping can be performed by referring to a grouping table where a symptom_group_id is assigned for each symptom word or phrase in the dictionary database 197. The grouping can be implemented by matching (including, but not limited to, exactly matching) a phrase (or word) with an entry in the dictionary database based on suitable NLP algorithms such as semantic and phrase analysis, edit distance matching. The assignments can be stored in the grouping-mapping-filtering database 198. In the example above, both "headache" and "pain in the head" can be listed with symbol_group_id=10 (as an example, assuming 10 is the ontology code for the canonical Headache symptom).

Additionally and/or alternatively, the post-tagging process 193 can perform functions of removing mistakes and/or mapping. Because both manual tagging and auto-tagging can produce mistakes because of human error, misspelling or mis-identification of terms, the post-tagging process can apply a list of filters to remove certain errors. Those filters can be implemented, for example, as a set of invalid (or illegal) symptom-attribute-value combinations and can be entered manually via the management system 220 and stored in a grouping-mapping-filtering database 198.

For example, if a phrase such as "Green headache" can be mistakenly be tagged with a headache with an attribute of "color" and a value of "green", a filter can be added to reject any tagging of headache with attribute color.

Mapping can be used for adding some semantic context to certain symptom-attribute-value combinations. For example, it might be not so important to distinguish between a right foot knee pain and a left foot knee pain, but it can be useful to distinguish between both knees pain vs. one-sided knee pain. Thus, for this example, a mapping of both {knee pain, side, right} and {knee pain, side, left} to {knee pain, side, unilateral} can be made.

Another example is the ability to treat knee pain, elbow pain and ankle pain as instances of joint pain. The post-tagging process can add a new symptom "joint pain" to the tagged visit vectors.

Once the post-tagging process is complete, the resulting final tagged visits 194 that contain the extracted symptom-attribute-value from the textual part of the records, along with the structured data in the records can be used to train a classification model as set forth in the present disclosure.

Figure 10:
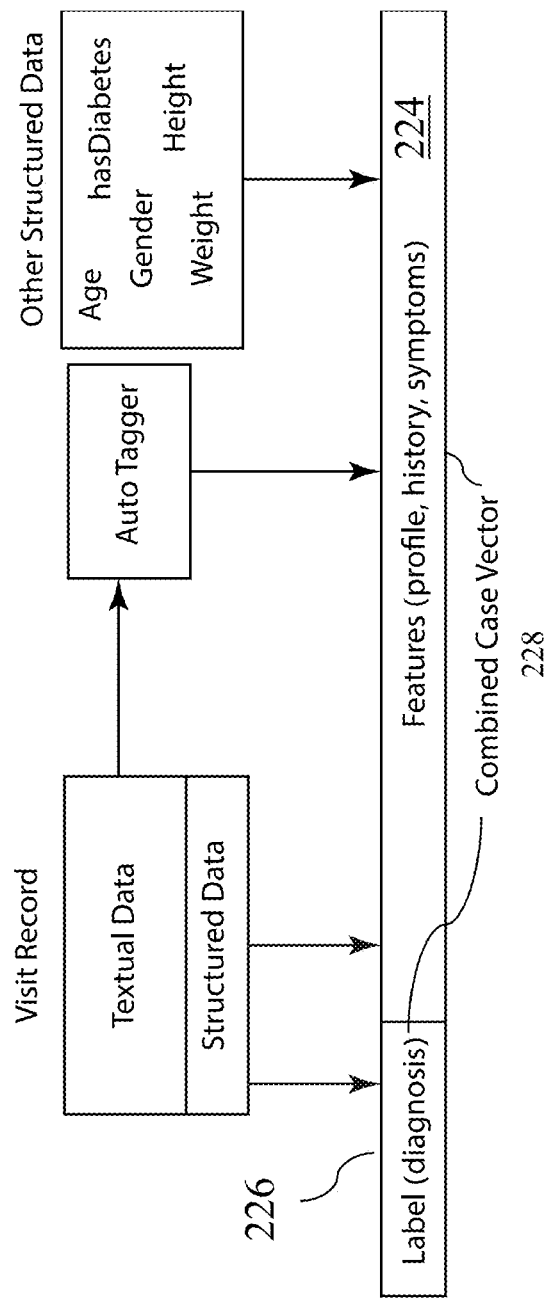
FIG. 10 is a diagram illustrating an exemplary embodiment of a case vector used on the server system of FIG. 1.

Turning to FIG. 10, an exemplary diagram illustrating an embodiment of the case vector 228 is shown. The case vector 228 is shown as being a combined vector including the feature vector 224 of the medical case 246 (shown in FIG. 6) and diagnosis of a medical condition of the medical case for the same medical case 246. Those records along with the other data sources provide a larger case vector 228 that includes information such as patient age and gender, indication of chronic conditions, smoking habits, weight or BMI, and symptom features (the symptoms, attributes, and values) extracted from the text and the diagnosis.

The set of case vectors for the whole population can then be used for building machine learned models, such as described herein.

Figure 11A:
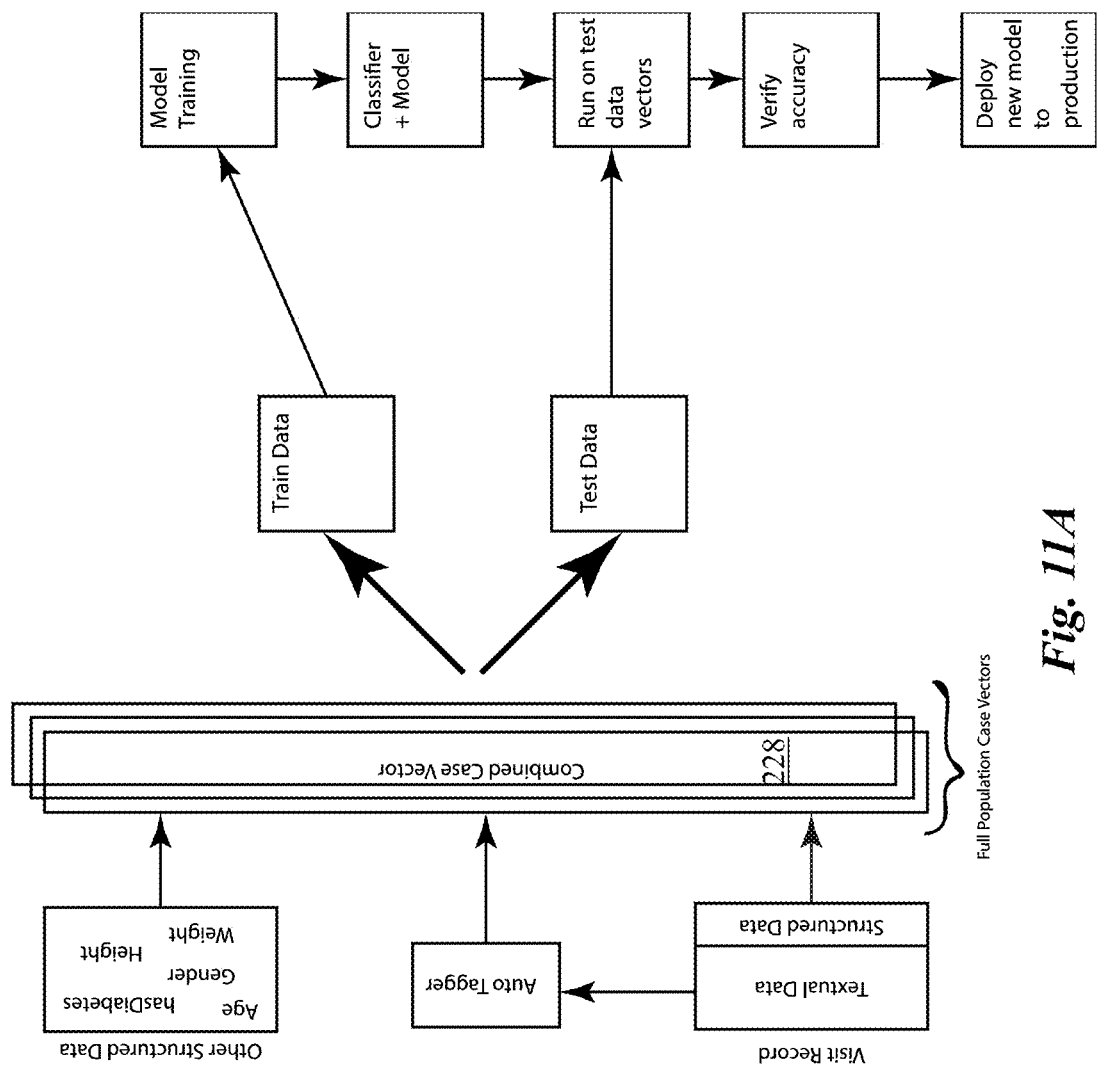
FIG. 11A is a flow diagram illustrating an exemplary embodiment of a process for building a health predictive model by the server system of FIG. 1.

Turning to FIG. 11A, an exemplary diagram illustrating an embodiment of a process of machine learning is shown. The classification server (or condition classifier) 268 (shown in FIG. 3C) can include one or more classifiers. When using more than one classifier, there is an additional process that implements some "voting" or other decision heuristic to pick the best classification result.

A classifier is a computer-based method for classifying a case characterized by a feature vector as belonging to one or more "classes." In some uses, a classifier is used as a predictive model where it "predicts" which class is most likely to fit a given vector of features. In the environment 100 (shown in FIG. 1), the vector of features is a combination of user profile attributes (such as age, gender, chronic diseases), past interaction of the user in the system, and answers to the current health dialogue. The classes in the environment 100 are different medical conditions/diseases in one case, or other predicted medical information such as medication used, or lab test ordered.

Classifiers can be binary—such a classifier considers one class at a time and provide the probability of the feature vector as belonging to this class. Multi-class classifiers work on a collection of classes, and produce a probability vector for this collection, where each item in this vector is a number between 0 and 1 that can be interpreted as representing the probability of the feature vector to belong to this class. The sum of all those probabilities is normalized to 1.

Such classifier algorithms can be "trained" on sample data and are implemented using one of known Machine Learning or Deep Learning algorithms. The training phase of the classifier creates a "classification model", which can be a large (and in some cases very large) set of numbers. The training phase of the classifier creates a "classification model." The classification model can mean a large set of numbers is included in the model. In different machine learning algorithms, these numbers can mean different things. For example, in a Naïve Bayes model, the large set numbers are conditional probabilities (the probability of a feature given a class). For neural network models, the large set of numbers can mean "neuron activation weights."

That training phase uses a set of case vectors 228, each pre-labeled with a known class. This set of training vectors is known collectively as "training data". This data can be created manually or obtained from existing medical record databases.

The manual creation of training data is cumbersome, tedious and error prone, and is not scalable as the amount of training data should be large enough, and grows as the number of classes, and number of features considered grows. So often, companies and researchers use existing database.

The classification server 268 can use any classification algorithms, any methods to train the classification algorithms and any methods for storing the models are stored. Examples of classification algorithms include: Naïve Bayes, Linear Regression, Random Forest, Neural Networks—NN and various variations of those such as convolutional NN, Recursive Neural Networks (RNNs), Long-Short-Term Memory units based RNNs, etc.

In the exemplary machine learning process, a large set of records of the case vectors 228 can be split to "train data" and "test data", where the train data is used to build the health predictive model 210, and the test data is used to verify that the health predictive model 210 has indeed the classification or prediction ability when tested on the test data.

Once the health predictive model 210 is built, an accuracy of the health predictive model 210 can be validated or measured on the set of "test data" vectors and if the accuracy is good enough, deploy the health predictive model 210 to production.

Figure 11B:
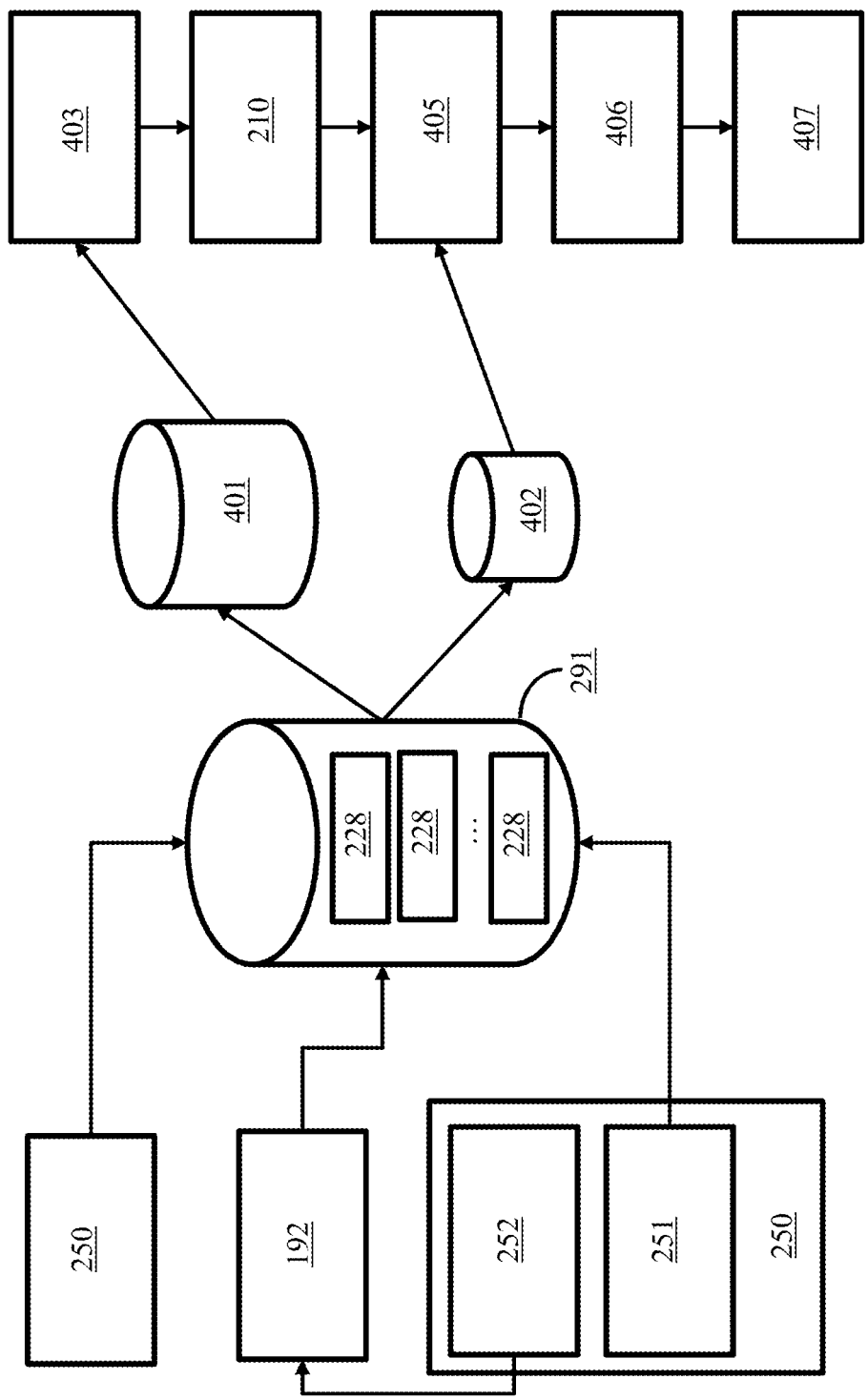
FIG. 11B is a flow diagram illustrating another exemplary embodiment of a process for building a health predictive model by the server system of FIG. 1.

Turning to FIG. 11B, an exemplary diagram illustrating an alternative embodiment of a process of machine learning is shown. The case vectors 228 can include combined data from structured data 251 (age, gender, lab results, diagnosis, etc.) of integrated health records 250 from one or more different sources, and unstructured/text data 252 (doctor notes for example) that can be tagged, for example, by auto tagging 192. The case vectors 228 can form the clean medical records 291 (full population visit vectors). The clean medical records 291 can provide training data 401 to model training 403 to generate the trained model 210. The clean medical records 291 can provide test data 402 to run on test data vectors in a test process 405. A process 406 can verity accuracy of the output of the test process 405 and, upon verification, the process 406 can send the model 210 to a process 407 that deploys the model 210, as a new model, to production.

Figure 12A:
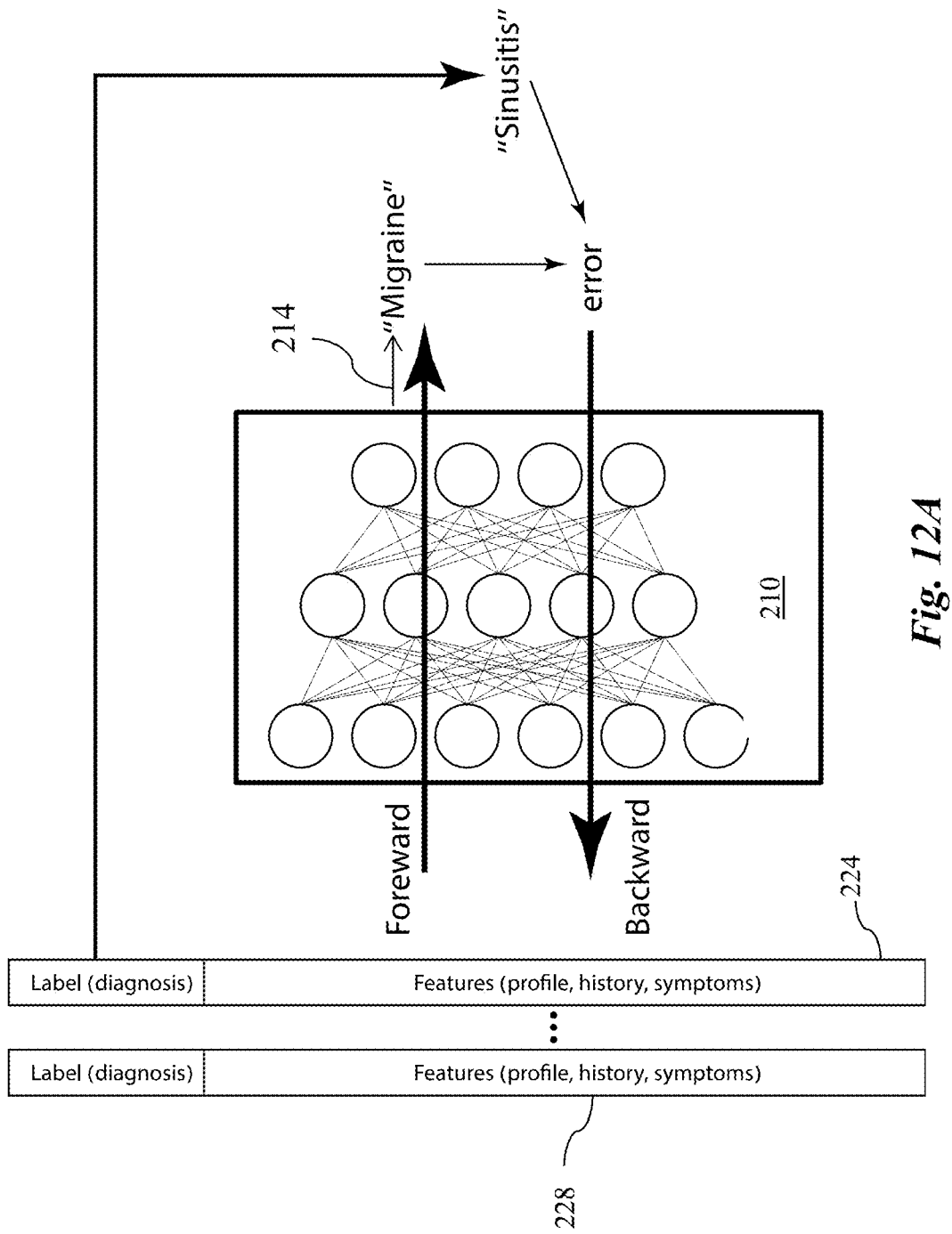
FIG. 12A is a flow diagram illustrating another exemplary embodiment of the process of FIG. 11A, wherein a neural network method is used.

Turning to FIG. 12A, an exemplary diagram illustrating an alternative embodiment of a process of machine learning is shown. The health predictive model 210 can include an additional and/or alternative Neural Network model. The health predictive model 210 can be trained using back-propagation methods using the combined case vectors 228 and/or feature vectors 224 as input and expected output.

Figure 12B:
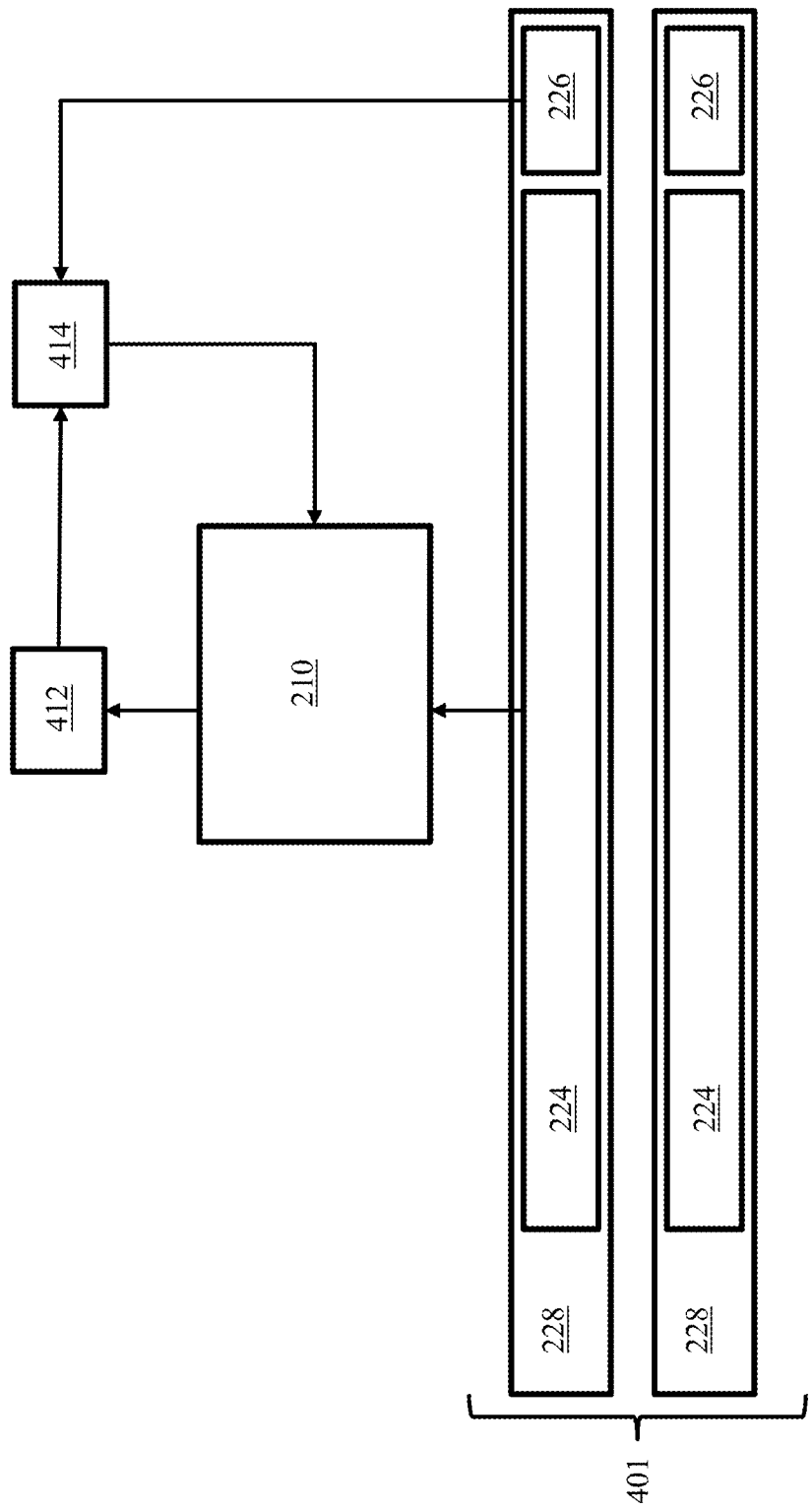
FIG. 12B is a flow diagram illustrating another exemplary embodiment of the process of FIG. 11B.

Turning to FIG. 12B, an exemplary diagram illustrating another alternative embodiment of a process of machine learning is shown. Training data 401 can include a plurality of case vectors 228. Each case vector 228 can combine a feature vector 224 (for example, including profile features such as history, and symptoms, attributes) and a label 226. The label 226 can be any suitable category labels for model training. Exemplary labels 226 can include medical insights, including condition diagnosis, for example. A selected case vector 228 can be inputted into the model 210 being trained, to output a model prediction 412 of a current iteration of model training. An error 414 can be based on a difference between the label 226 and the model prediction 412. For example, the error 414 can be equal to (label 226-model prediction 412).

Management Tools

Additional set of management tools, such as the management system 225 (shown in FIG. 3A) are used to perform manipulation on the ontology and creation of business rules. For example, defining synonyms, disabling certain terms from being used, mapping a certain symptom-attribute-value to another.

Example business rules include the following.

1. Exclusion of certain symptoms or values for a combination of age and/or gender, such as (a) and/or (b) as following.

(a) The symptom "Late period" will not be asked for male, or for female over 60 years old.

(b) The value "testicles" will not be mentioned as a possible value for the attribute "radiating to" when asking about Abdominal Pain.

2. Mapping specific symptom attribute values to others. For example, mapping "Headache" with location: forehead or frontal to "Facial Pain."

3. Mapping specific attribute values to be able to generalize. For example: mapping smaller limb to a larger one, so when referring to "Knee Pain", "Leg Pain" is considered as well.

Auditing/Accuracy Tools

The system can include various tools to perform accuracy and recall calculation on the model. These tools include the following.

1. Running a new version of the model/code on the test data

2. Tools for external doctors or members of a selected medical team to create test cases for various conditions 3. Tools for using application users' cases that has some form of "closed loop" data as test cases for next version models.

Figure 13:
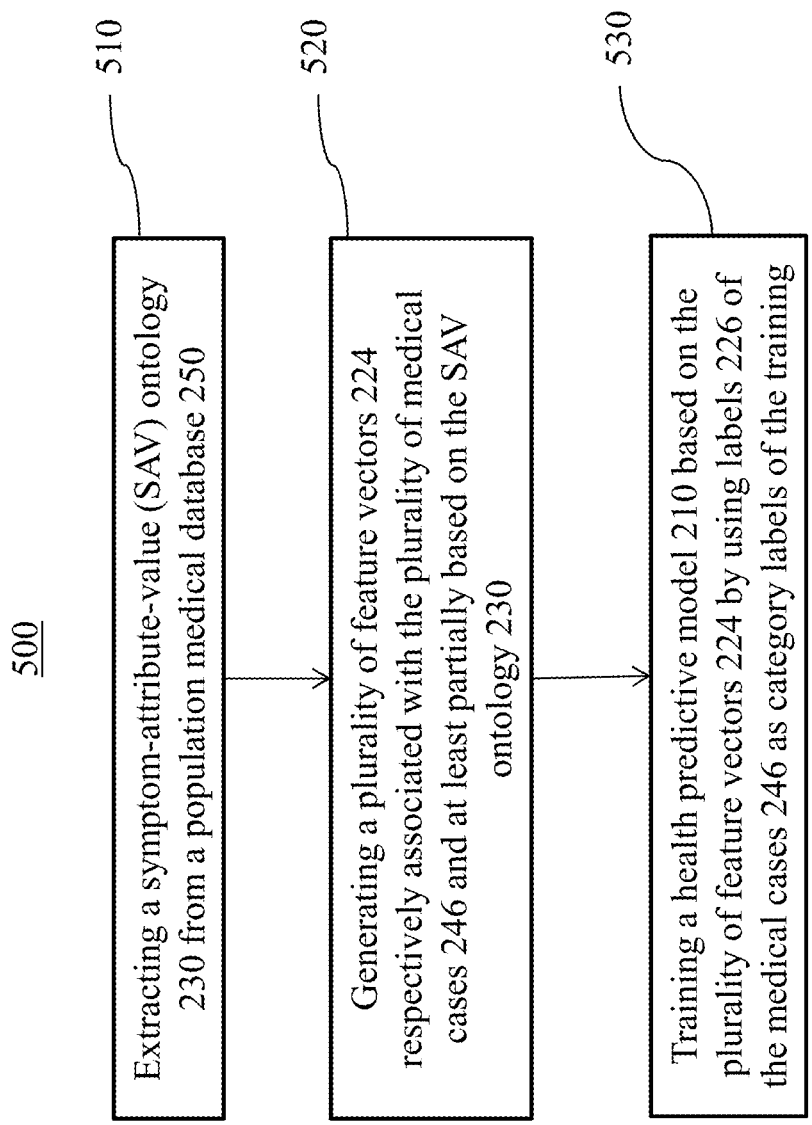
FIG. 13 is a flow diagram illustrating an embodiment of a method for building a health predictive model via the server system of FIG. 3.

Turning to FIG. 13, a method 500 for building the health predictive model 210 is shown. The method 500 can be implemented on the server system 200 (shown in FIG. 1). The method 500 can be used for building the health predictive model 210 based on a population medical database 250. The population medical database 250 can include the plurality of medical cases 246 each associated with a label 226 (for example, a medical condition).

The SAV ontology 230 can be extracted, at 510, from the population medical database 250. The plurality of feature vectors 224 respectively associated with the plurality of medical cases 246 and at least partially based on the SAV ontology 230 can be generated, at 520. The health predictive model 210 can be trained, at 530, based on the plurality of feature vectors 224 by using the labels 226 as category labels of the training.

Figure 14:
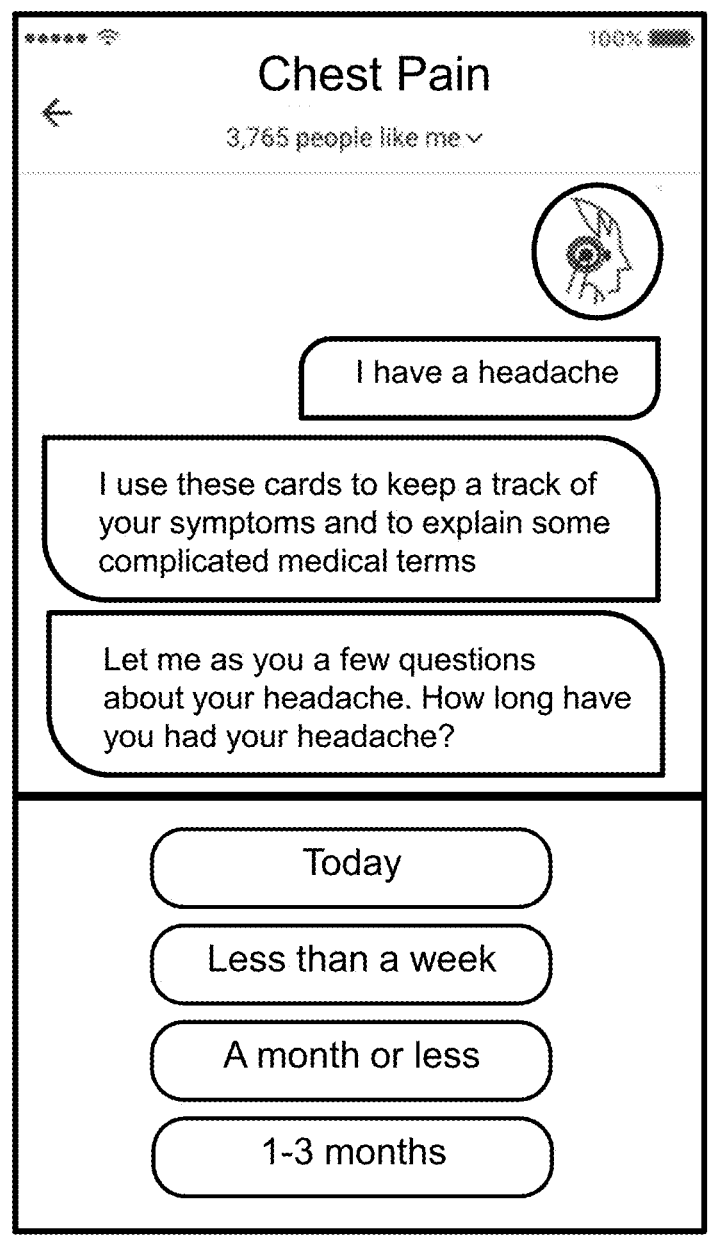
FIGS. 14-18 are detail drawings illustrating exemplary embodiments of a user interface, wherein the user interface is presented on the client device of FIG. 1.
Figure 15:
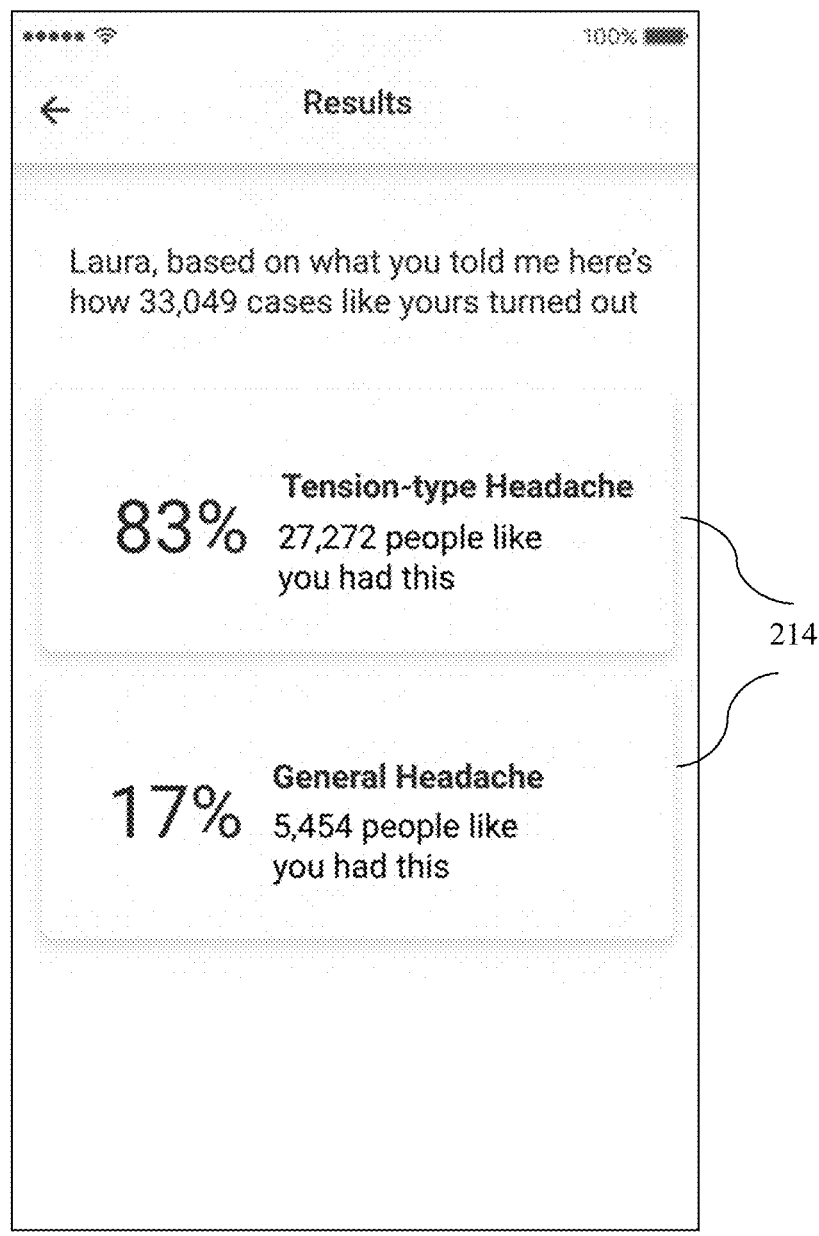

FIGS. 14-15 are exemplary detail drawings of user interfaces 340 during a selected health conversation 262 (shown in FIG. 5A). The user interfaces 340 can be presented on the client device 300 (shown in FIG. 1). FIG. 14 shows the user interface 340 after receiving a response of the first symptom (a headache). FIG. 14 shows the user interface 340 as asking about a value of an attribute (how long) of the first symptom. FIG. 15 shows the user interface 340 as presenting the probability vector 214 that includes a probability of 83% for tension-type headache and a probability of 17% for general headache.

Figure 16:
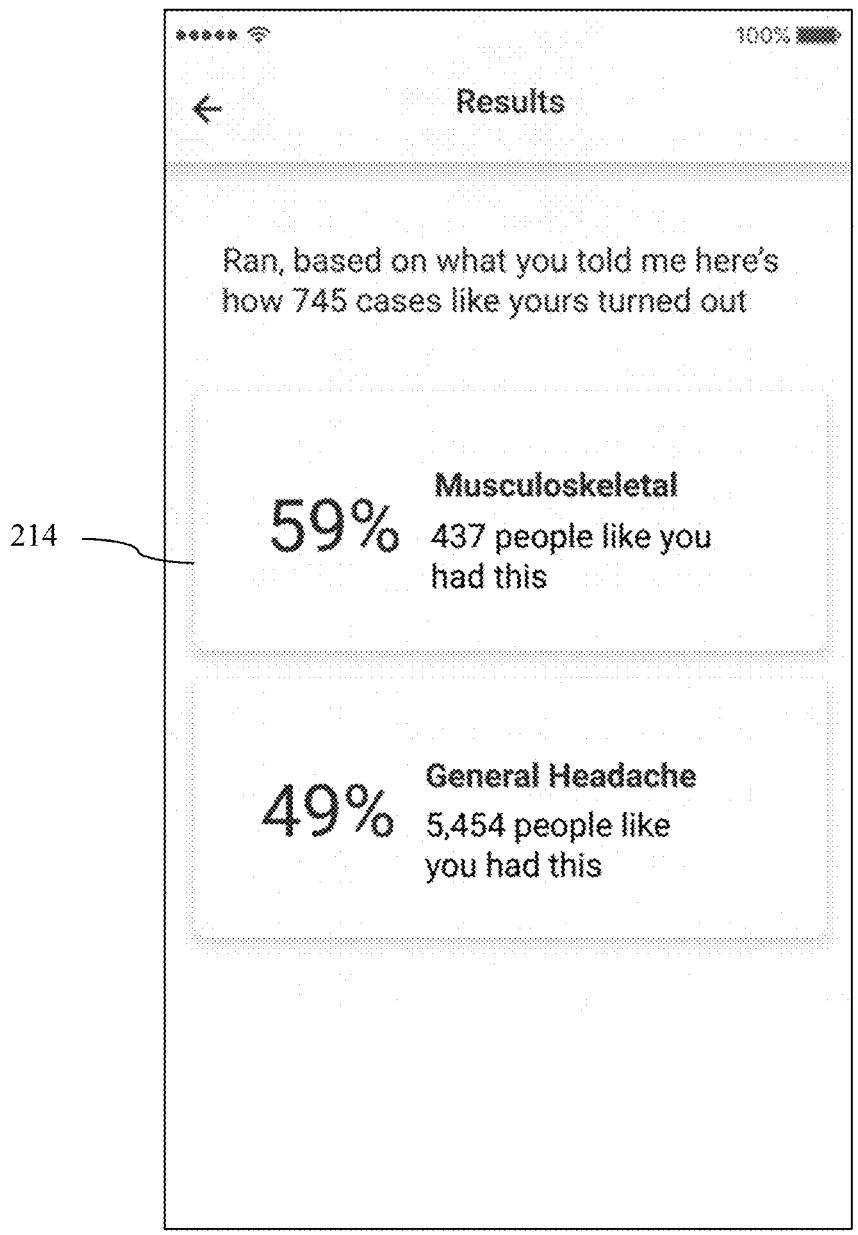
Figure 17:
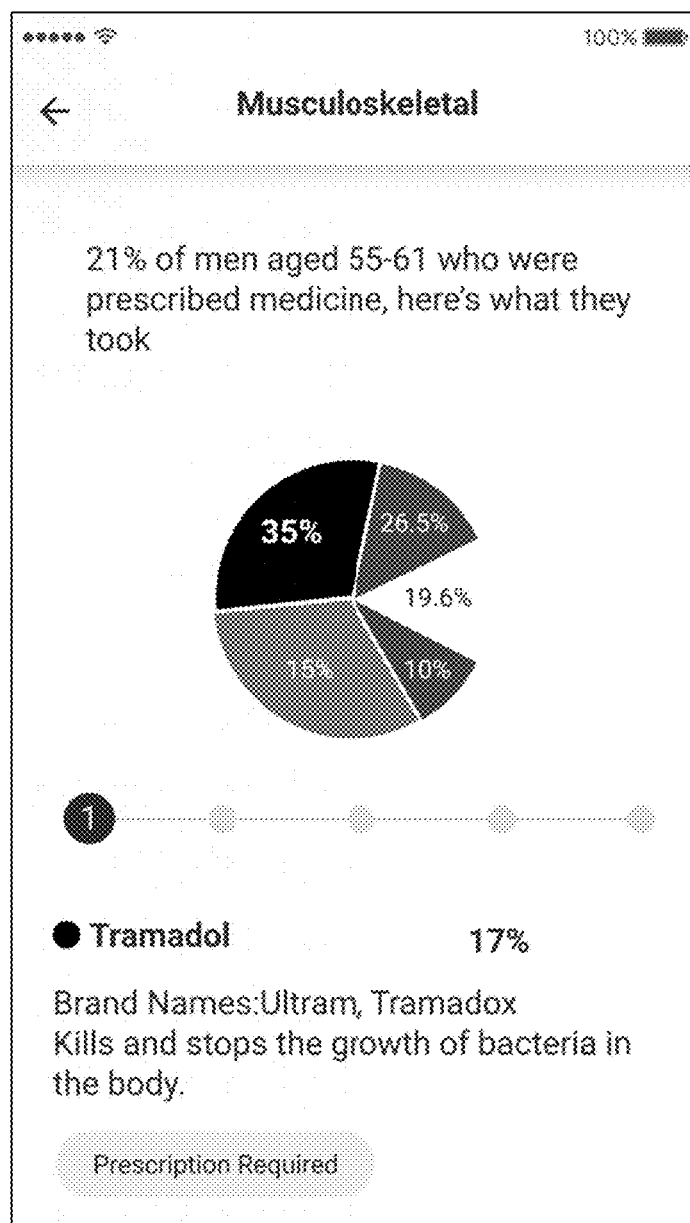
Figure 18:
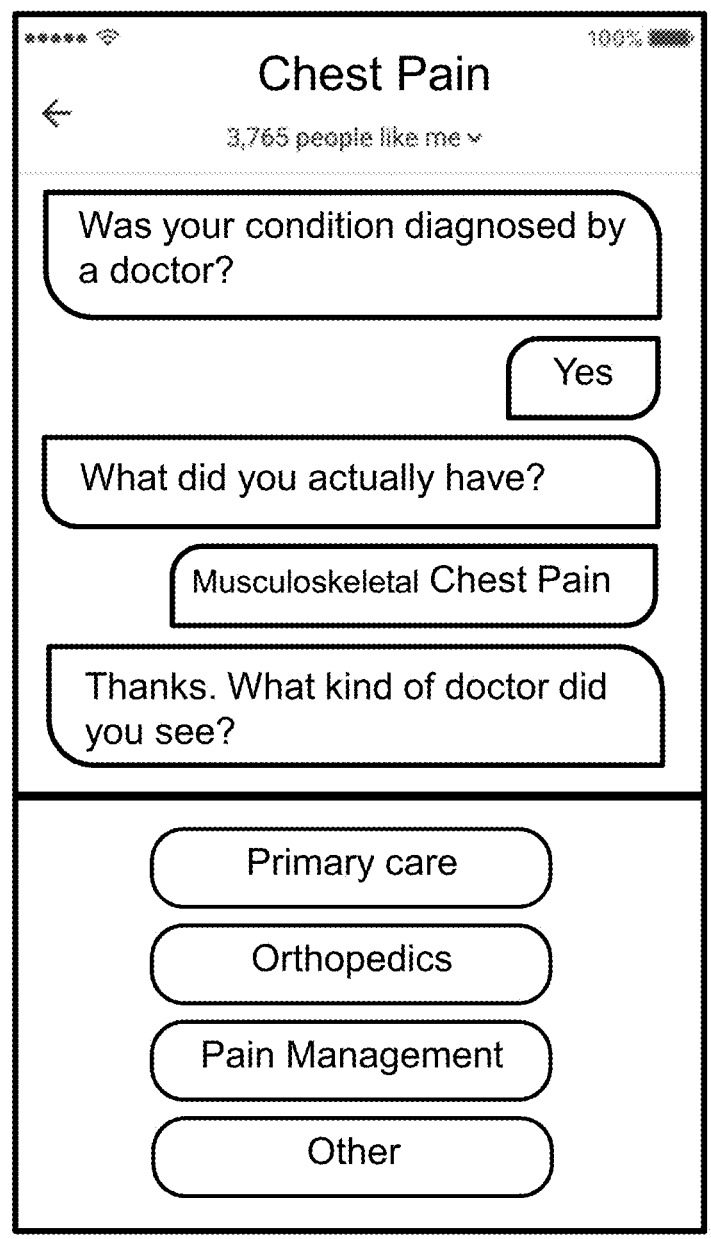

FIGS. 16-18 are exemplary detail drawings of user interfaces 340 showing various screens during an alternatively selected health conversation 262 (shown in FIG. 5A). FIG. 16 shows the user interface 340 as presenting a part of the probability vector 214 that includes a probability of 59% for musculoskeletal chest pain. Stated somewhat differently, the medical condition associated with the greatest probability of the probability vector 214 is presented. FIG. 17 shows the user interface 340 as presenting statistical information of treatments of the medical condition that can be calculated based on the population medical database 250 (shown in FIG. 3A). FIG. 17 shows the user interface 340 as presenting questions via a follow-up conversation to obtain a diagnosis, and optionally a treatment, determined by a doctor. Advantageously, the follow-up conversation provides a simple way to mark the accuracy of the health predictive model 210, hence creating "closed loop" data for improving the health predictive model 210 (shown in FIG. 3A).

Throughout the dialogue and when presenting the conclusive information, the server system 200 can calculate and present to the user the number of people similar to them (in age, sex, gender and/or collection of described symptoms), so they can have a sense about how many similar cases like theirs the system information is based on (reference population index).

Qualifications for the reference population can be determined based on gender, ethnicity, age group, health condition and then based on the answers provided to the questions that dynamically come up.

The reference population index is used for displaying information to the user throughout a dialog. For example, when the user just starts and reports he/she has a "runny nose," the system can show that "I compare your case to people similar to you and see that I have 8234 cases of women aged 41-45 with Runny Nose." After asking the user if he/she has a cough and the user responds saying he/she also has a cough, the system can show that "I have 6370 cases of women aged 41-45 with Runny Nose and a Cough."

The step of calculating the probability vector and reference population index is done using the classification server in the system. The probability vector can include a vector of probabilities. It performs two calculations:

1. Calculating a probability vector based on a feature vector (or case vector) as explained below). The feature vector can include a vector of features.

2. Estimating the number of people in the population data used to train the classifier that are similar to the given case vector (or a subset of its features). This calculation will be explained further below.

In one embodiment, during the learning phase, the server system 200 can capture statistical information to be able to later calculate the reference population index.

The statistics can include the following, for example:
Total number of case records used for training and testing;
Distribution of cases per age group and gender (age group can be for example 5 years around a certain age);
Condition probability per age and gender group;
Feature (symptom, or particular symptom-attribute value) probability per age and gender group regardless of condition; and/or
Feature (symptom, or particular symptom-attribute value) probability per age and gender group given a specific condition.

The system later uses these statistics to calculate an estimate of the reference population index based on a user age, gender and entered symptoms during the dialogue.

Turning to FIG. 19, an exemplary table of probabilities of an exemplary medical condition is shown for various user ages and genders. Given the above probabilities, the reference population index can be a numerical value that can be calculated by a few different methods. As an example, the reference population index can be calculated by multiplying the probability of selected feature vectors given each condition, summing over all conditions and the selected feature vectors, and multiplying the result by the total population size, as shown in Equation (1).

$$PLM_{index} = \text{population}_{size} * \Sigma\Sigma P(V_i/y_j) * P(y_j) \quad \text{Equation (1)}$$

where $V_i$ in the above Equation (1) is the feature vector and y are the conditions, and $V_i$ can include feature vectors that have relevant symptoms, relevant attribute, relevant values, and/or relevant profile features (such as gender and age). In other words, $Population_{size}$ is the total population size, $V_i$ is a given feature vector having a symptom (for example, a symptom such as "headache," or a specific attribute value such as "headache location being left temple") and $y_j$ being a medical condition, so $P(V_i|y_j)$ means the probability of $V_i$ given $y_j$. $P(y_j)$ is the probability of condition $y_j$ in the whole population.

In the above example, although age and gender are used for selecting the reference population, those of ordinary skill in the art will appreciate that other attributes can be selected by having statistics for any other "cluster" of the reference population. For example, age, sex, gender, and/or Body Mass Index (BMI) ranges can be used, and then the probability of $y_j$ for this cluster of people can be determined.

Using the concept of reference population as the reference group for the diagnosis can be expanded to better explain users the data that the presented information is based on, as well as provide the users with better insights into possible treatment options, medications or other insights regarding the group of people similar to them.

The term "reference population" can be defined in a particular context. In some embodiments, the reference population can include people that have an age that is the same as, and/or similar to, the age of the patient, people that have a gender that is the same as the gender of the patient, or a combination thereof. In other situations, the defining attributes of who is "like me" and who is not, can change to include a completely different set of attributes. An example may illustrate that: if a person breaks his/her arm, it may not be interesting to look at whether he/she smoke or not; but if a cough is considered, smoking status of the patient can become relevant (but the gender of the patient is not necessarily relevant). If pregnancy related situation is considered, then gender is not interesting to look at, because that situation is not relevant to male users.

Presenting users with additional insights on the group of "reference population" can include displaying the number of similar cases. Such a presentation can provide the user with more clarity and transparency and can thus generate more interest and trust in the user for the app and information as to their situation. In contrast, in conventional systems, the user has no idea how the system progress in the dialog, or how the system makes its decisions. A few examples:

A. Location related aspects of reference population—for example, showing where people with runny nose are located right now. For example, the server system 200 (shown in FIG. 1) can select the people (or the medical cases 246) with the symptom and display locations of the people (or the medical cases 246) on a map 360 (shown in FIG. 26) on the user interface 340.

B. Time related aspects of reference population—show how the size of a particular reference population group changes over time—how many people in the reference population in the data were diagnosed with IBS over time, or show how reference population who at some point were diagnosed with IBS evolved over time—what other conditions they had, etc. For example, the user interface 340 can present a visualization for how the reference population are distributed over a timeline 308 (shown in FIG. 27). Additionally and/or alternatively, time evolution of the reference population can include when the reference population recover from the medical condition, when and/or whether the reference population contract a similar/related disease later in life, or a combination thereof.

Presenting the reference population index as it changes along a health dialog is a good way to provide users with a sense of trust and relevancy to both the questions the app asks, as well as to the displayed information at the end of the dialogue.

Improved calculation of reference population index—as stated above, the concept of reference population is context specific, so the calculation of the reference population index should take the context into consideration. Inside the context of a health dialog, a proposed way to calculate a reference population index that is most relevant to that stage in the dialogue can be as following.

(a) Given the current state feature vector—that is, the set of profile features (age, gender, medical history, etc.) and symptoms described so far in the app, iterate over all possible subsets of features in this vector that will present the same and/or similar conditions probability distribution. In one embodiment, the subsets can be selected by running a greedy approximation and adding features incrementally until a threshold requirement is met as described below.

(b), select the features that are presented in those subsets as the relevant features for calculating the reference population index using the following formula:

$$PLM_{index} = population_{size} * P((x'_{profile}, x'_{symptoms}))$$

Where $x'_{profile} \subseteq x_{profile}$
$x'_{symptoms} \subseteq x_{symptoms}$
$d(f(x'_{profile}, x_{symptoms}), f(x_{profile}, x_{symptoms})) \leq \epsilon$ where d is a distribution distance function and f is a condition classifier. For example, the term $P((x'_{profile}, x'_{symptoms})$ can be calculated using Equation (1), or optionally, using (2) as following:

$$PLM_{index} = population_{size} * \Sigma\Sigma P(V_i|y_j) * P(y_j) \quad \text{Equation (2)}$$

The summation is over all feature vectors $V_i$ having all the $x'_{symptoms}$ and $x'_{profiles}$.

To better explain the "Improved reference population index calculation", here are the steps taken:

1. At a given state in the conversation, the system knows a set of profile features (such as age, gender, smoking state, diabetes, other existing conditions, past surgeries, allergies, etc.)—this is denoted as $x_{profile}$.

2. At that same given state, a set of symptoms and symptom attributes (headache, headache location, vomiting) are known and denote as a set $x_{symptoms}$.

3. For that combined vectors state, using a machine learned model (for example, the health predictive model 210), calculate the distribution of probabilities (that is, a vector for each condition the system knows, where for that condition the probability of having that given the above input vectors is presented). The output vector can be denoted as a current probability vector, or $f(x_{profile}, x_{symptoms})$.

4. Iterate over all possible feature vectors each including a subsets of the profiles and symptoms (denoted $x'_{profile}$ and $x'_{symptoms}$ respectively at each iteration), and then calculate the outputted test probability vector, denoted as a test probability vector, or $f(x'_{profile}, x'_{symptoms})$.

5. For each iteration, calculate the distance between the test probability vector of this iteration from the current output probability vector: $d(f(x'_{profile}, x_{symptoms}), f(x_{profile}, x_{symptoms}))$.

6. Union all profile features and symptoms where that distance is smaller than some threshold into the set of "relevant features" to consider for the reference population calculation. This union set can be denoted as $u_{profile}$, $u_{symptoms}$ (for example), and then the relevant reference population index can be:

$$PLM_{index} = population_{size} * P((u'_{profile}, u'_{symptoms}))$$

Additionally and/or alternatively, the set of relevant features can include a minimal set of symptoms (in terms of number of symptoms) that has a distance under the mentioned threshold. Stated somewhat differently, the set of relevant features can be the smallest subset of the profiles and symptoms that has the distance under the mentioned threshold.

An alternative and/or alternative way to calculate reference population can be based on a latent space as described below.

1. Create a latent space based on all patient's data such that patients will be located in proximity to similar patients. This is done by Latent Dirichlet Allocation (LDA), or variational-auto-encoder (VAE) or conditional-VAE to capture similarities given diagnosis or some other property. The latent space can be implemented on the server system 200 (shown in FIG. 1) using any suitable programming language, such as Python, for example. The important property of the resulting space is that distances in the space are meaningful and related to similarity of the original data points (similarity in the sense of the selected property, or of the statistical population distribution). Additionally, this space is of lower dimensionality compared to the original data set.

2. Given a particular patient state (e.g., the set of profile features and symptoms), the feature vector can be embedded into the latent space, and a density of the resulting point in space is estimated. This can be done with the full training data set by going over all points and finding those that fall within an adaptive radius around the particular point. In some embodiment, that would be inefficient and a better way can include creating a density estimation model. Using this model, the fraction of population that is in close proximity can be calculated. This method can be similar or equivalent to $P((u'_{profile}, u'_{symptoms}))$, but this time taking into consideration the inter-dependency of features (while the original calculation was a Naïve one).

An exemplary process of calculating the density estimation model can be as follows.

1. Take all the feature vectors from medical visits data, calculate density for each feature vector using the method mentioned above (that is, by going over all points and finding those that fall within an adaptive radius around the particular point).

2. Train a neural network to predict the density given a feature vector.

3. Use the model to predict density given a feature vector of a new, unseen visit.

Figure 20:
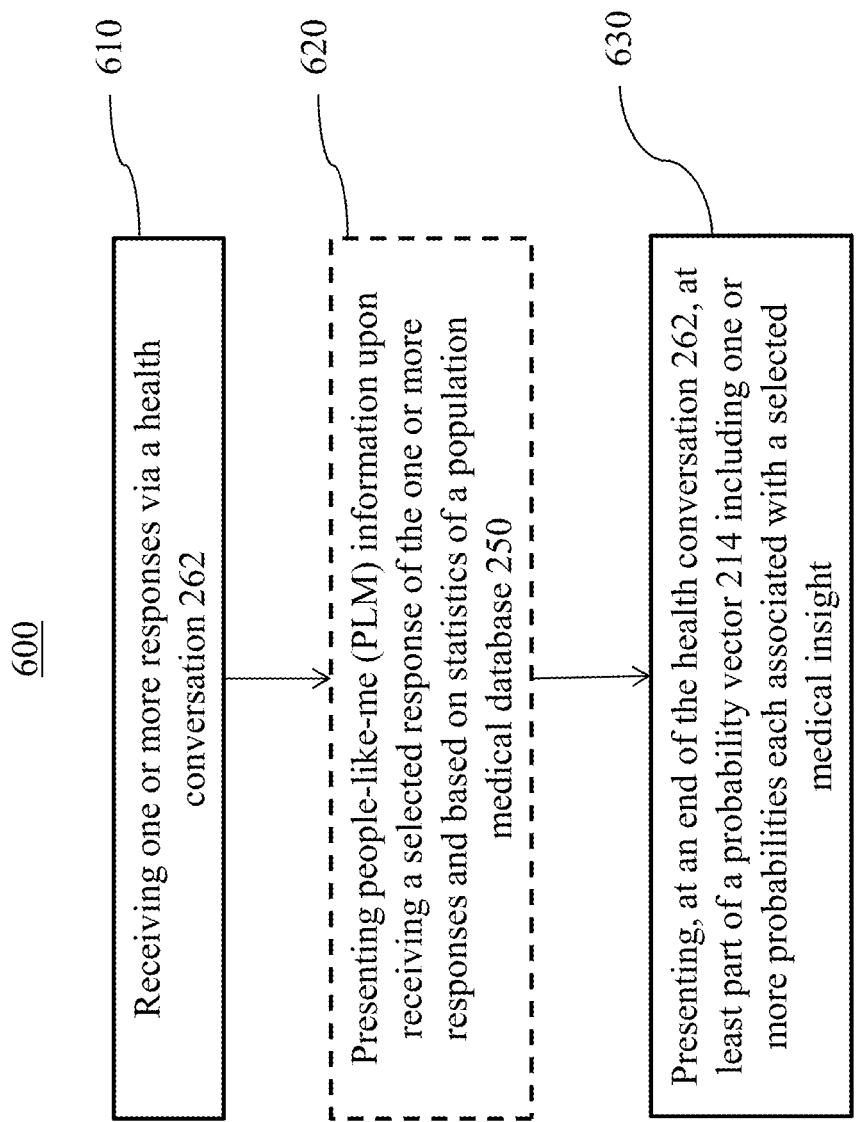
FIG. 20 is a flow diagram illustrating an exemplary embodiment of a method for providing health information via the client device of FIG. 1.

Turning to FIG. 20, a method 600 for providing health information is shown. The method 600 can be implemented by the client device 300 (shown in FIG. 1). One or more responses are received, at 610, via a health conversation 262. Reference population information is optionally presented, at 620, upon receiving a selected response of the one or more responses and based on statistics of a population medical database 250. The probability vector 214 is at least partially presented, at 630, at an end of the health conversation 262. The probability vector 214 can include one or more probabilities each associated with a selected medical condition.

Figure 21:
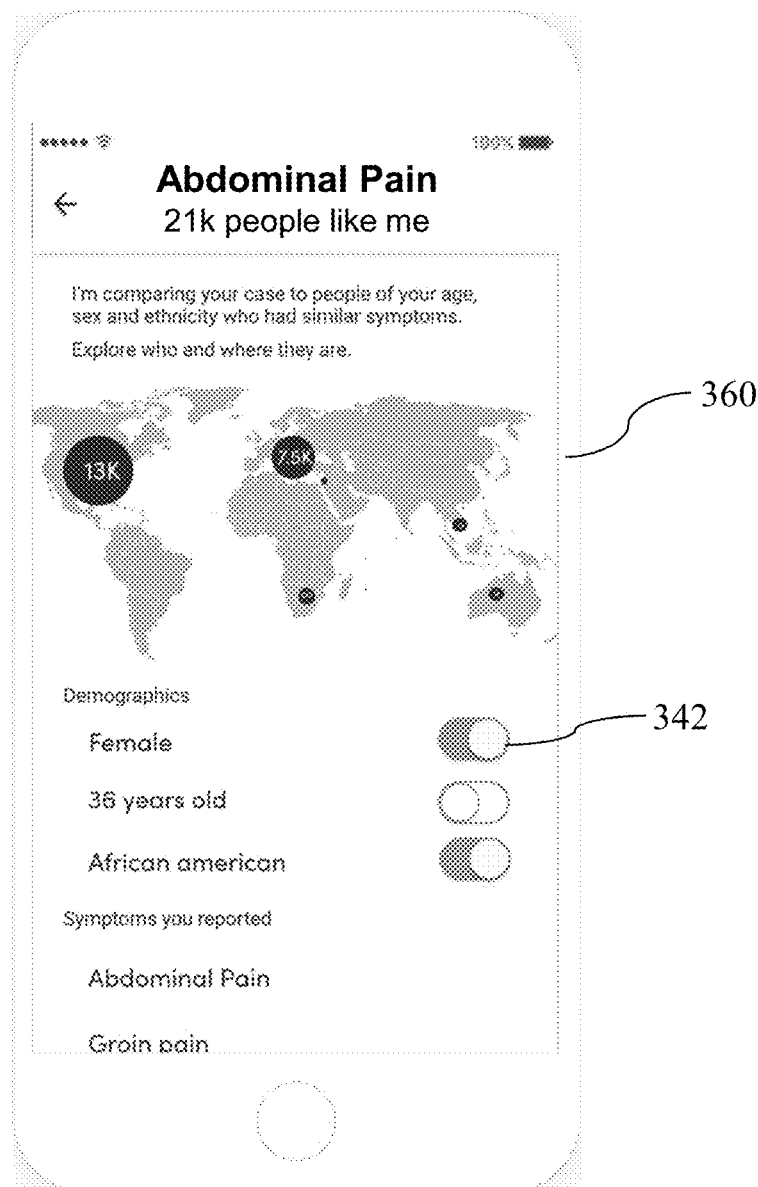
FIGS. 21-32 are detail drawings illustrating exemplary embodiments of a user interface, wherein the user interface is presented on the client device of FIG. 1.

FIG. 21 shows an exemplary detail drawing of the user interface 340 during a selected health conversation 262 (shown in FIG. 5A). The user interface 340 is shown as presenting the reference population index (that is, 49566) based on a population of an age and sex of the current feature vector, symptoms reported by the population (that is, the symptoms in the feature vectors of the population), and the map 360 showing geographical distribution of the population. Optional toggle switches 342 are shown for choosing to or not to include the age or sex in calculating the reference population index or for choosing to or not to include a certain symptom for selecting the population for displaying on the map 360.

Figure 22:
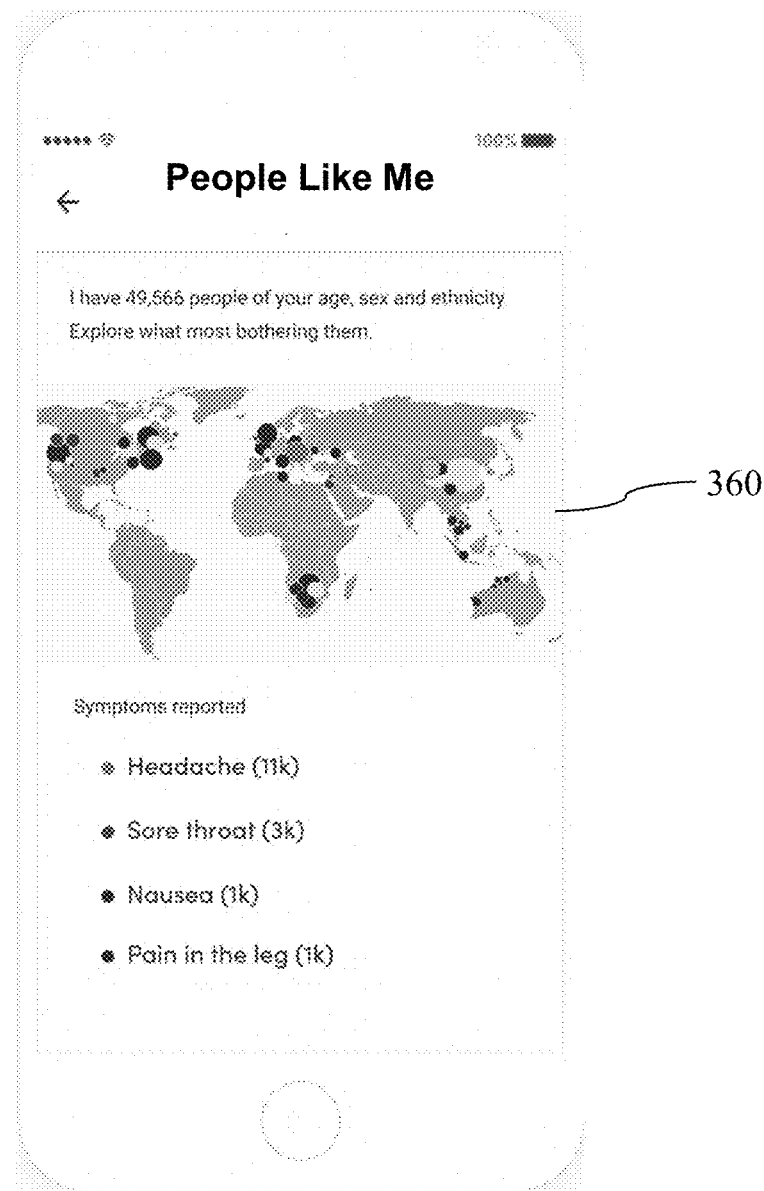

FIG. 22 shows the user interface 340 as presenting, on the map 360 optionally via color coding, groups of the population associated with reported symptoms, respectively.

Figure 23:
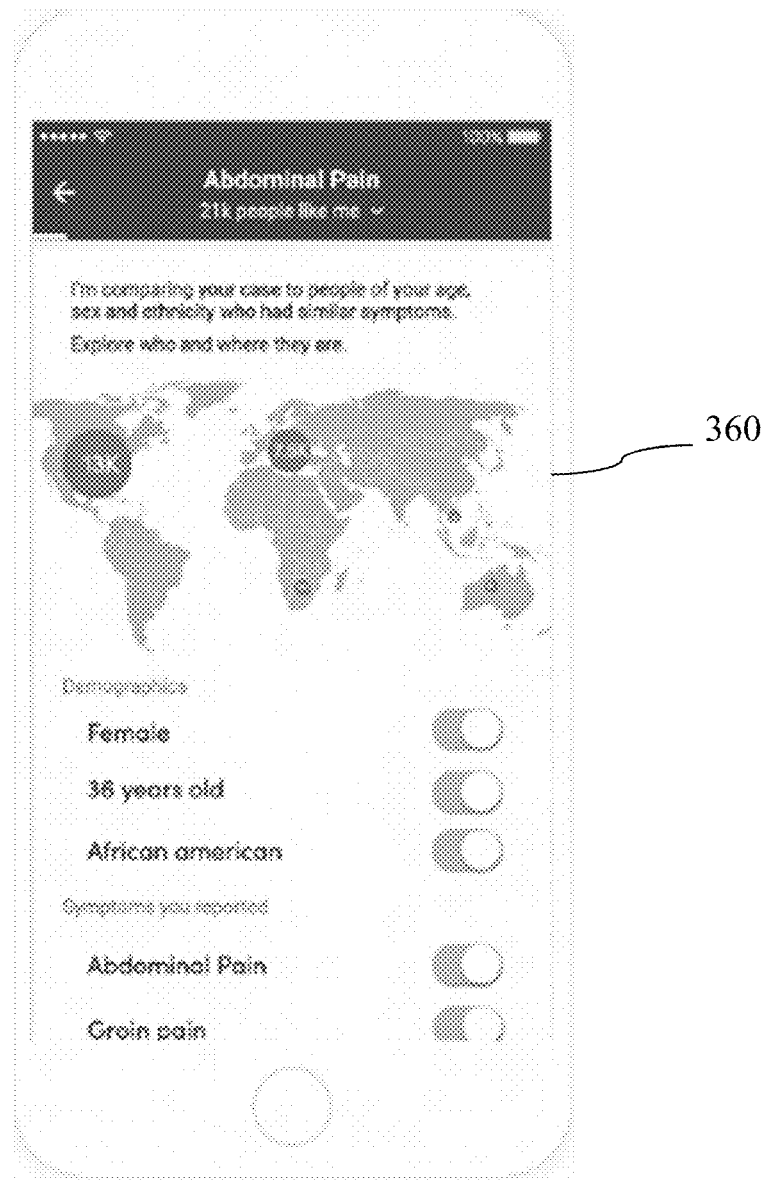

FIG. 23 shows an exemplary detail drawing of the user interface 340 during a selected health conversation 262 (shown in FIG. 5A). The user interface 340 is shown as presenting the reference population index (that is, 21000 or 21 k) based on a population of an age, sex and ethnicity of the current feature vector, symptoms of the current feature vector, and the map 360 showing geographical distribution of the population. The optional toggle switches 342 are shown for choosing to or not to include the age, sex or ethnicity in calculating the reference population index or for choosing to or not to include a certain symptom for selecting the population for displaying on the map 360.

Figure 24:
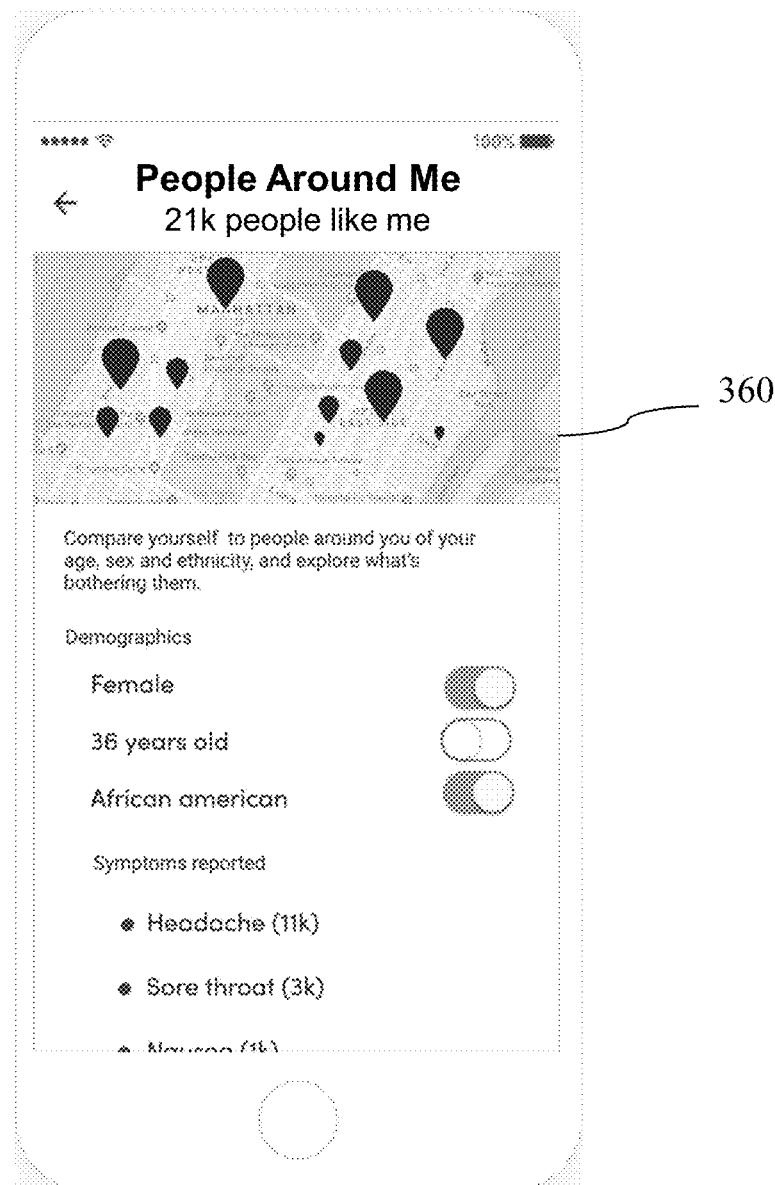

FIG. 24 shows an exemplary detail drawing of the user interface 340 during a selected health conversation 262 (shown in FIG. 5). The user interface 340 is shown as presenting the reference population index (that is, 21000 or 21 k) based on a population of an age, sex and ethnicity of the current feature vector, symptoms reported by the population, and the map 360 showing geographical distribution of the population that is near selected location, such as a location of the client device 300 (shown in FIG. 1) or a location stored in the current feature vector. The optional toggle switches 342 are shown for choosing to or not to include the age, sex or ethnicity in calculating the reference population index or for choosing to or not to include a certain symptom for selecting the population for displaying on the map 360.

Figure 25:
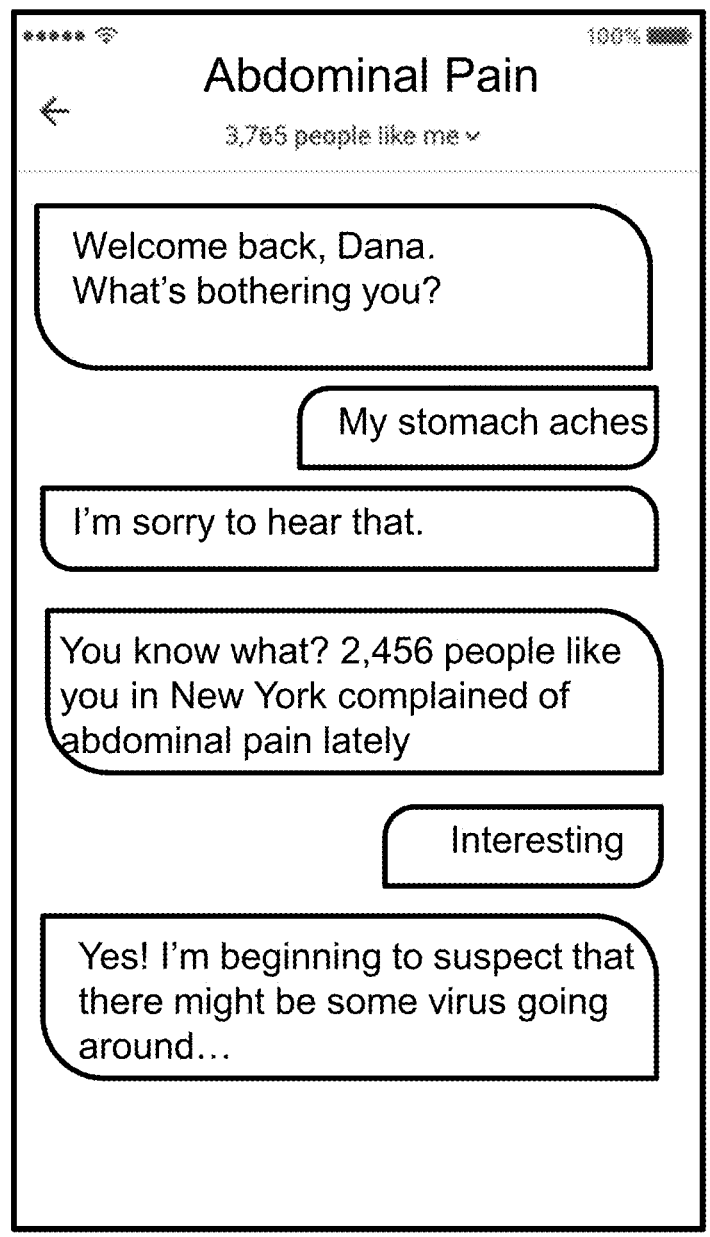

FIG. 25 shows an exemplary detail drawing of the user interface 340 during a selected health conversation 262 (shown in FIG. 5A). The user interface 340 is shown as presenting the reference population index (that is, 2456) based on a population that have selected profile features and the symptom of the current feature vector, and the population is near the selected location.

Figure 26:
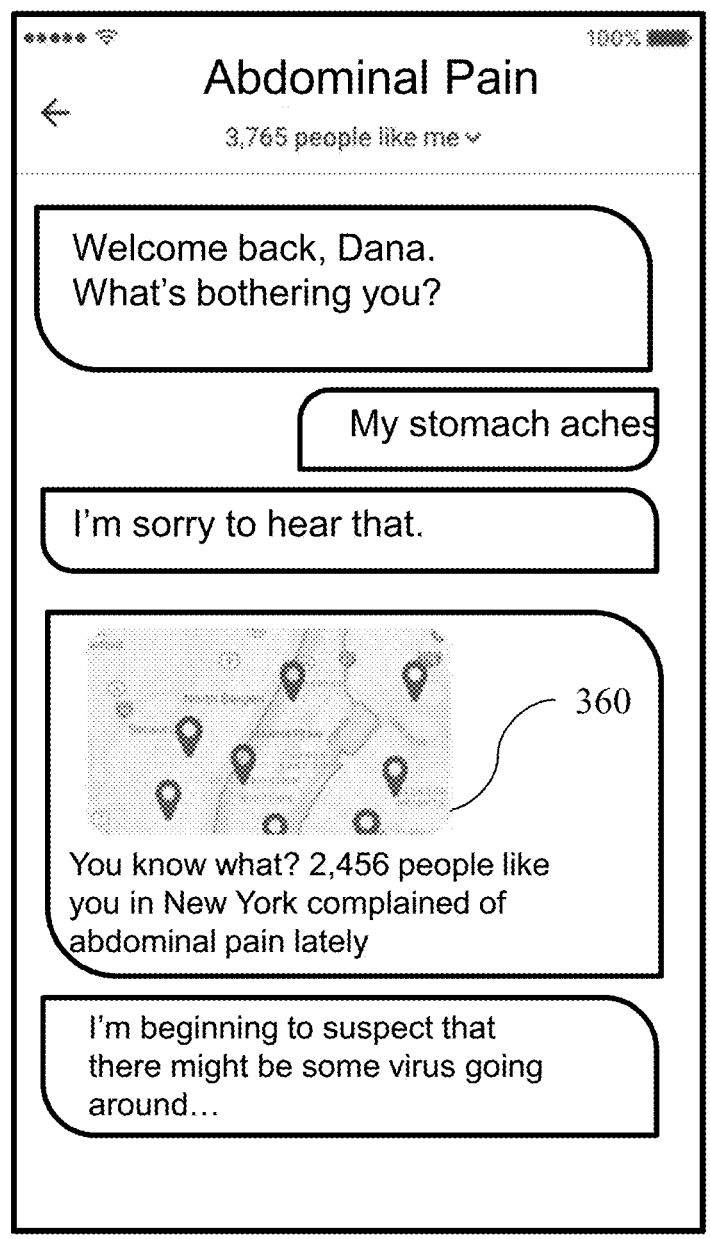

FIG. 26 shows the user interface 340 presenting, on the map 360, geographical distribution of the population that are near the selected location and have selected profile features and the symptom of the current feature vector.

Figure 27:
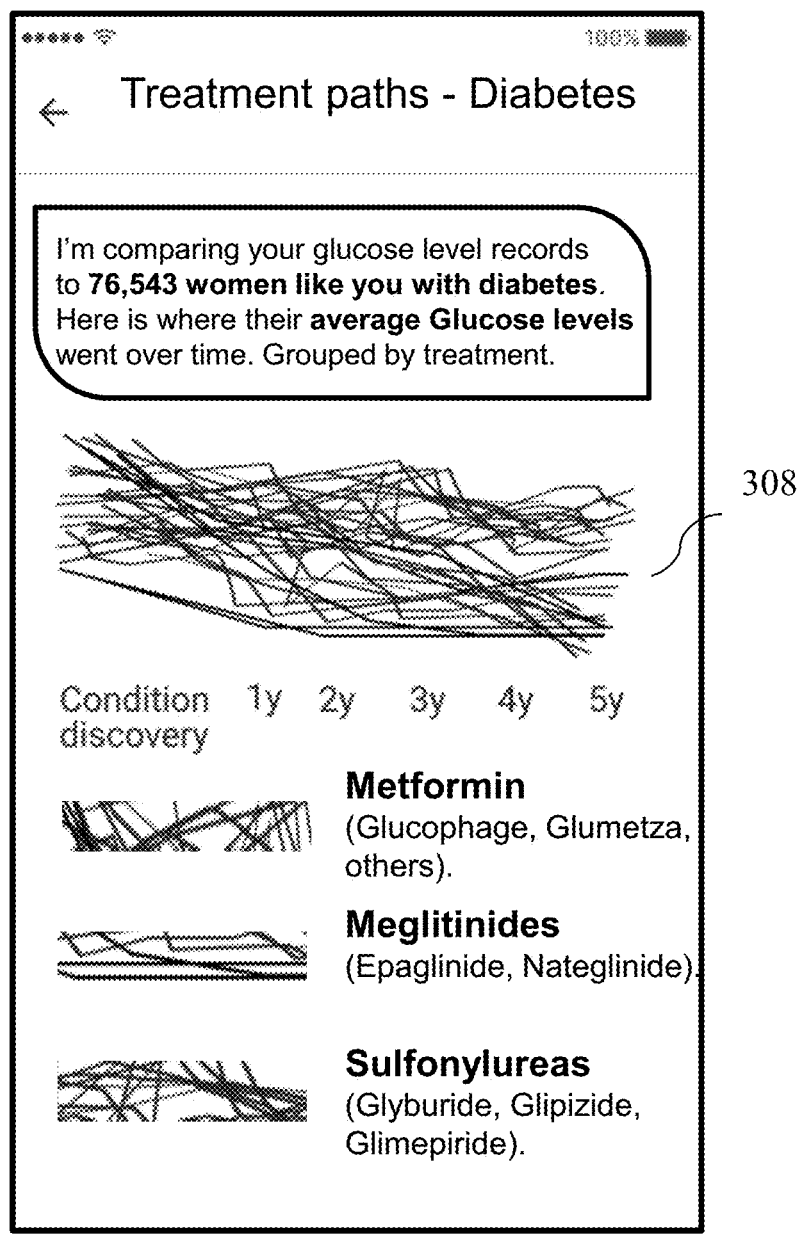

FIG. 27 shows an exemplary detail drawing of the user interface 340 during a selected health conversation 262 (shown in FIG. 5A). The user interface 340 is shown as presenting the reference population index (that is, 76543) based on a population having selected profile feature and medical condition (diabetes) of the current feature vector. The user interface 340 is shown as presenting a value of an attribute (average glucose level) of the population on a symptom timeline 380 for each treatment, optionally via color coding.

Figure 28:
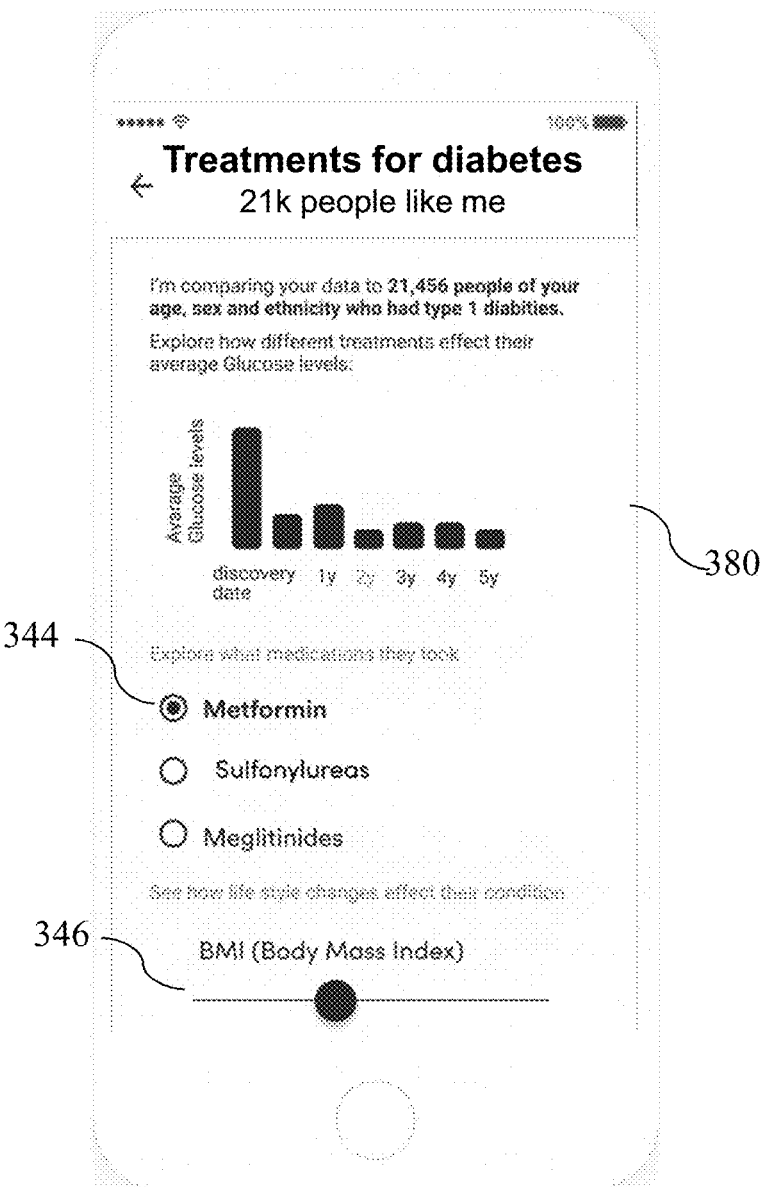

FIG. 28 shows an exemplary detail drawing of the user interface 340 during a selected health conversation 262 (shown in FIG. 5A). The user interface 340 is shown as presenting the reference population index (that is, 21456) based on a population of an age, sex and ethnicity of the current feature vector, a medical condition (type 1 diabetes). The user interface 340 presents a value of an attribute (average glucose level) of the population on a symptom timeline 380. The optional selection buttons 344 can be used to choose a treatment for selecting the population for displaying on the symptom timeline 380. An optional slide bar 346 can be used to select a value of a certain profile feature (illustratively shown as a body mass index) for selecting the population for displaying on the symptom timeline 380.

Figure 29:
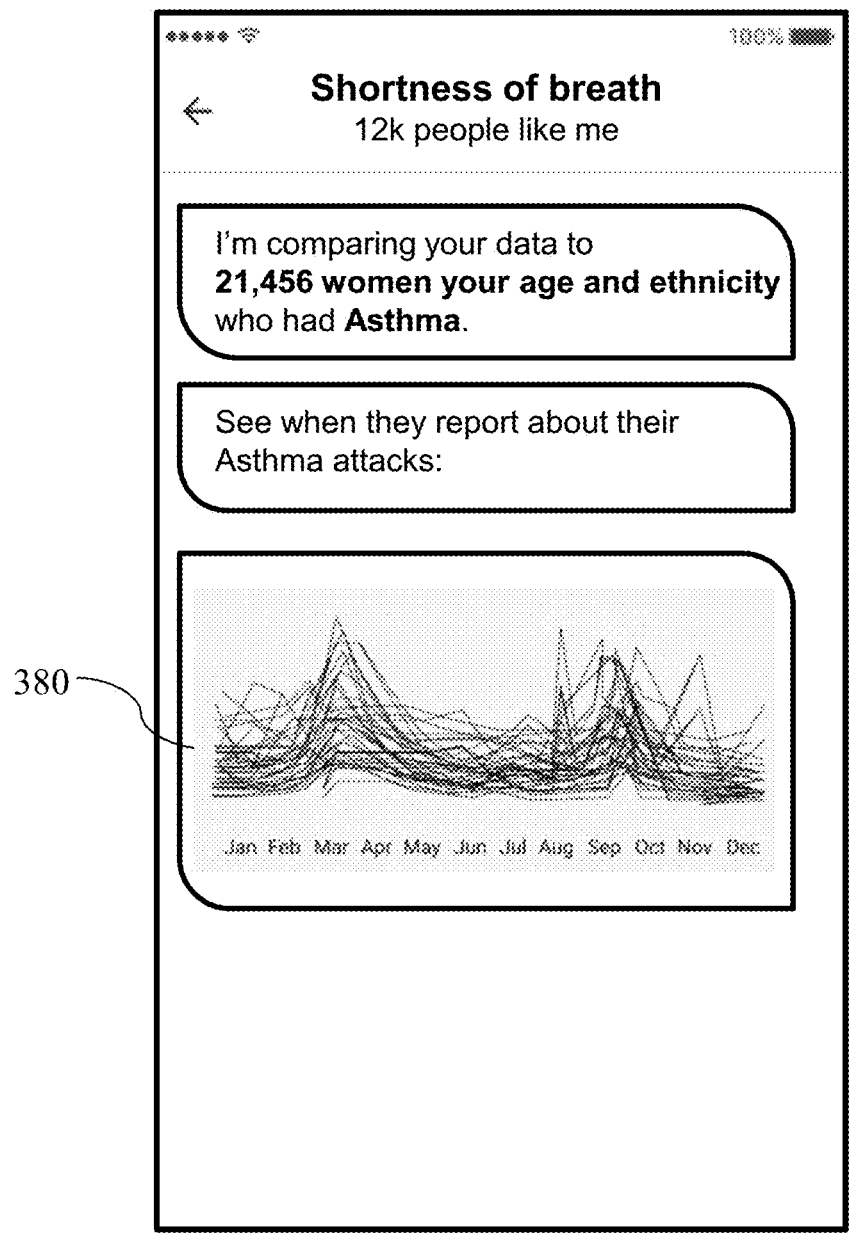

FIG. 29 shows an exemplary detail drawing of the user interface 340 during a selected health conversation 262 (shown in FIG. 5A). The user interface 340 presents the reference population index (that is, 21456) based on a population of an age, sex and ethnicity of the current feature vector, a medical condition (asthma). The user interface 340 presents reporting of the symptom by the population by each month of a year on the symptom timeline 380.

Figure 30:
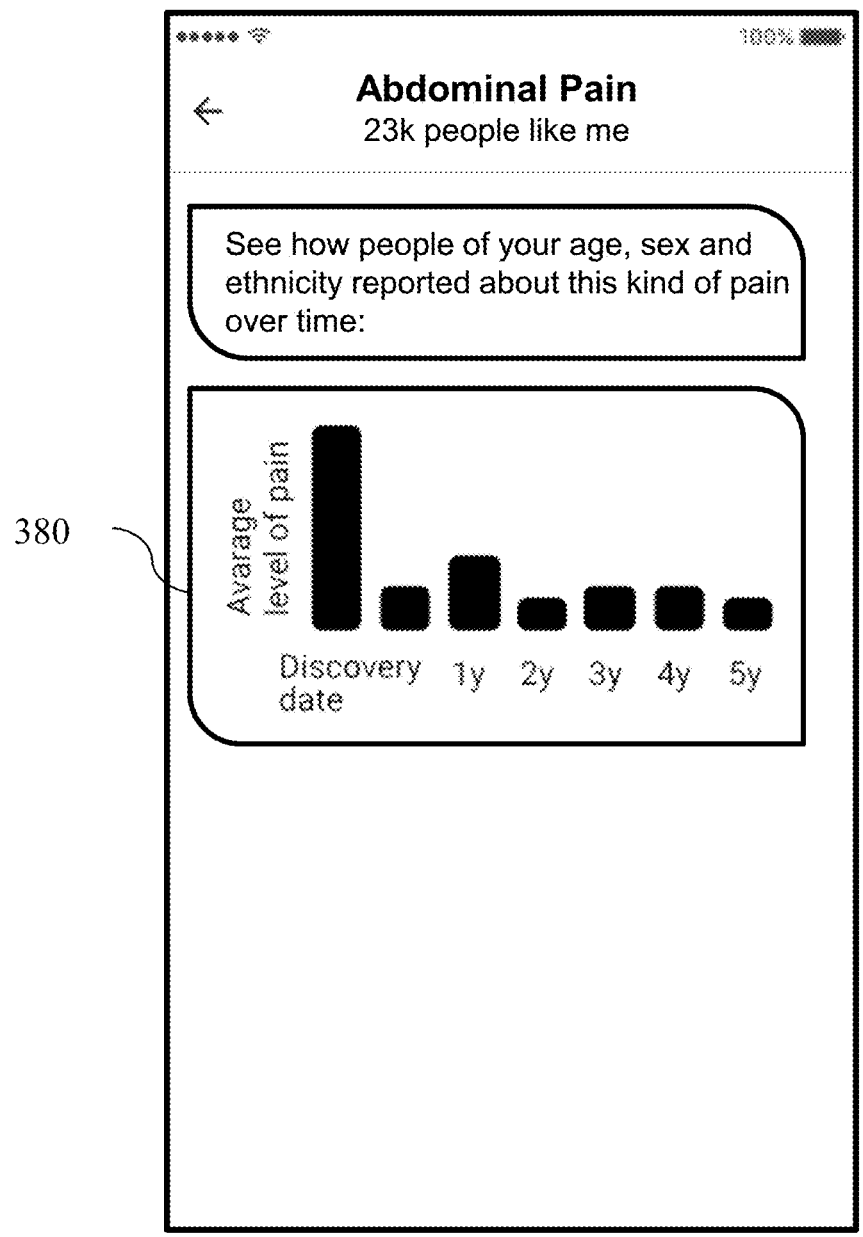

FIG. 30 shows an exemplary detail drawing of the user interface 340 during a selected health conversation 262 (shown in FIG. 5A). The user interface 340 presents the reference population index (that is, 21 k or 21000) based on a population having an age, sex and ethnicity of the current feature vector and having a medical condition (abdominal pain). The user interface 340 presents a value of an attribute (level of pain) of the population on the symptom timeline 380.

Figure 31:
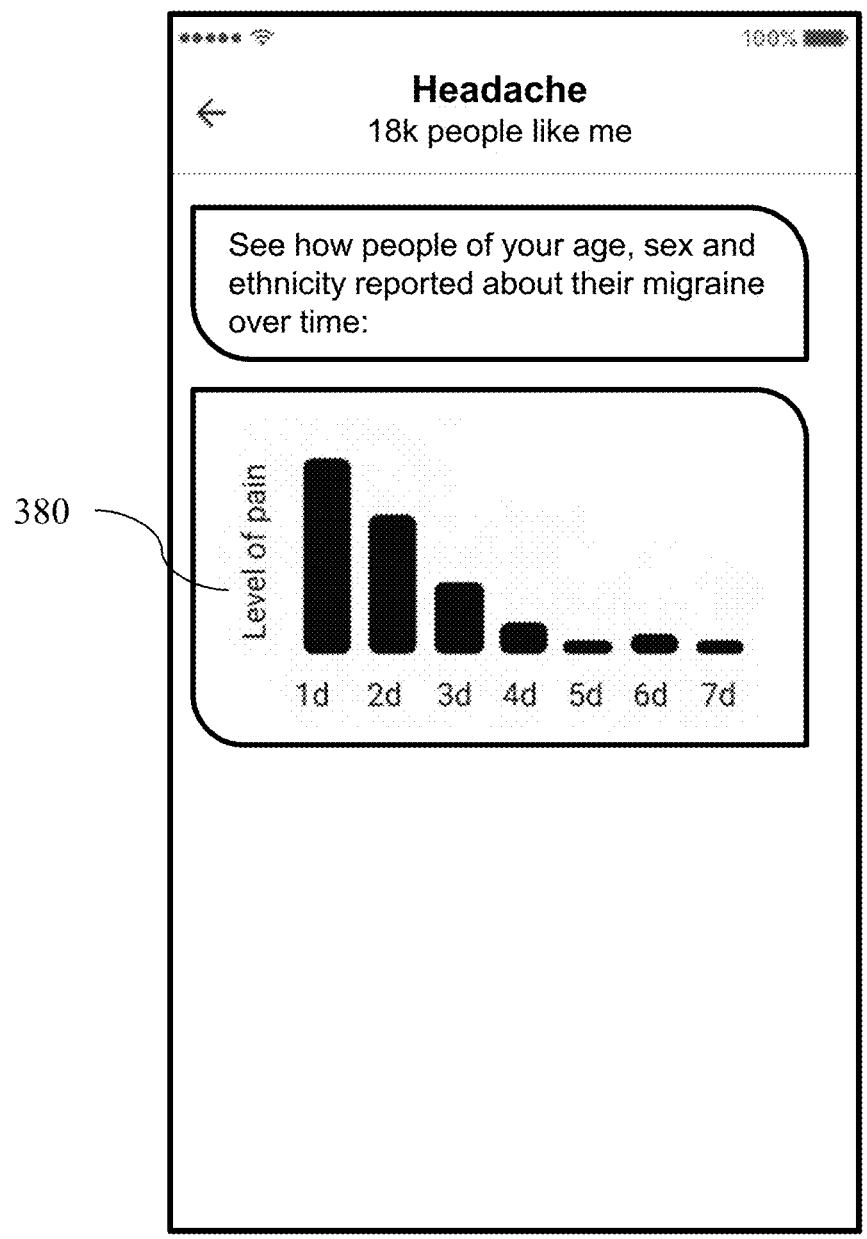

FIG. 31 shows an exemplary detail drawing of the user interface 340 during a selected health conversation 262 (shown in FIG. 5A). The user interface 340 is shown as presenting the reference population index (that is, 21000 or 21 k) based on a population having an age, sex and ethnicity of the current feature vector and having a medical condition (migraine). The user interface 340 presents a value of an attribute (average level of pain) of the population on the symptom timeline 380.

Figure 32:
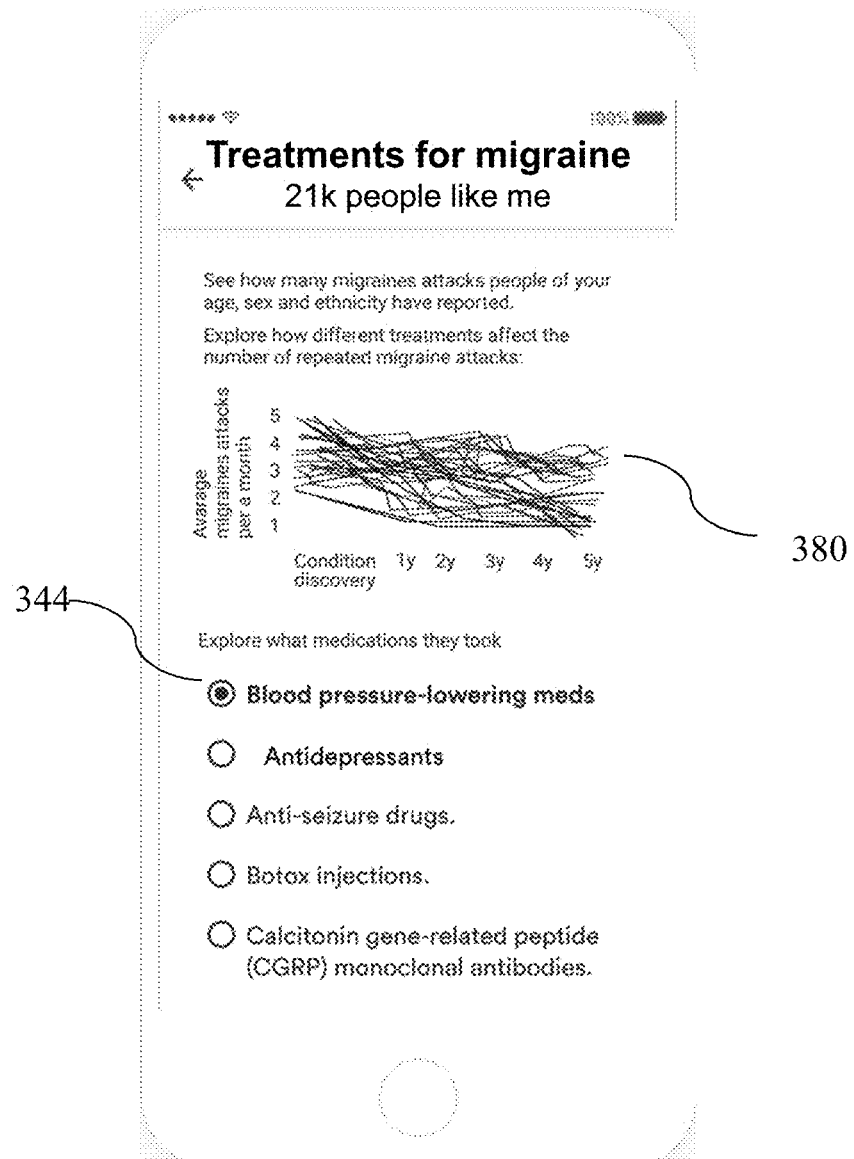

FIG. 32 shows an exemplary detail drawing of the user interface 340 during a selected health conversation 262 (shown in FIG. 5A). The user interface 340 presents the reference population index (that is, 12000 or 12 k) based on a population having selected profile features and medical condition (migraine) of the current feature vector. The user interface 340 presents a value of an attribute (average migraine attacks per month) of the population on a symptom timeline 380. The optional selection buttons 344 are shown for choosing a treatment for selecting the population for displaying on the symptom timeline 380.

Figure 33:
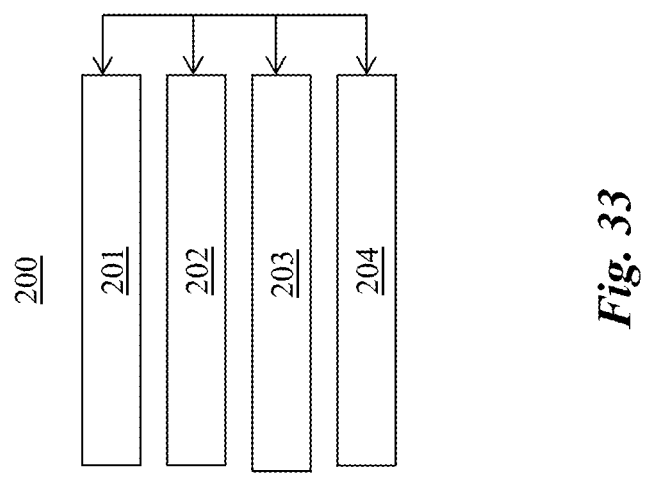
FIG. 33 is a diagram illustrating an exemplary embodiment of the server system of FIG. 1.

Turning to FIG. 33, an exemplary diagram of the server system 200 is shown. An exemplary server system 200 can include one or more servers (or server computers). The server system 200 can be configured for performing processes as shown in one or more of FIGS. 1-13. The server system 200 can include a processor 201. The processor 201 can include one or more general-purpose microprocessors (for example, single or multi-core processors), application-specific integrated circuits, application-specific instruction-set processors, graphics processing units, physics processing units, digital signal processing units, coprocessors, network processing units, encryption processing units, and the like. The processor 201 can execute instructions and/or programs for implementing calculation functions of the server system 200.

As shown in FIG. 33, the server system 200 can include one or more additional hardware components as desired. Exemplary additional hardware components include, but are not limited to, a memory 202 (alternatively referred to herein as a non-transitory computer readable medium). Exemplary memory 202 can include, for example, random access memory (RAM), static RAM, dynamic RAM, read-only memory (ROM), programmable ROM, erasable programmable ROM, electrically erasable programmable ROM, flash memory, secure digital (SD) card, and/or the like. Instructions for implementing the server system 200 can be stored on the memory 202 to be executed by the processor 201.

Additionally and/or alternatively, the server system 200 can include a communication module 203. The communication module 203 can include any conventional hardware and software that operates to exchange data and/or instruction between the server system 200 and the client device 300 (shown in FIG. 1) using any wired and/or wireless communication methods. Exemplary communication methods include, for example, radio, Wireless Fidelity (Wi-Fi), cellular, satellite, broadcasting, or a combination thereof.

Additionally and/or alternatively, the server system 200 can include one or more input/output devices 204 (for example, displays, buttons, a keyboard, keypad, trackball), as desired.

The processor 201, the memory 202, the communication module 203, and/or the input/output device 204 can be configured to communicate, for example, using hardware connectors and buses and/or in a wireless manner.

Although FIG. 33 shows the server system 200 as including one processor 201, one memory 202, one communication module 203, and one input/output device 204, the server system 200 can include any number of uniform and/or different processors 201, memories 202, communication modules 203, and/or input/output devices 204.

Figure 34:
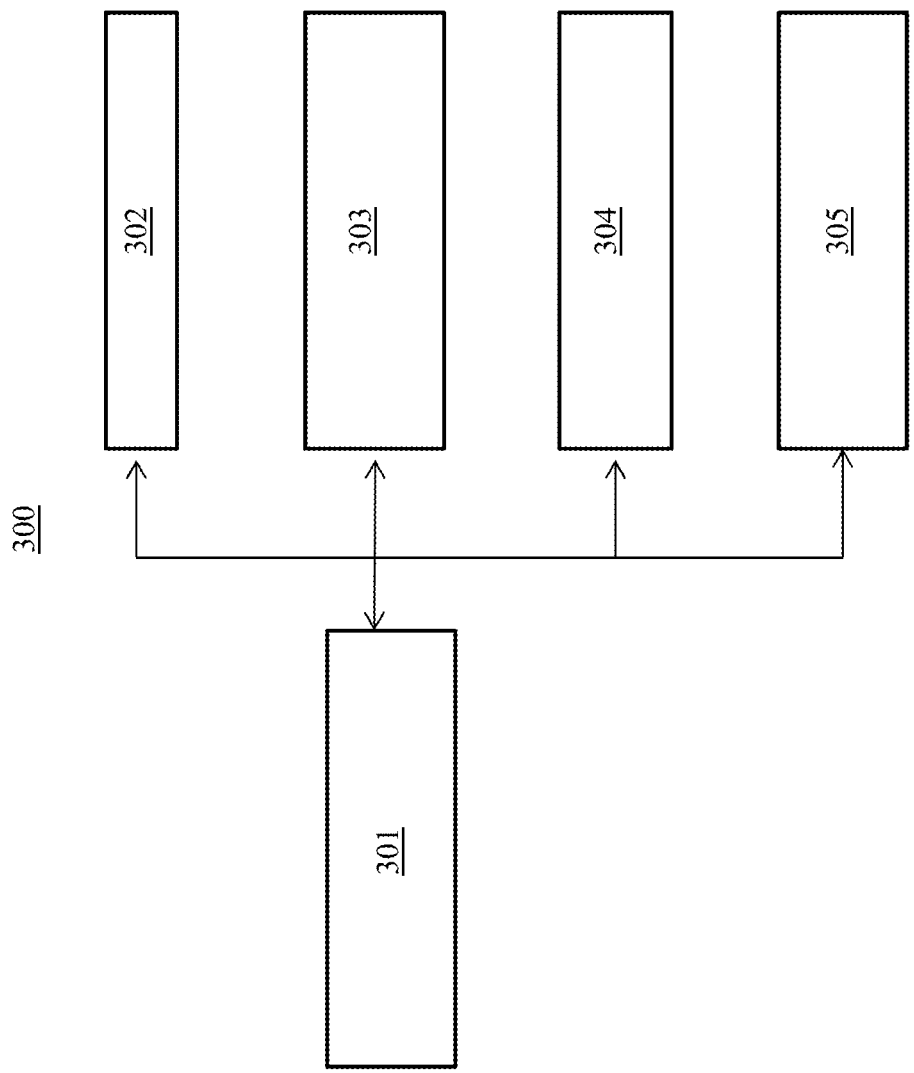
FIG. 34 is a diagram illustrating an exemplary embodiment of the client device of FIG. 1.

Turning to FIG. 34, an exemplary client device 300 is shown. The client device 300 can include a processor 301. The processor 301 can be provided in a similar manner as the processor 201 (shown in FIG. 33). The client device 300 can include a memory 302. The memory 302 can be provided in a similar manner as the memory 202 (shown in FIG. 33).

Coded instructions of the application, app, or program can be installed on the memory 302, to be executed by the processor 301. The application can instruct the processor 302 to communicate with the server system 200 (shown in FIG. 1) to collaboratively provide functions for social interaction. The client device 300 can include a communication module 303. The communication module 303 can be provided in a similar manner as the communication module 203 (shown in FIG. 33).

The client device 300 can include an input/output device 304. The input/output device 304 can be provided in a similar manner as the input/output device 204 (shown in FIG. 33). For example, via the input/output device 304, the client device 300 can obtain information inputted by an operator for operating the application, and/or output information of the application to the operator. The processor 301, the memory 302, the communication module 303, and/or the input/output device 304 can be configured to communicate, for example, using hardware connectors and buses and/or in a wireless manner.

The client device 300 can include a positioning device 305 in communication with the processor 301. The positioning device 305 can include any device operating to obtain the device location of the client device 300. The positioning device 305 can be global positioning system (GPS)-based, wireless local area network (WLAN)-based (or WiFi-based), and/or cell transmitter-based. An exemplary positioning device 350 can include a Global positioning system (GPS) module, a differential GPS module, or a combination thereof. In certain embodiments, the positioning device 305 can obtain the location of the client device 300 dynamically and/or in real time. The client device 300 can send the device location to the server system 200.

The disclosed embodiments are susceptible to various modifications and alternative forms, and specific examples thereof have been shown by way of example in the drawings and are herein described in detail. It should be understood, however, that the disclosed embodiments are not to be limited to the particular forms or methods disclosed, but to the contrary, the disclosed embodiments are to cover all modifications, equivalents, and alternatives.

What is claimed is:

1. A method for providing health information, comprising:
    building, via a computer processor, a health predictive model, wherein the health predictive model is based on a plurality of symptom-attribute-value (SAV) ontology objects from free text of a plurality of electronic medical records, a plurality of feature vectors associated with the plurality of electronic medical cases and at least partially based on the SAV ontology objects and at least one diagnoses of a medical condition associated with case of the plurality of electronic medical cases;
    receiving, via the computer processor, one or more responses via an automated health conversation, wherein the automated health conversation comprises repeatedly determining a new question until a final question is determined, and successively outputting the question;
    updating, via the computer processor, a current feature vector based on the one or more responses;
    inputting, via the computer processor, the current feature vector into the health predictive model;
    calculating, via the computer processor, a probability vector based on said inputting, the probability vector including one or more probabilities each associated with a selected medical condition; and
    outputting, via the computer processor, at least one of the one or more probabilities to a display.

2. The method of claim 1, further comprising determining, upon receiving a selected response of the one or more responses, reference population information based on the current feature vector and statistics of the plurality of feature vectors associated with the plurality of medical cases.

3. The method of claim 2, wherein said determining includes calculating a reference population index as a number of the feature vectors having one or more relevant symptoms and one or more relevant profile features that are in the current feature vector.

4. The method of claim 3, wherein said determining includes generating:
   a map that displays locations associated with the reference population having the one or more relevant symptoms and the one or more relevant profile features;
   a symptom timeline that presents an evolution of a value of a selected attribute of one of the relevant symptoms of the reference population;
   the symptom timeline that presents the evolution of the value for each selected medical treatment;
   or a combination thereof.

5. The method of claim 3, wherein said calculating includes calculating the reference population index based on a summation of a product between a probability of a feature vector having the relevant symptoms and the relevant profile features given a medical condition and a probability of the medical condition in the plurality of electronic medical records, the summation being performed over all of the feature vector of the medical cases and over all of the medical conditions of the medical cases.

6. The method of claim 1, further including selecting an attribute of a symptom to ask about during the health conversation, wherein said selecting includes performing a calculation to identify the attribute that results in, among all attributes associated with the symptom:
   a greatest change in information gain based on lowering of an entropy achieved in the probability vector;
   a greatest change in the probability vector; or
   a greatest probability of receiving a positive answer.

7. The method of claim 1, further including selecting an attribute or a symptom to ask about during the health conversation, wherein said selecting is based on a state machine considering the current feature vector and a conversation state and wherein said selecting includes selecting among different models used for calculating the probability vector, selecting among different equations for calculating information gain, or using medical protocols based heuristics.

8. A computer program product for providing health information, the computer program product being encoded on one or more machine-readable storage media and configured to be installed on a client device, the computer program product comprising:
   instruction for receiving one or more responses via an automated health conversation, wherein the automated health conversation comprises repeatedly determining a new question until a final question is determined, and successively outputting the question;
   instruction for presenting reference population information upon receiving a selected response of the one or more responses and based on statistics of a plurality of electronic medical records, the reference population information including a reference population index presented as a number of people in the plurality of electronic medical records that have one or more relevant symptoms and one or more relevant profile features associated with the health conversation; and
   instruction for presenting to a display, at an end of the health conversation, at least part of a probability vector including one or more probabilities each associated with a selected medical condition, the probability vector being calculated based at least partially on the one or more responses and a health predictive model, wherein the health predictive model is based on a plurality of symptom-attribute-value (SAV) ontology objects from free text of a plurality of electronic medical records, a plurality of feature vectors associated with the plurality of electronic medical cases and at least partially based on the SAV ontology objects and at least one diagnoses of a medical condition associated with case of the plurality of electronic medical cases.

\* \* \* \* \*